US009081001B2

(12) United States Patent
Cook et al.

(10) Patent No.: US 9,081,001 B2
(45) Date of Patent: Jul. 14, 2015

(54) DIAGNOSTIC SYSTEMS AND INSTRUMENTS

(71) Applicant: Wellstat Diagnostics, LLC, Gaithersburg, MD (US)

(72) Inventors: Richard Alan Cook, Derwood, MD (US); Sang Cho, Rockville, MD (US); Charles Quentin Davis, Frederick, MD (US); Kevin E Dorsey, Germantown, MD (US); Jason Charles Harley, Gaithersburg, MD (US); Jonathan Leland, Gaithersburg, MD (US); Rober Krikor Matikyan, Potomac, MD (US); Sjef Otten, Gaithersburg, MD (US); Jeffrey Howard Peterman, Silver Spring, MD (US); Brian B Thomas, Frederick, MD (US)

(73) Assignee: Wellstat Diagnostics, LLC, Gaithersburg, MD (US)

( * ) Notice: Subject to any disclaimer, the term of this patent is extended or adjusted under 35 U.S.C. 154(b) by 22 days.

(21) Appl. No.: 13/844,450

(22) Filed: Mar. 15, 2013

(65) Prior Publication Data
US 2013/0315780 A1 Nov. 28, 2013

Related U.S. Application Data

(63) Continuation-in-part of application No. PCT/US2012/067041, filed on Nov. 29, 2012.

(60) Provisional application No. 61/647,272, filed on May 15, 2012.

(51) Int. Cl.
*G01N 21/00* (2006.01)
*G01N 33/50* (2006.01)
(Continued)

(52) U.S. Cl.
CPC .............. *G01N 33/50* (2013.01); *F04B 49/065* (2013.01); *F04B 49/106* (2013.01); *G01N 21/66* (2013.01);
(Continued)

(58) Field of Classification Search
CPC ...... G01N 33/50; G01N 21/66; F04B 49/065; F04B 49/106; H05B 1/025
USPC ......... 422/52, 73, 82.01, 82.05, 82.06, 82.07, 422/82.08, 82.09, 82.11, 407, 501, 502, 422/503, 504, 507; 436/17, 43, 63, 94, 149, 436/164, 172, 174, 177, 517, 518, 805, 436/809; 435/4, 6.1, 6.11, 6.12, 7.1, 7.92, 435/29, 288.5
See application file for complete search history.

(56) References Cited

U.S. PATENT DOCUMENTS 3,705,100 A  12/1972 Blatt et al.
4,212,742 A   7/1980 Solomon et al.
(Continued)

FOREIGN PATENT DOCUMENTS

EP    486059       1/1997
EP    1489303 B1   12/2004
(Continued)

OTHER PUBLICATIONS

Ascoli, et al., "Drug Binding to Human Serum Albumin: Abridged Review of Results Obtained with High-Performance Liquid Chromatography and Circular Dichroism", Chirality, vol. 18:667-679 (2006).
(Continued)

*Primary Examiner* — Dennis M White

(57) ABSTRACT

Provided is a clinical diagnostic system that comprises a diagnostic instrument and a disposable cartridge. The diagnostic system can be used to measure assays in point of care clinical settings.

150 Claims, 29 Drawing Sheets

(51) Int. Cl.
*G01N 21/66* (2006.01)
*F04B 49/06* (2006.01)
*H05B 1/02* (2006.01)
*F04B 49/10* (2006.01)
*G01N 33/58* (2006.01)

(52) U.S. Cl.
CPC .............. *G01N 33/58* (2013.01); *G01N 33/582* (2013.01); *H05B 1/025* (2013.01); *B01L 2200/10* (2013.01); *B01L 2300/0861* (2013.01); *Y10T 436/25* (2015.01); *Y10T 436/2575* (2015.01)

(56) References Cited

U.S. PATENT DOCUMENTS

| | | | |
|---|---|---|---|
| 4,225,410 | A | 9/1980 | Pace |
| 4,228,015 | A | 10/1980 | De Vries et al. |
| 4,301,412 | A | 11/1981 | Hill et al. |
| 4,301,414 | A | 11/1981 | Hill et al. |
| 4,336,121 | A | 6/1982 | Enzer et al. |
| 4,381,775 | A | 5/1983 | Nose' et al. |
| 4,397,725 | A | 8/1983 | Enzer et al. |
| 4,436,610 | A | 3/1984 | Enzer et al. |
| 4,540,492 | A | 9/1985 | Kessler |
| 4,548,498 | A | 10/1985 | Folestad et al. |
| 4,631,130 | A | 12/1986 | Watanabe |
| 4,675,300 | A | 6/1987 | Zare et al. |
| 4,735,718 | A | 4/1988 | Peters |
| 4,735,776 | A | 4/1988 | Yamamoto et al. |
| 4,762,594 | A | 8/1988 | Guruswamy |
| 4,786,394 | A | 11/1988 | Enzer et al. |
| 4,799,393 | A | 1/1989 | Uffenheimer |
| 4,820,129 | A | 4/1989 | Magnussen, Jr. |
| 4,833,087 | A | 5/1989 | Hinckley |
| 4,835,477 | A | 5/1989 | Polaschegg et al. |
| 4,887,458 | A | 12/1989 | Baker et al. |
| 4,929,426 | A | 5/1990 | Bodai et al. |
| 4,965,049 | A | 10/1990 | Lillig et al. |
| 5,023,054 | A | 6/1991 | Sato et al. |
| 5,061,445 | A | 10/1991 | Zoski et al. |
| 5,068,088 | A | 11/1991 | Hall et al. |
| 5,074,977 | A | 12/1991 | Cheung et al. |
| 5,093,268 | A | 3/1992 | Leventis et al. |
| 5,096,582 | A | 3/1992 | Lombardi et al. |
| 5,130,254 | A | 7/1992 | Collier et al. |
| 5,139,328 | A | 8/1992 | Baker et al. |
| 5,139,685 | A | 8/1992 | de Castro et al. |
| 5,143,084 | A | 9/1992 | Macemon et al. |
| 5,147,806 | A | 9/1992 | Kamin et al. |
| 5,155,039 | A | 10/1992 | Chrisope et al. |
| 5,208,163 | A | 5/1993 | Charlton et al. |
| 5,223,219 | A | 6/1993 | Subramanian et al. |
| 5,223,718 | A | 6/1993 | Taboada |
| 5,238,808 | A | 8/1993 | Bard et al. |
| 5,247,243 | A | 9/1993 | Hall et al. |
| 5,279,797 | A | 1/1994 | Burns et al. |
| 5,288,646 | A | 2/1994 | Lundsgaard et al. |
| 5,296,191 | A | 3/1994 | Hall et al. |
| 5,298,224 | A | 3/1994 | Plum |
| 5,302,348 | A | 4/1994 | Cusack et al. |
| 5,310,687 | A | 5/1994 | Bard et al. |
| 5,316,730 | A | 5/1994 | Blake et al. |
| 5,372,946 | A | 12/1994 | Cusak et al. |
| 5,399,486 | A | 3/1995 | Cathey et al. |
| 5,405,510 | A | 4/1995 | Betts et al. |
| 5,416,026 | A | 5/1995 | Davis |
| 5,453,356 | A | 9/1995 | Bard et al. |
| 5,466,416 | A | 11/1995 | Ghaed et al. |
| 5,487,870 | A | 1/1996 | McKinney et al. |
| 5,500,187 | A | 3/1996 | Deoms et al. |
| 5,504,011 | A | 4/1996 | Gavin et al. |
| 5,506,142 | A | 4/1996 | Mahaffey et al. |
| 5,522,255 | A | 6/1996 | Neel et al. |
| 5,525,518 | A | 6/1996 | Lundsgaard et al. |
| 5,527,710 | A | 6/1996 | Nacamulli et al. |
| 5,534,226 | A | 7/1996 | Gavin et al. |
| 5,543,112 | A | 8/1996 | Ghead et al. |
| 5,558,838 | A | 9/1996 | Uffenheimer |
| 5,567,869 | A | 10/1996 | Hauch et al. |
| 5,575,977 | A | 11/1996 | McKinney et al. |
| 5,591,403 | A | 1/1997 | Gavin et al. |
| 5,591,581 | A | 1/1997 | Massey et al. |
| 5,593,638 | A | 1/1997 | Davis |
| 5,597,910 | A | 1/1997 | Gudibande et al. |
| 5,599,447 | A | 2/1997 | Pearl et al. |
| 5,601,727 | A | 2/1997 | Bormann et al. |
| 5,602,037 | A | 2/1997 | Ostgaard et al. |
| 5,610,075 | A | 3/1997 | Stahl-Rees |
| 5,624,637 | A | 4/1997 | Ghaed et al. |
| 5,627,041 | A | 5/1997 | Shartle |
| 5,629,209 | A | 5/1997 | Braun, Sr. et al. |
| 5,635,347 | A | 6/1997 | Link et al. |
| 5,641,623 | A | 6/1997 | Martin |
| 5,643,713 | A | 7/1997 | Liang et al. |
| 5,653,243 | A | 8/1997 | Lauks et al. |
| 5,660,993 | A | 8/1997 | Cathey et al. |
| 5,665,238 | A | 9/1997 | Whitson et al. |
| 5,665,315 | A | 9/1997 | Robert et al. |
| 5,666,967 | A | 9/1997 | Lauks et al. |
| 5,679,519 | A | 10/1997 | Oprandy et al. |
| 5,686,244 | A | 11/1997 | Gudibande et al. |
| 5,698,406 | A | 12/1997 | Cathey et al. |
| 5,700,427 | A | 12/1997 | Ghaed et al. |
| 5,705,402 | A | 1/1998 | Leland et al. |
| 5,714,089 | A | 2/1998 | Bard et al. |
| 5,716,781 | A | 2/1998 | Massey et al. |
| 5,720,922 | A | 2/1998 | Ghaed et al. |
| 5,731,147 | A | 3/1998 | Bard et al. |
| 5,736,404 | A | 4/1998 | Yassinzadeh et al. |
| 5,743,861 | A | 4/1998 | Columbus et al. |
| 5,744,367 | A | 4/1998 | Talley et al. |
| 5,746,974 | A | 5/1998 | Massey et al. |
| 5,747,666 | A | 5/1998 | Willis |
| 5,770,459 | A | 6/1998 | Massey et al. |
| 5,779,650 | A | 7/1998 | Lauks et al. |
| 5,779,976 | A | 7/1998 | Leland et al. |
| 5,795,543 | A | 8/1998 | Poto et al. |
| 5,798,083 | A | 8/1998 | Massey et al. |
| 5,800,781 | A | 9/1998 | Gavin et al. |
| 5,804,400 | A | 9/1998 | Martin et al. |
| 5,821,399 | A | 10/1998 | Zelin |
| 5,827,481 | A | 10/1998 | Bente et al. |
| 5,846,485 | A | 12/1998 | Leland et al. |
| 5,851,488 | A | 12/1998 | Saul et al. |
| RE36,054 | E | 1/1999 | Blake et al. |
| 5,858,676 | A | 1/1999 | Yang et al. |
| 5,882,602 | A | 3/1999 | Savage et al. |
| 5,885,533 | A | 3/1999 | Savage et al. |
| 5,888,826 | A | 3/1999 | Ostgaard et al. |
| 5,912,134 | A | 6/1999 | Shartle |
| 5,914,042 | A | 6/1999 | Ball et al. |
| 5,919,711 | A | 7/1999 | Boyd et al. |
| 5,922,210 | A | 7/1999 | Brody et al. |
| 5,935,779 | A | 8/1999 | Massey et al. |
| 5,945,344 | A | 8/1999 | Hayes et al. |
| 5,962,218 | A | 10/1999 | Leland et al. |
| 5,968,329 | A | 10/1999 | Anderson et al. |
| 5,980,830 | A | 11/1999 | Savage et al. |
| 5,981,294 | A | 11/1999 | Blatt et al. |
| 5,983,734 | A | 11/1999 | Mathur et al. |
| 6,016,712 | A | 1/2000 | Warden et al. |
| 6,048,687 | A | 4/2000 | Kenten et al. |
| 6,057,151 | A | 5/2000 | Greenwood et al. |
| 6,069,014 | A | 5/2000 | Schrier et al. |
| 6,078,782 | A | 6/2000 | Leland et al. |
| 6,082,185 | A | 7/2000 | Saaski |
| 6,087,476 | A | 7/2000 | Kenten et al. |
| 6,096,500 | A | 8/2000 | Oprandy et al. |
| 6,099,760 | A | 8/2000 | Jameison et al. |
| 6,112,888 | A | 9/2000 | Sauro et al. |
| 6,120,986 | A | 9/2000 | Martin |
| 6,132,648 | A | 10/2000 | Zhang et al. |
| 6,132,955 | A | 10/2000 | Talley et al. |

(56) References Cited

U.S. PATENT DOCUMENTS

| | | |
|---|---|---|
| 6,140,138 A | 10/2000 | Bard et al. |
| 6,146,838 A | 11/2000 | Williams et al. |
| 6,165,708 A | 12/2000 | Liang et al. |
| 6,165,729 A | 12/2000 | Leland et al. |
| 6,174,709 B1 | 1/2001 | Kenten et al. |
| 6,187,267 B1 | 2/2001 | Taylor et al. |
| 6,193,864 B1 | 2/2001 | Leader et al. |
| 6,200,531 B1 | 3/2001 | Liljestrand et al. |
| 6,214,552 B1 | 4/2001 | Heroux et al. |
| 6,217,744 B1 | 4/2001 | Crosby |
| 6,271,041 B1 | 8/2001 | Leland et al. |
| 6,274,087 B1 | 8/2001 | Preston et al. |
| 6,312,591 B1 | 11/2001 | Vassarotti et al. |
| 6,312,896 B1 | 11/2001 | Heroux et al. |
| 6,316,180 B1 | 11/2001 | Martin |
| 6,316,607 B1 | 11/2001 | Massey et al. |
| 6,319,670 B1 | 11/2001 | Sigal et al. |
| 6,319,719 B1 | 11/2001 | Bhullar et al. |
| 6,325,973 B1 | 12/2001 | Leland et al. |
| 6,379,969 B1 | 4/2002 | Mauze et al. |
| 6,387,290 B1 | 5/2002 | Brody et al. |
| 6,391,541 B1 | 5/2002 | Petersen et al. |
| 6,398,956 B1 | 6/2002 | Coville et al. |
| 6,403,384 B1 | 6/2002 | Lea |
| 6,406,672 B1 | 6/2002 | Buhllar et al. |
| 6,432,720 B2 | 8/2002 | Chow |
| 6,438,498 B1 | 8/2002 | Opalsky et al. |
| 6,440,725 B1 | 8/2002 | Pourahmadi et al. |
| 6,448,091 B1 | 9/2002 | Massey et al. |
| 6,451,225 B1 | 9/2002 | Leland et al. |
| 6,468,741 B1 | 10/2002 | Massey et al. |
| 6,475,372 B1 | 11/2002 | Ohara et al. |
| 6,479,233 B1 | 11/2002 | Bard et al. |
| 6,488,896 B2 | 12/2002 | Weigl et al. |
| 6,495,104 B1 | 12/2002 | Unno et al. |
| 6,517,777 B2 | 2/2003 | Liljestrand et al. |
| 6,524,513 B1 | 2/2003 | Pearl et al. |
| 6,524,865 B1 | 2/2003 | Martin et al. |
| 6,534,137 B1 | 3/2003 | Vadhar |
| 6,537,501 B1 | 3/2003 | Holl et al. |
| 6,554,788 B1 | 4/2003 | Hunley et al. |
| 6,559,096 B1 | 5/2003 | Smith et al. |
| 6,613,280 B2 | 9/2003 | Myrick et al. |
| 6,613,286 B2 | 9/2003 | Braun, Sr. et al. |
| 6,613,583 B1 | 9/2003 | Richter et al. |
| 6,635,418 B2 | 10/2003 | Heroux et al. |
| 6,656,428 B1 | 12/2003 | Clark et al. |
| 6,664,104 B2 | 12/2003 | Pourahmadi et al. |
| 6,676,902 B2 | 1/2004 | Baugh et al. |
| 6,699,718 B1 | 3/2004 | Bruegger |
| 6,702,986 B1 | 3/2004 | Leland et al. |
| 6,740,240 B2 | 5/2004 | Coville et al. |
| 6,748,332 B2 | 6/2004 | Chen |
| 6,750,053 B1 | 6/2004 | Widrig Opalsky et al. |
| D494,589 S | 8/2004 | Liljestrand et al. |
| 6,776,965 B2 | 8/2004 | Wyzgol et al. |
| 6,783,736 B1 | 8/2004 | Taylor et al. |
| 6,794,877 B2 | 9/2004 | Blomberg et al. |
| 6,808,939 B2 | 10/2004 | Sigal et al. |
| D499,035 S | 11/2004 | Cook et al. |
| 6,818,185 B1 | 11/2004 | Petersen et al. |
| 6,824,663 B1 | 11/2004 | Boone |
| 6,831,733 B2 | 12/2004 | Pettersson et al. |
| 6,846,629 B2 | 1/2005 | Sigal et al. |
| 6,852,284 B1 | 2/2005 | Holl et al. |
| 6,852,502 B1 | 2/2005 | Martin |
| 6,861,259 B2 | 3/2005 | Columbus |
| 6,866,823 B2 | 3/2005 | Wardlaw |
| 6,869,570 B2 | 3/2005 | Wardlaw |
| 6,878,540 B2 | 4/2005 | Pourahmadi et al. |
| 6,880,384 B2 | 4/2005 | Hvidtfeldt et al. |
| 6,881,536 B1 | 4/2005 | Shah et al. |
| 6,881,541 B2 | 4/2005 | Petersen et al. |
| 6,881,589 B1 | 4/2005 | Leland et al. |
| 6,887,693 B2 | 5/2005 | McMillan et al. |
| 6,893,879 B2 | 5/2005 | Petersen et al. |
| 6,919,173 B2 | 7/2005 | Tsionsky et al. |
| 6,926,834 B2 | 8/2005 | Coville et al. |
| 6,929,953 B1 | 8/2005 | Wardlaw |
| 6,949,377 B2 | 9/2005 | Ho |
| 6,969,450 B2 | 11/2005 | Taniike et al. |
| 6,977,722 B2 | 12/2005 | Wohlstadter et al. |
| D515,220 S | 2/2006 | Miller et al. |
| 7,004,184 B2 | 2/2006 | Handique et al. |
| 7,008,796 B2 | 3/2006 | Wohlstadter et al. |
| 7,011,794 B2 | 3/2006 | Kagan et al. |
| 7,018,353 B2 | 3/2006 | Hunley et al. |
| 7,036,917 B2 | 5/2006 | Müller-Chorus et al. |
| 7,041,206 B2 | 5/2006 | Gephart et al. |
| 7,061,595 B2 | 6/2006 | Cabuz et al. |
| 7,111,503 B2 | 9/2006 | Brumboiu et al. |
| 7,115,421 B2 | 10/2006 | Grzeda et al. |
| 7,135,547 B2 | 11/2006 | Gengrinovitch |
| 7,205,116 B2 | 4/2007 | Salamone et al. |
| 7,235,213 B2 | 6/2007 | Mpock et al. |
| 7,238,246 B2 | 7/2007 | Peters et al. |
| 7,247,488 B2 | 7/2007 | Ghai et al. |
| 7,277,166 B2 | 10/2007 | Padmanabhan et al. |
| 7,282,179 B2 | 10/2007 | Iwaki et al. |
| 7,285,425 B2 | 10/2007 | Shareef et al. |
| 7,288,195 B2 | 10/2007 | Coville et al. |
| 7,299,081 B2 | 11/2007 | Mace et al. |
| 7,306,727 B2 | 12/2007 | Perreault |
| 7,314,711 B2 | 1/2008 | Richter et al. |
| 7,329,538 B2 | 2/2008 | Waieright et al. |
| 7,335,339 B2 | 2/2008 | Berndtsson |
| 7,378,270 B2 | 5/2008 | Azarnia et al. |
| 7,384,409 B2 | 6/2008 | Fischer et al. |
| 7,399,637 B2 | 7/2008 | Wright et al. |
| 7,419,821 B2 | 9/2008 | Davis et al. |
| 7,422,903 B2 | 9/2008 | Conlon et al. |
| 7,422,905 B2 | 9/2008 | Clague et al. |
| 7,438,853 B2 | 10/2008 | Zen et al. |
| 7,439,017 B2 | 10/2008 | Heroux et al. |
| 7,439,069 B2 | 10/2008 | Nippoldt et al. |
| 7,471,394 B2 | 12/2008 | Padmanabhan et al. |
| 7,481,787 B2 | 1/2009 | Gable et al. |
| 7,485,153 B2 | 2/2009 | Padmanabhan et al. |
| 7,494,819 B2 | 2/2009 | Bahatt et al. |
| 7,497,997 B2 | 3/2009 | Glezer et al. |
| 7,521,247 B2 | 4/2009 | De Haan |
| 7,523,649 B2 | 4/2009 | Corey et al. |
| 7,547,384 B2 | 6/2009 | Keenan |
| 7,553,448 B2 | 6/2009 | Kumar et al. |
| 7,553,453 B2 | 6/2009 | Gu et al. |
| 7,569,346 B2 | 8/2009 | Petersen et al. |
| 7,569,393 B2 | 8/2009 | Sin |
| 7,595,169 B2 | 9/2009 | Swaim et al. |
| 7,604,777 B2 | 10/2009 | Columbus |
| 7,608,042 B2 | 10/2009 | Goldberger et al. |
| 7,630,063 B2 | 12/2009 | Padmanabhan et al. |
| 7,641,856 B2 | 1/2010 | Padmanabhan et al. |
| 7,666,355 B2 | 2/2010 | Alavie et al. |
| 7,682,511 B2 | 3/2010 | de Los Reyes et al. |
| 7,682,788 B2 | 3/2010 | Sigal et al. |
| 7,723,099 B2 | 5/2010 | Miller et al. |
| 7,736,901 B2 | 6/2010 | Opalsky et al. |
| 7,767,794 B2 | 8/2010 | Salamone et al. |
| 7,771,658 B2 | 8/2010 | Larsen |
| 7,776,583 B2 | 8/2010 | Billadeau et al. |
| 7,781,226 B2 | 8/2010 | McDevitt et al. |
| 7,816,124 B2 | 10/2010 | Samsoondar |
| 7,820,102 B2 | 10/2010 | Myrick et al. |
| 7,822,510 B2 | 10/2010 | Paik et al. |
| RE41,946 E | 11/2010 | Anderson et al. |
| 7,824,925 B2 | 11/2010 | Wohlstadter et al. |
| 7,833,746 B2 | 11/2010 | Berndtsson et al. |
| 7,838,631 B2 | 11/2010 | Yamashita et al. |
| 7,859,670 B2 | 12/2010 | Kim et al. |
| 7,887,750 B2 | 2/2011 | Blatt et al. |
| 7,888,125 B2 | 2/2011 | Gibbons et al. |
| 7,901,629 B2 | 3/2011 | Calatzis et al. |
| 7,911,617 B2 | 3/2011 | Padmanabhan et al. |
| 7,914,994 B2 | 3/2011 | Petersen et al. |

(56) References Cited

U.S. PATENT DOCUMENTS

| | | |
|---|---|---|
| 7,923,256 B2 | 4/2011 | Widrig Opalsky et al. |
| 7,928,718 B2 | 4/2011 | Larsen |
| 7,932,098 B2 | 4/2011 | Childers et al. |
| 7,939,021 B2 | 5/2011 | Smith et al. |
| 7,952,069 B2 | 5/2011 | Shiokawa et al. |
| 7,977,106 B2 | 7/2011 | Widrig Opalsky et al. |
| 7,978,329 B2 | 7/2011 | Padmanabhan et al. |
| 7,981,362 B2 | 7/2011 | Glezer et al. |
| 7,985,589 B2 | 7/2011 | Garner et al. |
| 8,003,060 B2 | 8/2011 | Cracauer et al. |
| 8,007,670 B2 | 8/2011 | Connors, Jr. |
| 8,008,034 B2 | 8/2011 | Gibbons et al. |
| 8,012,744 B2 | 9/2011 | Gibbons et al. |
| 8,012,745 B2 | 9/2011 | Glezer et al. |
| 8,017,382 B2 | 9/2011 | Davis et al. |
| 8,021,873 B2 | 9/2011 | Johnson et al. |
| 8,028,566 B2 | 10/2011 | Larsen |
| 8,034,296 B2 | 10/2011 | Cox et al. |
| 8,046,175 B2 | 10/2011 | Kuo et al. |
| 8,071,051 B2 | 12/2011 | Padmanabhan et al. |
| 8,101,404 B2 | 1/2012 | Samsoondar |
| 8,101,431 B2 | 1/2012 | McDevitt et al. |
| 8,105,783 B2 | 1/2012 | Handique |
| 8,105,849 B2 | 1/2012 | McDevitt et al. |
| 8,137,626 B2 | 3/2012 | Maltezos et al. |
| 8,236,555 B2 | 8/2012 | Stromgren et al. |
| 8,273,566 B2 | 9/2012 | Billadeau et al. |
| 8,343,526 B2 | 1/2013 | Billadeau et al. |
| 8,394,595 B2 | 3/2013 | Jung et al. |
| 8,394,608 B2 | 3/2013 | Ririe et al. |
| 8,481,901 B2 | 7/2013 | Bedingham et al. |
| 8,585,279 B2 | 11/2013 | Rida |
| 8,623,638 B2 | 1/2014 | Solomon |
| 8,747,779 B2 | 6/2014 | Sprague et al. |
| 8,772,017 B2 | 7/2014 | Battrell et al. |
| 8,778,665 B2 | 7/2014 | Gibbons et al. |
| 8,846,310 B2 | 9/2014 | Johnson et al. |
| 8,870,446 B2 | 10/2014 | Rida |
| 8,895,295 B2 | 11/2014 | Ririe et al. |
| 2002/0019060 A1 | 2/2002 | Petersen et al. |
| 2002/0098116 A1 | 7/2002 | Sugaya et al. |
| 2002/0143297 A1 | 10/2002 | Francavilla et al. |
| 2002/0155033 A1 | 10/2002 | Strand et al. |
| 2003/0029254 A1 | 2/2003 | Hvidtfeldt et al. |
| 2003/0035758 A1 | 2/2003 | Buechler et al. |
| 2003/0052054 A1 | 3/2003 | Pearl et al. |
| 2003/0073089 A1 | 4/2003 | Mauze et al. |
| 2003/0185707 A1 | 10/2003 | Iwaki et al. |
| 2003/0224523 A1 | 12/2003 | Thornberg et al. |
| 2004/0035792 A1 | 2/2004 | Rauch et al. |
| 2004/0086872 A1 | 5/2004 | Childers et al. |
| 2004/0096368 A1 | 5/2004 | Davis et al. |
| 2004/0176704 A1 | 9/2004 | Stevens et al. |
| 2004/0228765 A1 | 11/2004 | Witty et al. |
| 2004/0228766 A1 | 11/2004 | Witty et al. |
| 2004/0248284 A1 | 12/2004 | Van Beuningen |
| 2004/0259268 A1 | 12/2004 | Jacobs et al. |
| 2005/0014279 A1 | 1/2005 | Nguyen et al. |
| 2005/0042137 A1 | 2/2005 | Petersen et al. |
| 2005/0074900 A1 | 4/2005 | Morgan et al. |
| 2005/0181443 A1 | 8/2005 | Sun et al. |
| 2005/0220668 A1 | 10/2005 | Coville |
| 2005/0227370 A1 | 10/2005 | Ramel et al. |
| 2005/0245844 A1 | 11/2005 | Mace et al. |
| 2005/0250173 A1 | 11/2005 | Davis et al. |
| 2006/0094028 A1 | 5/2006 | Danna et al. |
| 2006/0165558 A1 | 7/2006 | Witty et al. |
| 2006/0177347 A1 | 8/2006 | Larsen et al. |
| 2006/0218010 A1 | 9/2006 | Michon et al. |
| 2006/0228259 A1 | 10/2006 | Samsoondar |
| 2006/0257854 A1 | 11/2006 | McDevitt et al. |
| 2006/0257941 A1 | 11/2006 | McDevitt et al. |
| 2006/0257991 A1 | 11/2006 | McDevitt et al. |
| 2006/0263818 A1 | 11/2006 | Scherer et al. |
| 2006/0275841 A1 | 12/2006 | Blankfard et al. |
| 2007/0003434 A1 | 1/2007 | Padmanabhan et al. |
| 2007/0009386 A1 | 1/2007 | Padmanabhan et al. |
| 2007/0031283 A1 | 2/2007 | Davis et al. |
| 2007/0036026 A1 | 2/2007 | Laibinis et al. |
| 2007/0116600 A1 | 5/2007 | Kochar et al. |
| 2007/0166195 A1 | 7/2007 | Padmanabhan et al. |
| 2007/0166196 A1 | 7/2007 | Bardell et al. |
| 2007/0166725 A1 | 7/2007 | McBride et al. |
| 2007/0172388 A1 | 7/2007 | Padmanabhan et al. |
| 2007/0178514 A1 | 8/2007 | Van Beuningen |
| 2007/0178521 A1 | 8/2007 | Sakaino et al. |
| 2007/0248497 A1 | 10/2007 | Robillot |
| 2007/0292941 A1 | 12/2007 | Handique et al. |
| 2008/0021296 A1 | 1/2008 | Creaven |
| 2008/0025872 A1 | 1/2008 | Dykes et al. |
| 2008/0057572 A1 | 3/2008 | Petersen et al. |
| 2008/0131322 A1 | 6/2008 | Kheiri et al. |
| 2008/0149840 A1 | 6/2008 | Handique et al. |
| 2008/0153078 A1 | 6/2008 | Braman et al. |
| 2008/0188732 A1 | 8/2008 | Mace et al. |
| 2008/0227219 A1 | 9/2008 | Gamez |
| 2008/0311002 A1 | 12/2008 | Kirby et al. |
| 2009/0018411 A1 | 1/2009 | Mace et al. |
| 2009/0047713 A1 | 2/2009 | Handique |
| 2009/0065357 A1 | 3/2009 | Glezer et al. |
| 2009/0081078 A1 | 3/2009 | Caramuta |
| 2009/0098541 A1 | 4/2009 | Southern et al. |
| 2009/0130658 A1 | 5/2009 | Barlag et al. |
| 2009/0130719 A1 | 5/2009 | Handique |
| 2009/0148882 A1 | 6/2009 | Goldstein |
| 2009/0151792 A1 | 6/2009 | Noda |
| 2009/0181864 A1 | 7/2009 | Nguyen et al. |
| 2009/0215072 A1 | 8/2009 | McDevitt et al. |
| 2009/0221059 A1 | 9/2009 | Williams et al. |
| 2009/0246076 A1 | 10/2009 | Kumar et al. |
| 2009/0253130 A1 | 10/2009 | Yoo |
| 2009/0311736 A1 | 12/2009 | Ciotti et al. |
| 2009/0325276 A1 | 12/2009 | Battrell et al. |
| 2010/0029011 A1 | 2/2010 | Sin |
| 2010/0081144 A1 | 4/2010 | Holmes et al. |
| 2010/0112723 A1 | 5/2010 | Battrell et al. |
| 2010/0117666 A1 | 5/2010 | Wada et al. |
| 2010/0158756 A1 | 6/2010 | Taylor et al. |
| 2010/0159556 A1 | 6/2010 | Rida |
| 2010/0173394 A1 | 7/2010 | Colston, Jr. et al. |
| 2010/0197522 A1 | 8/2010 | Liu et al. |
| 2010/0203521 A1 | 8/2010 | Klapperich et al. |
| 2010/0203550 A1 | 8/2010 | Miller et al. |
| 2010/0227412 A1 | 9/2010 | Cerda |
| 2010/0240022 A1 | 9/2010 | McNeely |
| 2010/0261292 A1 | 10/2010 | Glezer et al. |
| 2010/0262304 A1 | 10/2010 | Gonnella et al. |
| 2010/0282609 A1 | 11/2010 | Pollack et al. |
| 2010/0285578 A1 | 11/2010 | Selden et al. |
| 2010/0290952 A1 | 11/2010 | Koike et al. |
| 2010/0291588 A1 | 11/2010 | McDevitt et al. |
| 2010/0303722 A1 | 12/2010 | Jin et al. |
| 2011/0008908 A1 | 1/2011 | Biesbrouck |
| 2011/0016691 A1 | 1/2011 | Alden et al. |
| 2011/0039298 A1 | 2/2011 | Berndtsson et al. |
| 2011/0067489 A1 | 3/2011 | Haberstroh et al. |
| 2011/0091357 A1 | 4/2011 | Blatt et al. |
| 2011/0100101 A1 | 5/2011 | Zenhausern et al. |
| 2011/0143378 A1 | 6/2011 | Putnam |
| 2011/0171754 A1 | 7/2011 | Redmond et al. |
| 2011/0192218 A1 | 8/2011 | Miyamura et al. |
| 2011/0192219 A1 | 8/2011 | Miyamura et al. |
| 2011/0194977 A1 | 8/2011 | Miyamura et al. |
| 2011/0195490 A1 | 8/2011 | Kang et al. |
| 2011/0195495 A1 | 8/2011 | Selden et al. |
| 2011/0201909 A1 | 8/2011 | Emery et al. |
| 2011/0203924 A1 | 8/2011 | Wohlstadter et al. |
| 2011/0259091 A1 | 10/2011 | Laubscher et al. |
| 2011/0269159 A1 | 11/2011 | Campbell et al. |
| 2011/0269222 A1 | 11/2011 | Miller et al. |
| 2011/0290669 A1 | 12/2011 | Davis et al. |
| 2011/0294224 A1 | 12/2011 | Liu |
| 2011/0312553 A1 | 12/2011 | Silverbrook et al. |
| 2011/0312661 A1 | 12/2011 | Silverbrook et al. |

(56) References Cited

U.S. PATENT DOCUMENTS

| | | |
|---|---|---|
| 2011/0312742 A1 | 12/2011 | Silverbrook et al. |
| 2011/0318774 A1 | 12/2011 | Larsen |
| 2012/0003730 A1 | 1/2012 | Padmanabhan et al. |
| 2012/0009667 A1 | 1/2012 | Peterson et al. |
| 2012/0034624 A1 | 2/2012 | Miller et al. |
| 2012/0034645 A1 | 2/2012 | Billadeau et al. |
| 2012/0043202 A1 | 2/2012 | Miyamura et al. |
| 2012/0045375 A1 | 2/2012 | Miyamura et al. |
| 2012/0051972 A1 | 3/2012 | Joseph |
| 2012/0053335 A1 | 3/2012 | Liu et al. |
| 2012/0115213 A1 | 5/2012 | Hofstadler et al. |
| 2012/0141337 A1 | 6/2012 | Maltezos et al. |
| 2012/0177537 A1 | 7/2012 | Aota et al. |
| 2012/0190128 A1 | 7/2012 | Nikbakht et al. |
| 2012/0252138 A1 | 10/2012 | Sasso, Jr. et al. |
| 2013/0137172 A1 | 5/2013 | Ririe et al. |
| 2014/0017709 A1 | 1/2014 | Lowe et al. |
| 2014/0186935 A1 | 7/2014 | Yoo |
| 2014/0329301 A1 | 11/2014 | Handique |

FOREIGN PATENT DOCUMENTS

| | | |
|---|---|---|
| EP | 2007905 B1 | 12/2008 |
| EP | 2281631 B1 | 2/2011 |
| EP | 2419217 B1 | 2/2012 |
| GB | 2112293 | 7/1983 |
| JP | 2010-237050 | 10/2010 |
| WO | 8706706 | 11/1987 |
| WO | 9005302 | 5/1990 |
| WO | 9419683 | 9/1994 |
| WO | 9419684 | 9/1994 |
| WO | 9508644 | 3/1995 |
| WO | 9621154 | 7/1996 |
| WO | 9635697 | 11/1996 |
| WO | 9635812 | 11/1996 |
| WO | 9641177 | 12/1996 |
| WO | 9915694 | 4/1999 |
| WO | 2005095954 A1 | 10/2005 |
| WO | 2007002579 A2 | 1/2007 |
| WO | 2007005626 | 1/2007 |
| WO | 2011027092 A1 | 3/2011 |
| WO | 2011113569 | 9/2011 |
| WO | 2012024543 A1 | 2/2012 |
| WO | 2012058632 A1 | 5/2012 |
| WO | 2012136695 A1 | 10/2012 |
| WO | 2013082273 A1 | 6/2013 |
| WO | 2013136115 A1 | 9/2013 |
| WO | 2013173524 A2 | 11/2013 |
| WO | 2013173525 A1 | 11/2013 |
| WO | 2014043388 A1 | 3/2014 |

OTHER PUBLICATIONS

Bertino, et al., "5-Fluorouracil Drug Management: Pharmacokinetics and Pharmacogenomics Workshop Meeting Summary; Orlando, Florida; Jan. 2007", Clinical Colorectal Cancer, vol. 6(6):407-422 (2007).
Bertucci, et al., "The Binding of 5-fluorouracil to Native and Modified Human Serum Albumin: UV, CD, and 1H and 19F NMR Investigation", Journal of Pharmaceutical and Biomedical Analysis, vol. 13:1087-1093 (1995).
Beumer, et al., "A Rapid Nanoparticle Immunoassay to Quantitate 5-Fluorouracil (5-FU) in Plasma", ASCO GI 2008 Meeting (Poster).
Crowley, et al., "Isolation of Plasma from Whole Blood Using Planar Microfilters for Lab-on-a-Chip Applications", Lab Chip, vol. 5(9):922-929 (2005).
Jaffrin, M.Y. (1995). Biological Flows. M.Y. Jaffrin and Colin Caro (Eds.). Plenum Press, New York, pp. 199-226.
Joseph, et al., "Evaluation of Alternatives to Warfarin as Probes for Sudlow Site I of Human Serum Albumin Characterization by High-Performance Affinity Chromatography", J. Chromatogr. A., vol. 1216(16):3492-3500 (2009).
Lukas, et al., "Binding of Digitoxin and Some Related Cardenolides to Human Plasma Proteins", The Journal of Clinical Investigation, vol. 48:1041-1053 (1969).
Madsen, et al., "Cooperative Interaction of Warfarin and Phenylbutazone with Human Serum Albumin", Biochemical Pharmacology, vol. 30(11):1169-1173 (1981).
Means, et al. (1982). Modification of Proteins: Food, Nutritional, and Pharmacological Aspects. Robert E. Feeny and John R. Whitaker (Eds.). American Chemical Society. pp. 325-346.
Olympus UK Ltd—Diagnostics Laboratory News Directory, http://www.labnewsdirectory.co.uk/company/Olympus-UK-Ltd-Diagnostics/2232, (Oct. 1, 2009).
Peters, T., Jr., "Serum Albumin", Adv. Protein Chem., vol. 37:161-246 (1985).
Peyrin, et al., "Characterization of Solute Binding at Human Serum Albumin Site II and its Geometry Using a Biochromatographic Approach", Biophysical Journal, vol. 77:1206-1212 (1999).
Saif, et al. "Pharmacokinetically Guided Doe Adjustment of 5-Fluorouracil: A Rational Approach to Improving Therapeutic Outcomes", J. Natl. Cancer Inst., vol. 101:1543-1552 (2009).
Salamone, et al., "Novel Monoclonal Antibodies for Measuring 5-Fluorouracil Concentrations in Biological Fluids", Journal of Clinical Oncology, 2006 ASCO Annual Meeting Proceedings (Post-Meeting Edition); vol. 24(18S):2055 (2006).
Salamone, et al., "A Multi-Center Evaluation of a Rapid Immunoassay to Quantitate 5-Fluorouracil in Plasma", 2008 HOPA Conference—Anaheim, California (Poster).
Sulkowska, et al., "Competitive Binding of Phenylbutazone and Colchicine to Serum Albumin in Multidrug Therapy: A Spectroscopic Study", Journal of Molecular Structure, vol. 881:97-106 (2008).
Vandelinder, V. and A. Groisman, "Separation of Plasma from Whole Human Blood in a Continuous Cross-Flow in a Molded Microfluidic Device", Anal. Chem., vol. 78:3765-3771 (2006).
Villamor, J. and A. Zatón, "Data Plotting of Warfarin Binding to Human Serum Albumin", J. Biochem. Biophys. Methods, vol. 48:33-41 (2001).
Vos, et al., "Use of the Enzyme-Linked Immunosorbent Assay (ELISA) in Immunotoxicity Testing", Environmental Health Perspectives, vol. 43:115-121 (1982).
Yamashita, et al., "5-Fluorouracil Derivatives with Serum Protein Binding Potencies", Chem. Pharm. Bull., vol. 37 (10):2861-2863 (1989).
Yamashita, et al., "Possible Role of Serum Protein Binding to Improve Drug Disposition", International Journal of Pharmaceutics, vol. 108:241-247 (1994).
Zsila, et al., "Evaluation of Drug-Human Serum Albumin Binding Interactions with Support Vector Machine Aided Online Automated Docking", Bioinformatics, vol. 27(13):1806-1813 (2011).
The International Search Report and the Written Opinion from International PCT Application No. PCT/US2013/041252.
The International Search Report and the Written Opinion from International PCT Application No. PCT/US2013/041255.
The International Search Report and the Written Opinion from International PCT Application No. PCT/US2012/067041.
Restriction Requirement, dated Jul. 2, 2014, from co-pending U.S. Appl. No. 13/844,527.
Response to Jul. 2, 2014 Restriction Requirement, from co-pending U.S. Appl. No. 13/844,527.
Notice of Allowance and Fees Due, dated Oct. 30 2014, from co-pending U.S. Appl. No. 13/844,527.
Notice of Allowance and Fees Due, dated Jan. 9, 2015, from co-pending U.S. Appl. No. 13/844,527.

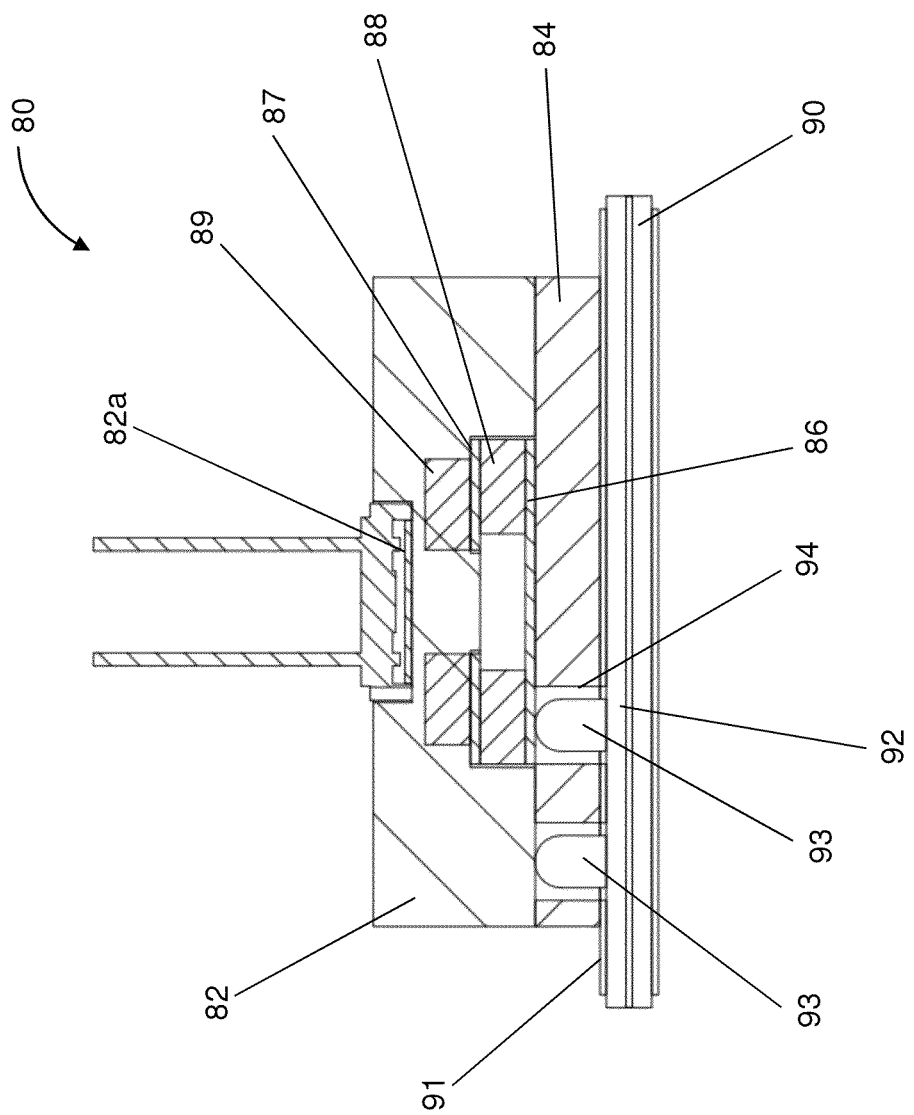

DIAGNOSTIC SYSTEMS AND INSTRUMENTS

This application claims priority to U.S. Provisional Application No. 61/647,272, filed May 15, 2012, and International PCT Application No. PCT/US2012/067041, filed on Nov. 29, 2012, each of which is herein incorporated by reference in its entirety.

FIELD

The present disclosure relates to a clinical diagnostic system. In particular, a clinical diagnostic instrument with a disposable cartridge useful for diagnostic tests in a clinical setting is disclosed.

BACKGROUND

Clinical laboratory testing requires instruments and tests with high accuracy and precision. Containing costs for lab tests is also important. Some clinical lab tests are conducted in high volume because of the large number of patients undergoing tests. There are drawbacks associated with present procedures that require sequential and additional steps and transfers of multiple reagents to produce the assay. Each additional step for a detection assay increases the degree of difficulty for execution and may even increase chances of contamination or error by the operator and is prone to misuse, thereby, resulting in a higher margin for error. Thus, it is desirable to have a clinical diagnostic instrument that can reduce the undesirable processing steps of transferring samples to labs and instead complete a diagnostic test in a physician's office or at a patient's bedside. Such an instrument would inevitably reduce processing costs and cut down on opportunity for error and contamination.

SUMMARY

The disclosure relates generally to a clinical diagnostic system. In particular, a clinical diagnostic instrument with a disposable cartridge useful for diagnostic tests in a clinical setting is disclosed.

In one embodiment, the disclosure relates generally to a diagnostic system having a closed fluidic pathway comprising a diagnostic instrument comprising at least two probes; a fluidic pathway; a non-electrochemiluminescence (ECL) detection system; an ECL detection system; and a pump; and a cartridge comprising at least one needle, at least one reservoir; at least one fluidic seal; and at least one fluidic channel; and a blood collection tube, the closed fluidic pathway, wherein the pathway begins and ends in the cartridge and has a substantially single direction of flow in a pathway fluidically connecting the diagnostic instrument and the cartridge.

In some embodiments, the disclosure relates generally to a diagnostic system having a closed fluidic pathway, wherein the at least one probe comprises a first probe and a waste probe, and wherein the closed fluidic pathway includes a first probe engagement with the cartridge and a waste probe engagement with the cartridge.

In some embodiments, the disclosure relates generally to a diagnostic system having a closed fluidic pathway, wherein the at least one reservoir comprises a first reservoir and a waste reservoir.

In some embodiments, the disclosure relates generally to a diagnostic system having a closed fluidic pathway, wherein the first reservoir and the waste reservoir are the same reservoir.

In some embodiments, the disclosure relates generally to a diagnostic system having a closed fluidic pathway, wherein the first reservoir and the waste reservoir are not the same reservoir.

In some embodiments, the disclosure relates generally to a diagnostic system having a closed fluidic pathway, wherein after the first reservoir is emptied, the first reservoir is used as the waste reservoir.

In some embodiments, the disclosure relates generally to a diagnostic system having a closed fluidic pathway, wherein after the first reservoir is emptied it becomes the waste reservoir.

In some embodiments, the disclosure relates generally to a diagnostic system having a closed fluidic pathway, wherein the first probe fluidically connects to a first reservoir of the disposable cartridge.

In some embodiments, the disclosure relates generally to a diagnostic system having a closed fluidic pathway, wherein the first reservoir contains diagnostic reagents.

In some embodiments, the disclosure relates generally to a diagnostic system having a closed fluidic pathway, wherein the waste probe fluidically connects to a waste reservoir of the disposable cartridge.

In some embodiments, the disclosure relates generally to a diagnostic system having a closed fluidic pathway, wherein the waste reservoir receives waste materials.

In some embodiments, the disclosure relates generally to a diagnostic system having a closed fluidic pathway, wherein waste materials include at least one of a processed reagent, a blood filtrate, and a processed plasma.

In some embodiments, the disclosure relates generally to a diagnostic system having a closed fluidic pathway, wherein the fluidic pathway has a diameter that is the same as a diameter of the at least one probe.

In some embodiments, the disclosure relates generally to a diagnostic system having a closed fluidic pathway, wherein the substantially single direction of flow reduces the potential for carryover between diagnostic tests such that there is substantially no detectable carryover between diagnostic tests.

In some embodiments, the disclosure relates generally to a diagnostic system having a closed fluidic pathway, wherein the substantially single direction of flow prevents carryover between different cartridges used with the diagnostic system such that there is substantially no detectable carryover between diagnostic tests.

In some embodiments, the disclosure relates generally to a diagnostic system having a closed fluidic pathway, wherein a fluid flows, in order, from a first reservoir to a first probe, to the non-ECL detection system, to the ECL detection system, through the pump, to a waste probe, and to a waste reservoir, each fluidically connected by the fluidic pathway.

In some embodiments, the disclosure relates generally to a diagnostic system having a closed fluidic pathway, wherein at least one reagent and at least one waste material are stored on the cartridge.

In some embodiments, the disclosure relates generally to a diagnostic system having a closed fluidic pathway, wherein at least one reagent and at least one waste material are stored on the cartridge and not in the diagnostic instrument.

In some embodiments, the disclosure relates generally to a diagnostic system having a closed fluidic pathway, further comprising a motion assembly.

In some embodiments, the disclosure relates generally to a diagnostic system having a closed fluidic pathway, wherein the motion assembly has two axes mechanically connected to the first probe and the waste probe.

In some embodiments, the disclosure relates generally to a diagnostic system having a closed fluidic pathway, wherein no sample is stored on the diagnostic instrument.

In some embodiments, the disclosure relates generally to a diagnostic system having a closed fluidic pathway, wherein no fluids are stored on the diagnostic instrument.

In some embodiments, the disclosure relates generally to a diagnostic system having a closed fluidic pathway, wherein no dry reagents are stored on the diagnostic instrument.

In some embodiments, the disclosure relates generally to a diagnostic system having a closed fluidic pathway, wherein all fluids are stored on the cartridge.

In some embodiments, the disclosure relates generally to a diagnostic system having a closed fluidic pathway, wherein all dry reagents are stored on the cartridge.

In another embodiment, the present disclosure relates generally to a diagnostic system having a closed fluidic pathway comprising a diagnostic instrument having a set of fluidic control elements comprising a non-electrochemiluminescence (ECL) detection system; a first probe fluidically connected to the non-ECL detection system by at least one fluidic tube; an ECL detection system fluidically connected to the non-ECL detection system by at least one fluidic tube; a pump fluidically connected to the ECL detection system by at least one fluidic tube and fluidically connected to a waste probe by at least one fluidic tube; and a motion assembly having two axes mechanically connected to the first and waste probes; and a cartridge having at least one needle, at least one reservoir; at least one fluidic seal; and at least one fluidic channel, wherein the closed fluidic pathway has a substantially single direction of flow in a pathway fluidically connecting the diagnostic instrument and the disposable cartridge.

In some embodiments, the present disclosure relates generally to a diagnostic system having a closed fluidic pathway, wherein the at least one reservoir comprises a first reservoir and a waste reservoir.

In some embodiments, the present disclosure relates generally to a diagnostic system having a closed fluidic pathway, wherein the first reservoir and the waste reservoir are the same reservoir.

In some embodiments, the present disclosure relates generally to a diagnostic system having a closed fluidic pathway, wherein the first reservoir and the waste reservoir are not the same reservoir.

In some embodiments, the present disclosure relates generally to a diagnostic system having a closed fluidic pathway, wherein after the first reservoir is emptied, the first reservoir is used as the waste reservoir.

In some embodiments, the present disclosure relates generally to a diagnostic system having a closed fluidic pathway, wherein after the first reservoir is emptied it becomes the waste reservoir.

In some embodiments, the present disclosure relates generally to a diagnostic system having a closed fluidic pathway, wherein the first probe fluidically connects to a first reservoir of the disposable cartridge.

In some embodiments, the present disclosure relates generally to a diagnostic system having a closed fluidic pathway, wherein the first reservoir contains diagnostic reagents.

In some embodiments, the present disclosure relates generally to a diagnostic system having a closed fluidic pathway, wherein the waste probe fluidically connects to a waste reservoir of the disposable cartridge.

In some embodiments, the present disclosure relates generally to a diagnostic system having a closed fluidic pathway, wherein the waste reservoir receives waste materials.

In some embodiments, the present disclosure relates generally to a diagnostic system having a closed fluidic pathway, wherein waste materials include at least one of a processed reagent, a blood filtrate, and a processed plasma.

In some embodiments, the present disclosure relates generally to a diagnostic system having a closed fluidic pathway, wherein the fluidic pathway has a diameter that is the same as a diameter of at least one probe.

In some embodiments, the present disclosure relates generally to a diagnostic system having a closed fluidic pathway, wherein the substantially single direction of flow reduces the potential for carryover between diagnostic tests such that there is substantially no detectable carryover between diagnostic tests.

In some embodiments, the present disclosure relates generally to a diagnostic system having a closed fluidic pathway, wherein the substantially single direction of flow prevents carryover between different cartridges used with the diagnostic system such that there is substantially no detectable carryover between diagnostic tests.

In some embodiments, the present disclosure relates generally to a diagnostic system having a closed fluidic pathway, wherein a fluid flows, in order, from a first reservoir to a first probe, to the non-ECL detection system, to the ECL detection system, through the pump, to a waste probe, and to a waste reservoir, each fluidically connected by the fluidic pathway.

In some embodiments, the present disclosure relates generally to a diagnostic system having a closed fluidic pathway, wherein at least one reagent and at least one waste material are stored on the cartridge and not in the diagnostic instrument.

In some embodiments, the present disclosure relates generally to a diagnostic system having a closed fluidic pathway, further comprising a motion assembly.

In some embodiments, the present disclosure relates generally to a diagnostic system having a closed fluidic pathway, wherein the motion assembly has two axes mechanically connected to the first probe and the waste probe.

In some embodiments, the present disclosure relates generally to a diagnostic system having a closed fluidic pathway, wherein no sample is stored on the diagnostic instrument.

In some embodiments, the present disclosure relates generally to a diagnostic system having a closed fluidic pathway, wherein no fluids are stored on the diagnostic instrument.

In some embodiments, the present disclosure relates generally to a diagnostic system having a closed fluidic pathway, wherein no dry reagents are stored on the diagnostic instrument.

In some embodiments, the present disclosure relates generally to a diagnostic system having a closed fluidic pathway, wherein all fluids are stored on the cartridge.

In some embodiments, the present disclosure relates generally to a diagnostic system having a closed fluidic pathway, wherein all dry reagents are stored on the cartridge.

In one embodiment, the present disclosure relates generally to a diagnostic system having a closed fluidic pathway comprising a diagnostic instrument having a set of fluidic control elements comprising a non-ECL detection system; a first probe fluidically connected to the non-ECL detection system by at least one fluidic tube; a pump fluidically connected to the ECL detection system by at least one fluidic tube and fluidically connected to a waste probe by at least one fluidic tube; and a cartridge having at least one needle, at least one reservoir; at least one fluidic seal; and at least one fluidic channel, wherein the closed fluidic pathway has a substantially single direction of flow in a pathway fluidically connecting the diagnostic instrument and the disposable cartridge.

In some embodiments, the present disclosure relates generally to a diagnostic system having a closed fluidic pathway, wherein the non-ECL detection system is fluidically connected to the first probe by at least one fluidic tube and fluidically connected to the ECL detection system by at least one fluidic tube.

In some embodiments, the present disclosure relates generally to a diagnostic system having a closed fluidic pathway, wherein the at least one reservoir comprises a first reservoir and a waste reservoir.

In some embodiments, the present disclosure relates generally to a diagnostic system having a closed fluidic pathway, wherein the first reservoir and the waste reservoir are the same reservoir.

In some embodiments, the present disclosure relates generally to a diagnostic system having a closed fluidic pathway, wherein the first reservoir and the waste reservoir are not the same reservoir.

In some embodiments, the present disclosure relates generally to a diagnostic system having a closed fluidic pathway, wherein the first probe fluidically connects to a first reservoir of the disposable cartridge.

In some embodiments, the present disclosure relates generally to a diagnostic system having a closed fluidic pathway, wherein the first reservoir contains diagnostic reagents.

In some embodiments, the present disclosure relates generally to a diagnostic system having a closed fluidic pathway, wherein the waste probe fluidically connects to a waste reservoir of the disposable cartridge.

In some embodiments, the present disclosure relates generally to a diagnostic system having a closed fluidic pathway, wherein the waste reservoir receives waste materials.

In some embodiments, the present disclosure relates generally to a diagnostic system having a closed fluidic pathway, wherein waste materials include at least one of a processed reagent, a blood filtrate, and a processed plasma.

In some embodiments, the present disclosure relates generally to a diagnostic system having a closed fluidic pathway, wherein the fluidic pathway has a diameter that is the same as a diameter of the at least one probe.

In some embodiments, the present disclosure relates generally to a diagnostic system having a closed fluidic pathway, wherein the substantially single direction of flow reduces the potential for carryover between diagnostic tests such that there is substantially no detectable carryover between diagnostic tests.

In some embodiments, the present disclosure relates generally to a diagnostic system having a closed fluidic pathway, wherein the substantially single direction of flow prevents carryover between different cartridges used with the diagnostic system such that there is substantially no detectable carryover between diagnostic tests.

In some embodiments, the present disclosure relates generally to a diagnostic system having a closed fluidic pathway, wherein a fluid flows, in order, from a first reservoir to a first probe, to the non-ECL detection system, to the ECL detection system, through the pump, to a waste probe, and to a waste reservoir, each fluidically connected by the fluidic pathway.

In some embodiments, the present disclosure relates generally to a diagnostic system having a closed fluidic pathway, wherein at least one reagent and at least one waste material are stored on the cartridge and not in the diagnostic instrument.

In some embodiments, the present disclosure relates generally to a diagnostic system having a closed fluidic pathway, further comprising a motion assembly.

In some embodiments, the present disclosure relates generally to a diagnostic system having a closed fluidic pathway, wherein the motion assembly has two axes mechanically connected to the first probe and the waste probe.

In some embodiments, the present disclosure relates generally to a diagnostic system having a closed fluidic pathway, wherein all fluids are stored on the cartridge.

In some embodiments, the present disclosure relates generally to a diagnostic system having a closed fluidic pathway, wherein all dry reagents are stored on the cartridge.

In still another embodiment, the present disclosure relates generally to a method of temperature control within a diagnostic system comprising measuring with a sensor a starting temperature of a cartridge containing a biological sample and at least one reagent; comparing the starting temperature of the cartridge to a target temperature; heating with a heater the cartridge to the target temperature; and maintaining the target temperature using a closed loop control for a period of time.

In some embodiments, the present disclosure relates generally to a method of temperature control within a diagnostic system, wherein measuring the starting temperature comprises measuring with a sensor the rate of an incubator's temperature loss after the cartridge is placed on the incubator.

In some embodiments, the present disclosure relates generally to a method of temperature control within a diagnostic system, wherein measuring the starting temperature comprises measuring with a sensor the rate of an incubator plate's temperature loss after the cartridge is placed on the incubator plate.

In some embodiments, the present disclosure relates generally to a method of temperature control within a diagnostic system, wherein the same sensor is used to measure the starting temperature and in the closed loop control to maintain the target temperature.

In some embodiments, the present disclosure relates generally to a method of temperature control within a diagnostic system, wherein the rate of temperature loss is related to the rate that heat transfers from the incubator plate to the cartridge, and the starting temperature of the cartridge.

In some embodiments, the present disclosure relates generally to a method of temperature control within a diagnostic system, wherein the sensor is integral with the incubator plate.

In some embodiments, the present disclosure relates generally to a method of temperature control within a diagnostic system, wherein the heater is integral with the incubator plate.

In some embodiments, the present disclosure relates generally to a method of temperature control within a diagnostic system, wherein the temperature control is a closed-loop feedback control.

In some embodiments, the present disclosure relates generally to a method of temperature control within a diagnostic system, wherein maintaining the target temperature using a closed loop control comprises intermittently measuring with the sensor the temperature of the cartridge during operation of the diagnostic system; comparing the cartridge temperature to the target temperature; and heating with the heater the cartridge to the target temperature.

In some embodiments, the present disclosure relates generally to a method of temperature control within a diagnostic system, wherein the period of time is equal to or less than the time it takes for the diagnostic system to complete a full diagnostic test.

In some embodiments, the present disclosure relates generally to a method of temperature control within a diagnostic system, wherein the same sensor is used to measure the starting temperature and in the closed loop control to maintain the target temperature.

In some embodiments, the present disclosure relates generally to a method of temperature control within a diagnostic system, wherein the rate of temperature loss is related to the rate that heat transfers from the incubator plate to the cartridge, and the starting temperature of the cartridge.

In some embodiments, the present disclosure relates generally to a method of temperature control within a diagnostic system, wherein the sensor is integral with the incubator plate.

In some embodiments, the present disclosure relates generally to a method of temperature control within a diagnostic system, wherein the heater is integral with the incubator plate.

In still another embodiment, the present disclosure relates generally to a method of temperature control within a diagnostic system having a multi-zone incubator, comprising in a first zone of an incubator (or on an incubator plate), measuring with a first sensor a starting temperature of a portion of a cartridge containing a biological sample and at least one reagent, wherein the cartridge is shorter in length than the length of the incubator and the portion of the cartridge only contacts the first zone of the incubator; comparing the starting temperature of the portion of the cartridge to a first target temperature; heating with a first heater the portion of the cartridge to the first target temperature; maintaining the first target temperature of a portion of the cartridge using a closed loop control for a period of time; and in a second zone of the incubator (or on the incubator plate), measuring with a second sensor a starting temperature of a second portion of a cartridge containing a biological sample and at least one reagent, wherein the second portion of the cartridge only contacts the second zone of the incubator; comparing the starting temperature of the second portion of the cartridge to a second target temperature; heating with a second heater the second portion of the cartridge to the second target temperature; and maintaining the target temperature of the second portion of the cartridge using a second closed loop control for a period of time.

In some embodiments, the present disclosure relates generally to a method of temperature control within a diagnostic system having a multi-zone incubator, wherein the first and second zones of the multi-zone incubator operate independently of one another.

In some embodiments, the present disclosure relates generally to a method of temperature control within a diagnostic system having a multi-zone incubator, wherein the measurements in the first and second zones occur simultaneously during operation of the diagnostic system.

In some embodiments, the present disclosure relates generally to a method of temperature control within a diagnostic system having a multi-zone incubator, wherein the measurements in the first and second zones occur at different times during operation of the diagnostic system.

In some embodiments, the present disclosure relates generally to a method of temperature control within a diagnostic system having a multi-zone incubator, wherein the first target temperature and the second target temperature are different.

In some embodiments, the present disclosure relates generally to a method of temperature control within a diagnostic system having a multi-zone incubator, wherein the first target temperature and the second target temperature are the same.

In some embodiments, the present disclosure relates generally to a method of temperature control within a diagnostic system having a multi-zone incubator, wherein the first sensor and the second sensor are different.

In some embodiments, the present disclosure relates generally to a method of temperature control within a diagnostic system having a multi-zone incubator, wherein the first heater and the second heater are different.

In some embodiments, the present disclosure relates generally to a method of temperature control within a diagnostic system having a multi-zone incubator, wherein the period of time is equal to or less than the time it takes for the diagnostic system to complete a full diagnostic test.

In yet another embodiment, the present disclosure relates generally to an apparatus for measuring bead recovery, comprising a housing; a tubing assembly in fluidic communication with an ECL detection system a fluorescence excitation source; a light detector for fluorescence, wherein the fluorescence excitation source transmits light that reflects off of fluorescent beads in the sample flowing through the tubing assembly and the light detector measures the amount of light reflected.

In yet another embodiment, the present disclosure relates generally to a non-ECL, non-contact method of detecting and measuring bead recovery, if any, during the processing of a cartridge, comprising illuminating with a light source a processed sample flowing through a fluidic pathway; wherein the sample contains fluorescent and non-fluorescent beads and the laser light source is a laser with a specific wavelength; detecting with a first photodiode a transmitted laser light originating from the tubing assembly carrying the fluorescent beads; detecting with a second photodiode a reflected laser-induced fluorescent light emitted by the fluorescent beads travelling through the tubing assembly; converting the transmitted laser light and the reflected laser-induced fluorescent light into measurable electrical signals; processing the electrical signals to calculate an internal standard which is directly related to the amount of fluorescent beads traveling through the tubing assembly; and comparing a magnitude of signal to a predicted magnitude based on a known amount of fluorescent and non-fluorescent beads within the sample.

In yet another embodiment, the present disclosure relates generally to a fluorescence based, non-interfering method of measuring ECL bead recovery, if any, after assay construction on a clinical diagnostic instrument, comprising illuminating with a light source a sample flowing through a tubing assembly, wherein the sample contains fluorescent beads and ECL beads; measuring fluorescence; and processing the fluorescence signal to calculate ECL bead recovery by comparing the fluorescence signal to a fluorescence signal from a standardized quantity of fluorescent beads.

In yet another embodiment, the present disclosure relates generally to an assay composition comprising a mixture of at least one of a fluorescent labeled bead and at least one of an ECL labeled bead.

In some embodiments, the present disclosure relates generally an assay composition, wherein beads can be both fluorescently labeled and ECL labeled.

In yet another embodiment, the present disclosure relates generally to a method of measuring backlash of a pump in a diagnostic system, comprising measuring the amount of backlash volume present in a pump through pressure changes; processing the pressure measurement data into a backlash amount; and adjusting the desired pump volume to compensate for the backlash amount measured.

In some embodiments, the disclosure relates generally to a method of measuring backlash of a pump in a diagnostic system, wherein the backlash measurement data is stored and saved by a diagnostic instrument of the diagnostic system to be used repeatedly through cartridge processing cycles of the diagnostic system, wherein the stored data increases efficiency of the diagnostic instrument for future uses.

In some embodiments, the disclosure relates generally to a method of measuring backlash of a pump in a diagnostic system, wherein the backlash is measured on a pump with a pressure sensor.

In some embodiments, the disclosure relates generally to a method of measuring backlash of a pump in a diagnostic system, wherein the pump is a piston and cylinder pump.

In some embodiments, the disclosure relates generally to a method of measuring backlash of a pump in a diagnostic system, wherein the pump is a motor driven piston and cylinder pump.

In some embodiments, the disclosure relates generally to a method of measuring backlash of a pump in a diagnostic system, wherein where the pump is a motor driven piston and cylinder pump with a pressure sensor.

In some embodiments, the disclosure relates generally to a method of measuring backlash of a pump in a diagnostic system, wherein the pump is a motor driven piston and cylinder pump with a pressure sensor and with a small flat.

In some embodiments, the disclosure relates generally to a method of measuring backlash of a pump in a diagnostic system, wherein the pump is a close fitting ceramic piston and cylinder pump.

In some embodiments, the disclosure relates generally to a method of measuring backlash of a pump in a diagnostic system, wherein the pump is an IVEK pump.

In some embodiments, the disclosure relates generally to a method of measuring backlash of a pump in a diagnostic system, wherein the pump piston has a small flat.

In yet another embodiment, the present disclosure relates generally to a method to improve pump accuracy, comprising measuring for an amount of backlash present in a pump; and compensating subsequent pump displacements by the backlash, by positioning a piston in a chamber of the pump such that the chamber is not connected to any inlet or outlet ports; moving the piston using a piston motor by a predetermined distance and rate so as to build up pressure or vacuum; reversing the piston motor direction using the same or different predetermined distance and rate while measuring pressure or vacuum; deriving backlash volume by measuring the time duration that the pressure or vacuum level did not respond to the reversed piston motor movement; and multiplying the time duration by piston motor rate to calculate backlash volume.

In some embodiments, the present disclosure relates generally to a method to improve pump accuracy, wherein the chamber is isolated such that when the piston is moved by the piston motor the chamber can build up pressure or build up a vacuum.

In yet another embodiment, the present disclosure relates generally to a method to improve pump accuracy, comprising measuring for the amount of backlash present in a pump and then compensating subsequent pump displacements by the backlash by positioning a piston in the chamber of the pump such that the chamber is not connected to any inlet or outlet ports; moving the piston using a piston motor until a predetermined pressure level is reached; reversing the piston motor direction and measuring pressure or vacuum; deriving backlash volume by measuring the time duration that the pressure or vacuum level did not respond to the reversed piston motor movement, and multiplying the time duration by piston motor rate to calculate backlash volume.

In some embodiments, the present disclosure relates generally to a method to improve pump accuracy, wherein the pump is a piston and cylinder pump.

In some embodiments, the present disclosure relates generally to a method to improve pump accuracy, wherein the pump is a motor driven piston and cylinder pump.

In some embodiments, the present disclosure relates generally to a method to improve pump accuracy, wherein where the pump is a motor driven piston and cylinder pump with a pressure sensor.

In some embodiments, the present disclosure relates generally to a method to improve pump accuracy, wherein the pump is a motor driven piston and cylinder pump with pressure sensor and with a small flat.

In some embodiments, the present disclosure relates generally to a method to improve pump accuracy, wherein the pump is a close fitting ceramic piston and cylinder pump.

In some embodiments, the present disclosure relates generally to a method to improve pump accuracy, wherein the pump is an IVEK pump.

In some embodiments, the present disclosure relates generally to a method to improve pump accuracy, wherein the pump piston has a small flat.

In some embodiments, the present disclosure relates generally to a method to improve pump accuracy, wherein the pump has a dual action with linear and rotational motion.

In still another embodiment, the present disclosure relates generally to a method of increasing time efficiency of a pump used in a diagnostic system, comprising measuring the amount of backlash volume present in the pump through pressure changes; processing the pressure measurement data into a backlash amount; adjusting the desired pump volume to compensate for the backlash amount measured; and reducing processing time of the pump based on adjustments of pump volume.

In still another embodiment, the present disclosure relates generally to a method of use of a composition useful for lubricating a fluidic pump system of a diagnostic system comprising glycol, the method comprising flushing the pump immediately after use with the composition such that during periods of non-use of the pump remains primed for operation.

In some embodiments, the present disclosure relates generally to a method of use of a composition useful for lubricating a fluidic pump system of a diagnostic system, wherein the composition further comprises glycerine.

In some embodiments, the present disclosure relates generally to a method of use of a composition useful for lubricating a fluidic pump system of a diagnostic system, wherein the glycol is diethylene glycol.

In some embodiments, the present disclosure relates generally to a method of use of a composition useful for lubricating a fluidic pump system of a diagnostic system, wherein the glycol is at least one of ethylene glycol, triethylene glycol, tetraethylene glycol, and polyethylene.

In some embodiments, the present disclosure relates generally to a method of use of a composition useful for lubricating a fluidic pump system of a diagnostic system, wherein the composition further comprises an anti-microbial agent.

In some embodiments, the present disclosure relates generally to a method of use of a composition useful for lubricating a fluidic pump system of a diagnostic system, wherein the composition further comprises water.

In some embodiments, the present disclosure relates generally to a method of use of a composition useful for lubricating a fluidic pump system of a diagnostic system, wherein the composition is a lubricant for the pump.

In some embodiments, the present disclosure relates generally to a method of use of a composition useful for lubricating a fluidic pump system of a diagnostic system, wherein the composition is a non-volatile liquid.

In some embodiments, the present disclosure relates generally to a method of use of a composition useful for lubricating a fluidic pump system of a diagnostic system, wherein the composition inhibits solid formation between a piston and a cylinder of the pump.

In still another embodiment, the present disclosure relates generally to a composition useful for lubricating a fluidic pump system of a diagnostic system, comprising glycol.

In still another embodiment, the present disclosure relates generally to a composition useful for lubricating a fluidic pump system of a diagnostic system, comprising glycol and glycerine.

In still another embodiment, the present disclosure relates generally to a composition useful for preventing freezing or seizing or stiction of a pump system during periods of non-use of a pump, comprising at least one of the following properties: liquid at the operating temperature; low vapor pressure; water soluble; solvent for residual salts or other solids within the pump dead volume; low surface tension; low viscosity; chemically stable when inside pump or stored in intermediate containers; does not react with fluids for decontamination; chemically compatible with exposed materials; and does not interfere with adjacent operations.

In still another embodiment, the present disclosure relates generally to a method of preventing freezing or seizing or stiction during periods of non-use of a pump, comprising circulating a composition comprising glycol through a pump system.

In some embodiments, the present disclosure relates generally to a method of preventing freezing or seizing or stiction during periods of non-use of a pump, wherein the composition is stored until use on a cartridge that is fluidically connected to the pump system.

In some embodiments, the present disclosure relates generally to a method of preventing freezing or seizing or stiction during periods of non-use of a pump, wherein the composition is returned to the cartridge after it circulates through the pump system.

In some embodiments, the present disclosure relates generally to a method of preventing freezing or seizing or stiction during periods of non-use of a pump, wherein less than about 2.0 nL of the composition is required to protect pump during periods of non-use.

In some embodiments, the present disclosure relates generally to a method of preventing freezing or seizing or stiction during periods of non-use of a pump, wherein less than about 1.5 nL of the composition is required to protect pump during periods of non-use.

In some embodiments, the present disclosure relates generally to a method of preventing freezing or seizing or stiction during periods of non-use of a pump, wherein less than about 1.0 nL of the composition is required to protect pump during periods of non-use.

In some embodiments, the present disclosure relates generally to a method of preventing freezing or seizing or stiction during periods of non-use of a pump, wherein about 1.0 nL of the composition is required to protect pump during periods of non-use.

In still another embodiment, the present disclosure relates generally to an electrochemiluminescence (ECL) detection system, comprising an ECL detection module comprising an enclosure having a top and a base, wherein the surface of the base is flat and forms a working surface, and the top is attached to the base which acts as the bottom of the enclosure thereby forming a cavity of a height; a first electrode and a second electrode stacked and separated by a first gasket, wherein the base supports the first electrode and wherein the first gasket has a compressible thickness that creates a predetermined separation gap between the first and second electrodes; a transparent window formed out of the second electrode to facilitate ECL detection; and a printed circuit board, wherein the printed circuit board is positioned next to the base, electrically connecting components within the ECL detection system.

In still another embodiment, the present disclosure relates generally to an electrochemiluminescence (ECL) detection system, comprising an ECL detection module comprising an enclosure having a top and a base, wherein the surface of the base is flat and forms a working surface, and the top is attached to the base which acts as the bottom of the enclosure thereby forming a cavity of a height; a first electrode and a second electrode stacked and separated by a first gasket, wherein the base supports the first electrode and wherein the first gasket has a thickness that creates a precise predetermined separation gap between the first and second electrodes; a transparent window formed out of the second electrode to facilitate ECL detection; a second gasket fluidically sealing the enclosure and having a differential compliance less than the first gasket to maintain the electrode separation gap; and a printed circuit board positioned next to the base, electrically connecting components within the ECL detection system.

In still another embodiment, the present disclosure relates generally to an electrochemiluminescence (ECL) detection system, comprising an ECL detection module comprising an enclosure having a top and a base, wherein the surface of the base is flat and forms a working surface, and the top is attached to the base which acts as the bottom of the enclosure thereby forming a cavity of a precise height; a measurement containment area bounded by a first electrode surface, a second electrode surface and a first gasket cutout, wherein the first electrode and the second electrode are stacked and separated by the first gasket, and wherein the base supports the first electrode, the first gasket has a compressible thickness, and the electrode/gasket stack resides in the cavity to create a precise predetermined separation gap between the first and second electrode surfaces; a transparent window in at least one cutout of the second electrode to facilitate ECL detection, wherein at least one inlet port and at least one outlet port in the at least one cutout of the second electrode transport fluids in and out of the measurement containment area; and an opaque enclosure surrounding the ECL module to exclude ambient light.

In some embodiments, the present disclosure relates generally to an electrochemiluminescence (ECL) detection system, wherein the measurement containment area is sealed without using adhesives.

In some embodiments, the present disclosure relates generally to an electrochemiluminescence (ECL) detection system, wherein the measurement containment area is sealed using two or more gaskets.

In some embodiments, the present disclosure relates generally to an electrochemiluminescence (ECL) detection system, wherein using two or more gaskets more compliant than the first gasket maintains the first and second electrode spacing height.

In some embodiments, the present disclosure relates generally to an electrochemiluminescence (ECL) detection system, wherein the measurement containment area is made precise and accurate by compensating for the clamped distortion of the gasket in the unclamped gasket cutouts.

In some embodiments, the present disclosure relates generally to an electrochemiluminescence (ECL) detection system, wherein the measurement containment area is made precise and accurate by compensating for the gasket raw material thickness variation in the unclamped gasket cutouts.

In some embodiments, the present disclosure relates generally to an electrochemiluminescence (ECL) detection system, wherein ambient light leakage is blocked with an opaque printed circuit board.

In some embodiments, the present disclosure relates generally to an electrochemiluminescence (ECL) detection system, wherein ambient light leakage is blocked with a printed circuit board made opaque with one or more opaque coatings.

In some embodiments, the present disclosure relates generally to an electrochemiluminescence (ECL) detection system, wherein ambient light leakage is blocked with a printed circuit board made opaque with one or more internal or external metal foil layers.

In still another embodiment, the present disclosure relates generally to a method of identifying a cartridge for use in a diagnostic system, comprising scanning for a first time a scannable code on a cartridge, wherein the scannable code contains data on at least one of a test protocol for the cartridge, a patient information, a lot number for the cartridge contents, a serial number for the cartridge, an expiration date for the cartridge; inserting the cartridge into a diagnostic instrument; scanning for a second time the scannable code on the cartridge while inside the diagnostic instrument; comparing the data between the scans to ensure that the correct cartridge was inserted into the diagnostic instrument; providing feedback to a user on whether the correct cartridge was inserted into the diagnostic instrument.

In some embodiments, the present disclosure relates generally to a method of identifying a cartridge for use in a diagnostic system, wherein the first scan of the scannable code is scanned by an external scannable code scanner.

In some embodiments, the present disclosure relates generally to a method of identifying a cartridge for use in a diagnostic system wherein the scannable code contains data on all of a test protocol for the cartridge, a patient information, a lot number for the cartridge contents, a serial number for the cartridge, and an expiration date for the cartridge.

In still another embodiment, the present disclosure relates generally to a method of identifying a cartridge for use in a diagnostic system, comprising scanning a scannable code on a cartridge, wherein the scannable code contains data on at least one of a test protocol for the cartridge, a patient information, a lot number for the cartridge contents, a serial number for the cartridge, an expiration date for the cartridge; inserting the cartridge into a diagnostic instrument; processing the data from the scanned scannable code to ensure that the correct cartridge was inserted into the diagnostic instrument; and providing feedback to a user on whether the correct cartridge was inserted into the diagnostic instrument.

In some embodiments, the present disclosure relates generally to a method of identifying a cartridge for use in a diagnostic system, further comprising scanning the scannable code on the cartridge while inside the diagnostic instrument with an internal scanner; and comparing the data between the scans to ensure that the correct cartridge was inserted into the diagnostic instrument.

In some embodiments, the present disclosure relates generally to a method of identifying a cartridge for use in a diagnostic system, wherein the first scan of the scannable code is scanned by an external scannable code scanner (on the exterior of the diagnostic instrument).

In still another embodiment, the present disclosure relates generally to a method of preventing reuse of a cartridge in a diagnostic system, comprising scanning a scannable code on a cartridge with an external scanner, wherein the scannable code contains data on at least one of a record of use, a test protocol for the cartridge, a patient information, a lot number for the cartridge contents, a serial number for the cartridge, an expiration date for the cartridge; inserting the cartridge into a diagnostic instrument; scanning the scannable code on the cartridge with an internal scanner once inside the diagnostic instrument; comparing the data between the scans to identify whether an unused cartridge was inserted into the diagnostic instrument; providing feedback to a user on whether the cartridge was previously used by the diagnostic instrument.

In some embodiments, the present disclosure relates generally to a method of preventing reuse of a cartridge in a diagnostic system, wherein the cartridge is removed from a protective package before scanning by the external scanner.

In some embodiments, the present disclosure relates generally to a method of preventing reuse of a cartridge in a diagnostic system, wherein the diagnostic instrument will not allow processing the cartridge if the cartridge is a used cartridge.

In some embodiments, the present disclosure relates generally to a method of preventing reuse of a cartridge in a diagnostic system, wherein the internal scanner scans the cartridge before processing of the cartridge.

In still another embodiment, the disclosure relates generally to a method of preventing improper use of a cartridge, comprising scanning a scannable code on a protective package containing a cartridge, wherein the first scan sets a first limit of an expiry time limit predetermined for proper use of the cartridge; introducing the cartridge into a diagnostic instrument with an internal scanner; scanning the scannable code on the cartridge with the internal scanner, wherein the internal scan sets a second limit of an expiry not to exceed a predetermined limit for proper use of the cartridge; calculating the difference between the first and the second time limits; comparing the difference in time to the predetermine time limit for proper cartridge use; and providing feedback to user if time limit was breached.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." The use of the term/phrase "and/or" when used with a list means one or more of the listed items may be utilized, e.g., it is not limited to one or all of the elements.

This summary of the embodiments does not necessarily describe all features or necessary features of the embodiments. The embodiments may also reside in a sub-combination of the described features.

BRIEF DESCRIPTION OF THE DRAWINGS

The accompanying tables and figures are incorporated in, and constitute a part of this specification.

FIG. 8E is a cross-section view of an ECL detection system of an embodiment;

DETAILED DESCRIPTION

Figure 1:
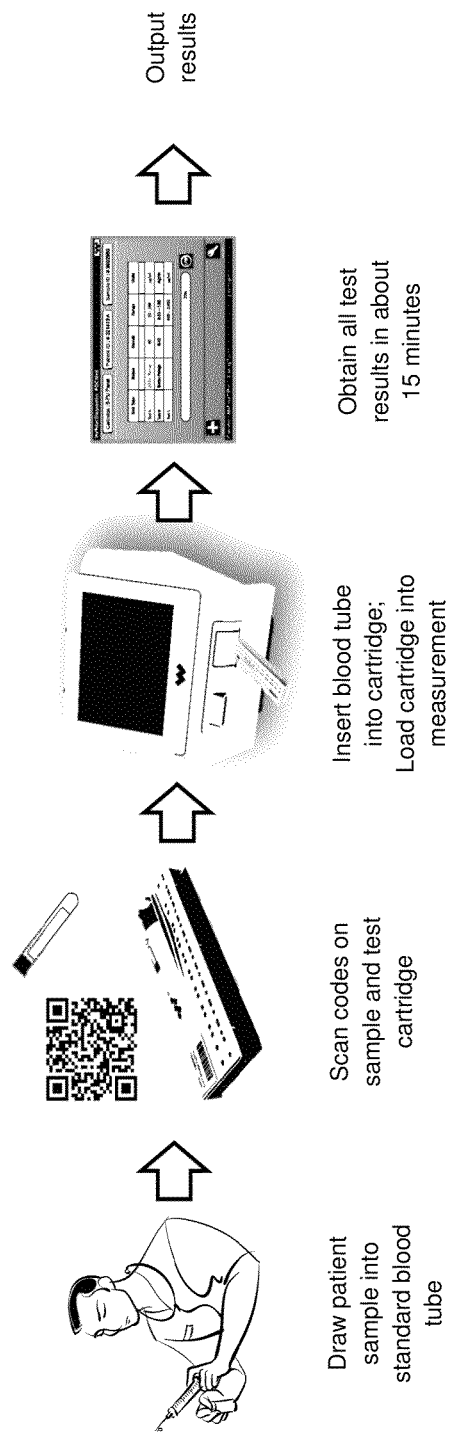
FIG. 1 is an illustration of an embodiment the diagnostic system described herein.

The following are definitions of terms related to the diagnostic system in general.

The term "bead(s)" as used herein refers to many types of microscopic particles, such as superparamagnetic particles, magnetic microparticles, and magnetic nanoparticles. A bead may typically be spherical, though the shape is not limited to that of a sphere and may include other shapes like spheroid, irregular particles, cubes, irregular cubes, and disks. The size range may cover from 1 nanometer to 10 microns in diameter.

The term "standardized quantity" as used herein refers to a known amount of a substance, where the amount might be mass, concentration, volume, number, or other physical quantity. The known amount may have been determined or traceable to a reference method, golden standard, NIST traceable standard or other. A known amount of a substance may also be determined by comparing an analytical result to a calibrator.

The term "fluorescence" as used herein refers to the emission of light by a substance that has absorbed light or other electromagnetic radiation.

The term "fluorophore" as used herein refers to a substance that is fluorescent.

The term "fluorescent label" as used herein means a fluorophore used in the detection or measurement of fluorescence. A substance which is fluorescent yet detected by another detection method, such as ECL, is not a fluorescent label. A fluorescent label is only operative when measuring fluorescence. Fluorescent beads are the same as fluorescent labeled beads.

The term "assay construction" as used herein refers to the step by step process of conducting an assay whether manual or automated. Assay construction typically involves laboratory operations such as pipetting, dispensing, metering, washing, free-bound separations, dialyzing, filtering, collecting, fractionating, diluting, mixing, incubating, and the like.

The term "fluidic element" as used herein refers to a structure to hold, carry, or allow transport of a fluid. A fluidic element includes a pipe, channel, well, reservoir, conduit, valve, vent, flow path, disperser, pipette, funnel, filter, and passageway.

The term "fluidic communication" as used herein refers to fluidic elements that are in fluidic communication if connected a channel, passageway, pathway, conduit, flow path or other fluidic element. Further, fluidic elements are in fluidic communication if connectable or transferable by a pipette. Further, fluidic communication includes adjacent or nearby fluidic elements which liquid may be dispensed or transferred by pipette between or from one to the other. For example any two wells of a 96 well microtiter plate are in fluidic communication.

The term "assay composition" as used herein means the complete set or subset of the necessary reagents or substances required for an assay when combined. An assay composition may be the initial composition prior to assay construction, the composition immediately after initiating assay construction, the final mixture after assay construction, or the composition at any intermediate step of assay construction.

"Precise" throughout this document refers to the reproducibility and repeatability of a characteristic. "Highly precise" means the characteristic variation is small over many observations of the characteristic. For example, the precision of cavity height Z in FIG. 8A refers to the variation of height Z observations seen after repeating the measurement on enough flow cells to statistically characterize the population.

Presently disclosed is a diagnostic system that can measure immunoassays and perform bioanalytical functions in various environments, including in a point of care clinical setting. The diagnostic system generally includes a diagnostic instrument and a disposable vehicle, such as a cartridge, for carrying reagents, processed samples and other necessary materials used in diagnostic functions.

FIG. 1 provides a schematic drawing illustrating an overview of the diagnostic system described in the present disclosure. The diagnostic system further includes features that are U.S. Food and Drug Administration (FDA) approved and/or have/can obtain(ed) a Clinical Laboratory Improvement Amendments (CLIA)-waived categorization. For example, as illustrated in FIG. 1, in operation of certain embodiments, a patient sample, such as venous whole blood, is drawn into a standard blood tube, which can then be inserted into a disposable cartridge, which can include barcodes or other identifying marks. Next, the cartridge can be loaded into an analyzer, such as a diagnostic instrument for processing. The results from the diagnostic instrument can be obtained and presented in as little as 8 to 15 minutes for up to ten different tests. The results of the test can be output via printer, laboratory information management systems (LIMS), or via other output devices.

It is contemplated that the processing time for an individual cartridge may be longer, for example, up to 20 or 30 minutes, depending on the amount of different tests being run on the individual cartridge. If there are fewer tests to be run on a single cartridge then less time may be expected to complete the processing cycle. The number of tests that can be run on an individual cartridge can vary as well. For example, a single cartridge can run a single test during a processing cycle or three tests or five tests, or any number of tests up to ten on a single cartridge for a single processing cycle of the diagnostic system.

Figure 2:
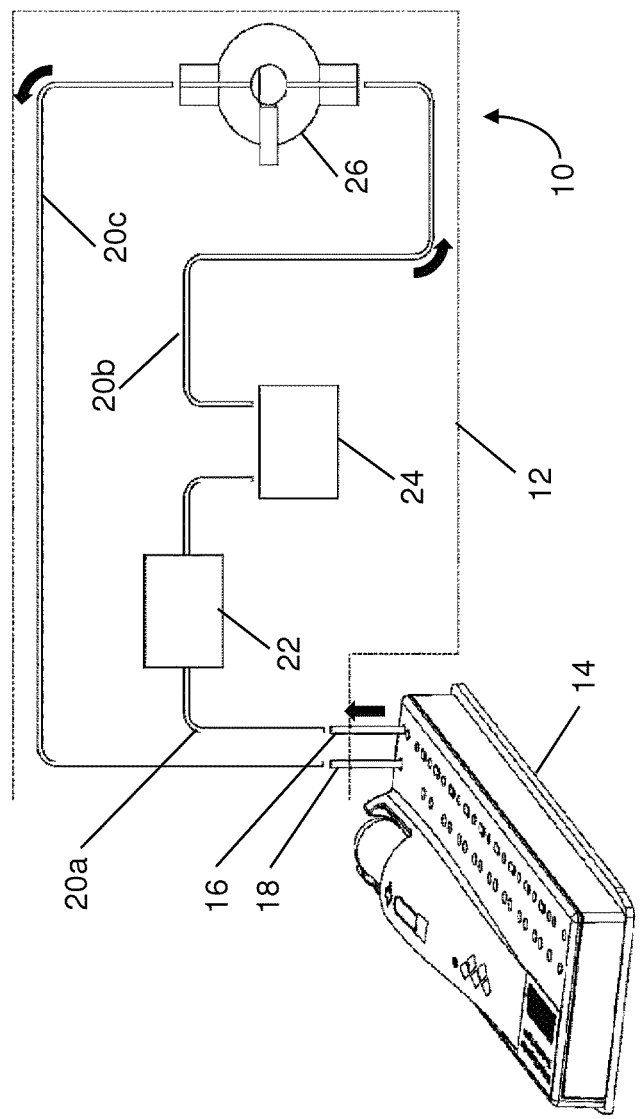
FIG. 2 is an illustration of an overview of the closed fluidic pathway between a diagnostic instrument and a cartridge in an embodiment.

In certain embodiments, a diagnostic system includes a diagnostic instrument (See, e.g., FIG. 1) and a disposable cartridge (See, e.g., FIG. 2). In other embodiments, a system may include additional or alternative diagnostic instruments, such as intermediate processors or non-compact components, or may use test cards, or reaction plates, or other disposable devices. The disposable cartridge can be used with the diagnostic instrument, which is preferably compact and self-contained, to perform diagnostic tests, such as measuring an immunoassay or a panel of immunoassays or detecting analytes, in a biological sample such as blood. The diagnostic instrument can run different diagnostic tests, such as assays, by using different disposable cartridges designed for each diagnostic test desired.

In some embodiments, a diagnostic instrument can include a motion assembly for positioning and accessing the cartridge, at least one fluidic tube, a pump for liquid handling, and an ECL detection system. The diagnostic instrument can also include a platform for a user interface, such as a touch screen, and/or at least one internal and at least one external barcode scanner for data entry.

The diagnostic instrument also may provide safety and failsafe mechanisms throughout a workflow process. One such failsafe mechanism is an internal standard, which comprises both a module and a method for quantifying the bead recovery from the processing steps of a cartridge run independently of the ECL measurement. It is contemplated that the at least one internal and external barcode readers can also be used as a failsafe mechanism. In particular, barcodes read on the disposable cartridge externally must match those read internally, to verify that the cartridge was not switched after the initial scanning. In the event that the external and internal reads do not match, the diagnostic instrument may inform the user through the user interface by displaying an error message, for example.

As part of the diagnostic system, the diagnostic instrument has multiple aspects that are correlated to a disposable cartridge. Thus, in certain embodiments, a complementary and correlating cartridge (See, e.g., FIGS. 1 and 2) contains all reagents and materials needed to perform a diagnostic test, such as, for example, run a particular panel of assays. Some embodiments of the cartridge can include at least one needle, at least one fluidic channel, and at least one fluidic seal. Additionally, the cartridge can have at least one reservoir for collecting all waste reagents from the assays or other diagnostic tests. Analyte specific reagents are essentially dry (e.g., lyophilized) to improve stability and can be located on the cartridge for use in the diagnostic test. Similarly, liquid reagents such as an ECL read buffer and a pump priming fluid can be stored on the cartridge. The cartridge can have at least one needle that may be shrouded and onto which an operator can fit a standard blood tube. The disposable cartridge can be designed in such a way that all liquid waste will leave the diagnostic instrument via the cartridge. In some embodiments, calibration and/or other assay information can be encoded on a cartridge in a machine-readable format, e.g., using a barcode.

Some embodiments of a disposable cartridge, in order to prepare and process a sample, e.g., on an ECL detection system, have various components and use various methods as described herein. These methods include, but are not limited to, methods of blood filtration (e.g., using tangential flow), methods for liquid-air transition detection in the channels of the cartridge, methods for aliquoting a clinical sample via segmented metering, methods for mixing reagents, methods for incubating the assay and washing the sample matrix away. These methods are all covered herein.

Further embodiments and details are described in the co-pending U.S. patent application entitled "DIAGNOSTIC SYSTEMS AND CARTRIDGES;" the application filed on Mar. 15, 2013, with inventors R. Cook, C. Davis, J. Harley, J. Leland, R. Matikyan, J. Peterman, and assigned application Ser. No. 13/844,527, herein referred as the '527 application, and herein incorporated by reference in its entirety.

Instrument Design.

The designs of certain embodiments of the diagnostic instrument are disclosed in co-pending U.S. Design application Nos. 29/420,956 and 29/420,965, both filed on May 15, 2012, each of which is herein incorporated by reference in its entirety. Images contained within those disclosures prescribe clinical instruments of the diagnostic system, and designs thereof, which relay both the function and form, and the connection between the product, the user, and the environment. Such images merely represent instruments and the present disclosure is not limited to these particular instruments or designs.

Closed Fluidic Pathway.

In certain embodiments, the diagnostic system employs a closed fluidic pathway between the diagnostic instrument and the disposable cartridge. The closed fluidic pathway provides a pathway where a biological sample and necessary reagents are withdrawn from the cartridge using a substantially single direction of flow which returns used reagents and other waste materials to the cartridge. The connection of the blood tube to the cartridge facilitates access to the majority of the blood contained within the blood collection tube while maintaining a low profile within both the instrument and cartridge. In some embodiments both a multi-layer film structure and a multi-layer heat sealable film are used for sealing the top and bottom of the disposable cartridge. In some embodiments, a multi-layer blood filtration assembly is used in a disposable cartridge, e.g., to remove red blood cells from the blood sample and/or to isolate blood plasma or serum. These aspects are discussed in further detail herein.

Figure 3:
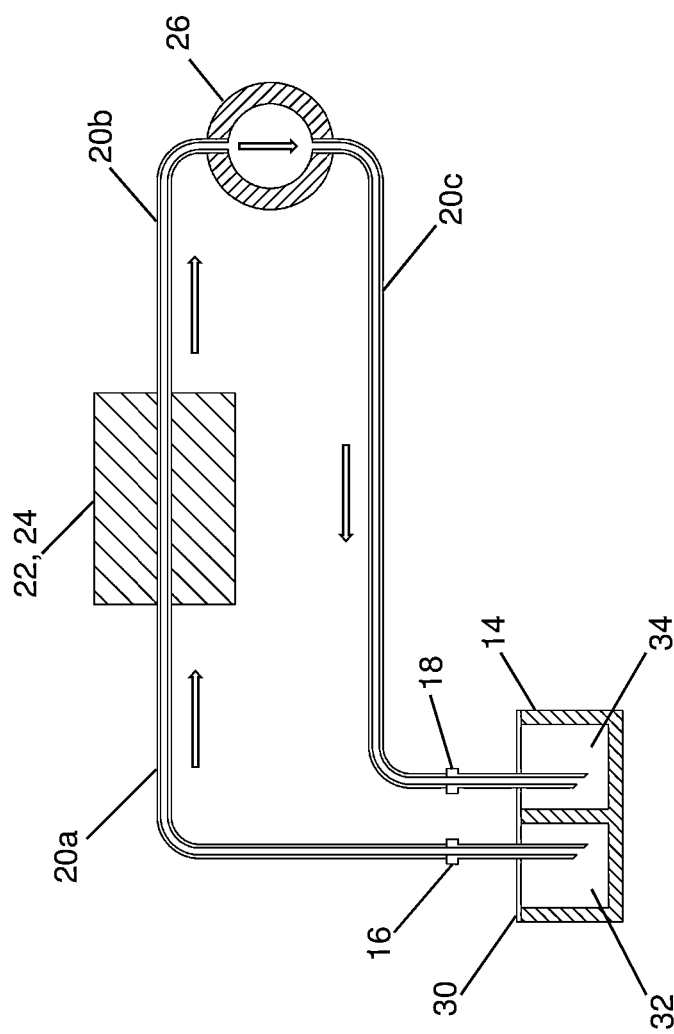
FIG. 3 is an illustration of a general configuration of a fluidic system of an embodiment.

As illustrated in FIGS. 2 and 3, in some embodiments, the diagnostic instrument 12 has a first probe 16 and a waste probe 18, wherein the first probe 16 of the diagnostic instrument 12 can fluidically communicate with and connect reagents and materials within the cartridge 14 to the diagnostic instrument 12. The waste probe 18 of the diagnostic instrument 12 can fluidically communicate with the at least one reservoir (not depicted) of the cartridge 14 to facilitate the disposal of waste materials thereby terminating the fluidic loop of the closed fluidic pathway.

Some embodiments provide the use of a closed fluidic pathway 10 that can communicate between a diagnostic instrument 12 and a disposable cartridge 14 (See, e.g., FIG. 2). In one implementation, a diagnostic instrument 12 is provided. As illustrated in FIG. 2, at least one probe can be provided for introduction into a disposable vehicle, such as a cartridge 14, thereby creating a means to withdraw diagnostic reagents and other necessary materials through a first probe 16 into a closed fluidic pathway 10 using a substantially single direction of flow which terminates at a waste probe 18. The waste probe 18 provides a means to return used reagents and other waste materials to the disposable cartridge 14. By providing the closed fluidic pathway, test materials can be withdrawn from the disposable vehicle, and after processing the diagnostic test, the test materials can be returned to the cartridge through the closed fluidic pathway thereby not returning the used materials through the fluidic path to interfere with subsequent tests. The substantially single direction of the flow and the closed-loop configuration serve to reduce the potential for carryover between tests. Opportunities for carryover can be further reduced by transporting fluids through a single non-branching fluidic path.

In some embodiments, a closed loop fluid system for use in processing in vitro diagnostic tests is provided. In some embodiments, the closed fluidic pathway 10 originates and ends with two separate probes where a first probe 16 facilitates the withdrawal of test materials from a disposable vehicle, such as a cartridge 14, and a waste probe 18 facilitates the return of waste materials to the cartridge. In some embodiments, fluid flow is substantially single directional in order to reduce the potential for carryover between diagnostic tests.

FIG. 2 provides an embodiment of a diagnostic system having a closed fluidic pathway 10 comprising a diagnostic instrument 12 having at least one probe 16, 18; at least one fluidic tube 20; a non-ECL detection system (or an IS module) 22; an ECL detection system 24; a pump 26; and a motion assembly (not depicted). The closed fluidic pathway 10 also comprises a disposable cartridge 14 having at least one needle (not depicted); at least one reservoir (not depicted) at least one fluidic seal (not depicted); and at least one fluidic channel (not depicted), wherein the closed fluidic pathway 10 substantially flows in one direction in a loop fluidically connecting the diagnostic instrument 12 and the disposable cartridge 14.

The closed fluidic pathway can have a substantially single directional flow which can reduce a potential for carryover between diagnostic tests. The motion assembly (not depicted) can have two axes of motion and can further comprise an incubator (not depicted), which can be a multi-zone incubator. The incubator can achieve uniform and precise incubation of a biological sample within the cartridge.

In some embodiments, the fluidic path of the closed fluidic pathway flows from a diagnostic disposable, such as a cartridge 14, which contains all materials necessary to process the diagnostic test, through a first probe 16. All the reagents and other test materials enter the fluidic path at the first probe 16 and flow to and through at least one detection instrument 22, 24 in which the diagnostic test is processed. The test data is obtained after the reagents pass through the fluidic path and into a pump 26. The processed sample and waste materials leave the pump 26 through a continuation of the fluidic path and return to the disposable cartridge 14 through the waste probe 18. The flow of fluid is substantially single directional from the cartridge 14, through the at least one detection instrument 22, 24, through the pump 26, and back to the disposable cartridge 14. The substantially single directional flow can reduce test to test carryover. The opportunity for carryover increases in the pump 26 as the pump likely represents a discontinuity in the geometry of the flow path, therefore maintaining a buffering length of fluidic path between the detection instruments and the pump, greater than the volume of any potential backflow is desirable to prevent carryover.

In certain embodiments, a fluidic pathway of a closed fluidic pathway can be defined by a first probe 16, which can be formed from a hollow needle, and which can begin a fluidic pathway for a diagnostic system. The fluidic pathway of the closed fluidic pathway 10 can have a first tube 20$a$ establishing fluidic communication with and having the same inside diameter as the first probe 16. At least one detection instrument 22, 24 can encompass a fluidic pathway that is matched at its origin to the inside diameter of the tube and establishing fluidic communication therewith. A second tube 20$b$ can establish fluidic communication between the at least one detection instrument 22, 24 and a pump 26, having the same inside diameter as the fluidic pathway at the exit of the detection system and at the entrance of the pump 26. The pump 26 can provide motive force for fluidic motion within the fluidic pathway, having a logical entrance and exit for fluidic flow. A fluidic pathway continues in the form of a third tube 20$c$ establishing fluidic communication with and having the same inside diameter as the exit of the pump 26 and a waste probe 18. The waste probe 18, formed from a hollow needle, constitutes the end of a fluidic pathway.

In FIG. 3, an embodiment of a fluidic system is shown. A fluidic communication between the diagnostic instrument 12 and a disposable cartridge 14 can be established when a first probe 16 of the diagnostic instrument 12 contacts and enters into at least one fluidic reservoir 32 on the disposable cartridge 14 by piercing a fluidic seal 30. The first probe 16 can then establish fluidic communication with various containment areas within the disposable cartridge 14 in order to extract test materials and/or process materials within the disposable cartridge 14. For example, reagents can be aspirated from a reagent well 32 by the first probe 16 for processing during a diagnostic test run.

The waste probe 18 can also establish fluidic communication with various containment areas within the disposable cartridge 14 in order to return waste materials to waste containment areas 34 within the disposable cartridge 14. The substantially single directional flow of the fluidic system is depicted in FIGS. 2 and 3 by the arrows. In some embodiments, the fluidic system creates a substantially single-direction fluidic flow from the first probe 16 through the first tube 20$a$, the at least one detection instrument 22, 24, the second tube 20$b$, the pump 26, the third tube 20$c$, and terminates at the waste probe 18. Test materials can be processed along this route beginning within reagent wells 32 and other containment areas of the disposable cartridge and returning all waste materials to waste containment areas 34 of the disposable cartridge.

For example, in some embodiments of the diagnostic system, a cartridge 14 can have an initially empty chamber is provided to receive waste materials from the initial diagnostic test. During the initial diagnostic test, reagent is removed from its designated reagent containment chamber for use in processing that test. In the course of the subsequent tests, waste material from that test is returned to the reagent chamber emptied during the prior test. By using previously emptied reagent chambers for waste containment the overall volume requirement of the disposable cartridge is reduced.

In some embodiments, a fluidic system is formed of one or more segments of fluidic pathway typically, but not necessarily, in the form of tubing. In FIG. 3, for example, inside diameters of each segment of the fluidic pathway are matched at the junctions of each segment in order to mitigate potential carryover traps. The fluidic pathway begins with a first probe 16, preferably, but not necessarily with a non-coring tip profile such that it may pierce a foil or a multi-layer film structure such as a septum 30 on a diagnostic disposable cartridge 14 housing thus establishing fluidic communication between the fluidic system and the disposable cartridge 14.

The next segment establishes a fluidic pathway to at least one detection system 22, 24. This fluidic pathway segment may be a part of or separate from the segment such as a tube 20a passing through the at least one detection instrument 22, 24. The at least one detection instrument 22, 24 comprises the next segment of the fluidic system, where detection is performed without the sample leaving the fluidic pathway. The next segment of the fluidic pathway may be a separate item such as a tube 20b, or may be incorporated into either the detection system or the pump 26, as long as it establishes fluidic communication between the at least one detection instrument 22, 24 and the pump 26. If necessary, additional pieces of tubing or other suitable fluidic pathway materials may be incorporated to connect multiple detection systems.

The next fluidic pathway establishes fluidic communication between the pump and the waste probe 18. The fluidic pathway terminates with a waste probe 18, preferably, but not necessarily with a non-coring tip profile such that it may pierce a foil or a multi-layer film structure, such as a septum 30, on a diagnostic disposable cartridge 14. The waste materials from the diagnostic test can be returned to otherwise empty chambers 34 of the disposable cartridge 14.

Various portions of the fluidic system may be comprised of separate pieces that make up the fluidic pathway or may be combined, for example, to further reduce potential for carryover between diagnostic tests. Examples include but are not limited to: (a) combining the first probe and the first tube; (b) combining the third tube and the waste probe; (c) having one continuous tube encompassing the first probe and the balance of the fluidic path terminating at the pump; and/or (d) combining the detection system(s) and the pump into a single manifold encompassing the fluid pathways between them. It is contemplated that the arrangement of the internal components within the diagnostic instrument can be configured to satisfy desired standards, including size, weight, shape, aesthetic appearance.

Method of Temperature Control of a Cartridge.

Certain embodiments provide a method for achieving a uniform and precise incubation of patient plasma with the selected reagents, in a disposable cartridge-based point of care system to facilitate the binding of the detection reagents to a particular antigen, for example, those that may be present in a biological sample such as a patient's plasma. By using an incubator (single or multi-zone) and by measuring the starting temperature of the cartridge, precise incubation with temperature uniformity can be achieved in such a manner that the effect of variations of the storage temperatures for the cartridge prior to use. Unwanted variations of the operating temperature of the instrument are also minimized, and do not affect the measured concentrations of analytes such as antigens in the biological sample.

In particular, some embodiments ensure that if the same biological sample or patient's blood is analyzed in a cartridge that was stored in different temperatures, the result will still show the same level of concentration of antigen or analyte activity. Likewise, other embodiments ensure that if the same patient's blood is analyzed in an instrument that is being operated in different temperatures, the result will still show the same level of concentration of antigen or analyte activity.

In some embodiments, using electrochemiluminescence (ECL) technology, the amount of binding that takes place (i.e., activity of reagents, sample and analytes) is directly related to the incubation temperature and duration of the incubation of the sample. The amount of measured antigen is directly related to the amount of binding that takes place. Thus, it is advantageous to receive accurate results that can be generated even if the cartridges and the instruments are stored and operated at different temperatures. It is another advantage of the diagnostic system, that users of the diagnostic system do not need to tightly control the temperature of their working environments within which they will operate the diagnostic system. In particular, a diagnostic system user does not need to dedicate temperature controlled storage location to store the disposable device (i.e., cartridges). This also provides for increased efficiency in the processing since the temperature control method compensates for variations in temperatures and quickly adjusts to a controlled uniform operating temperature.

Figure 4A:
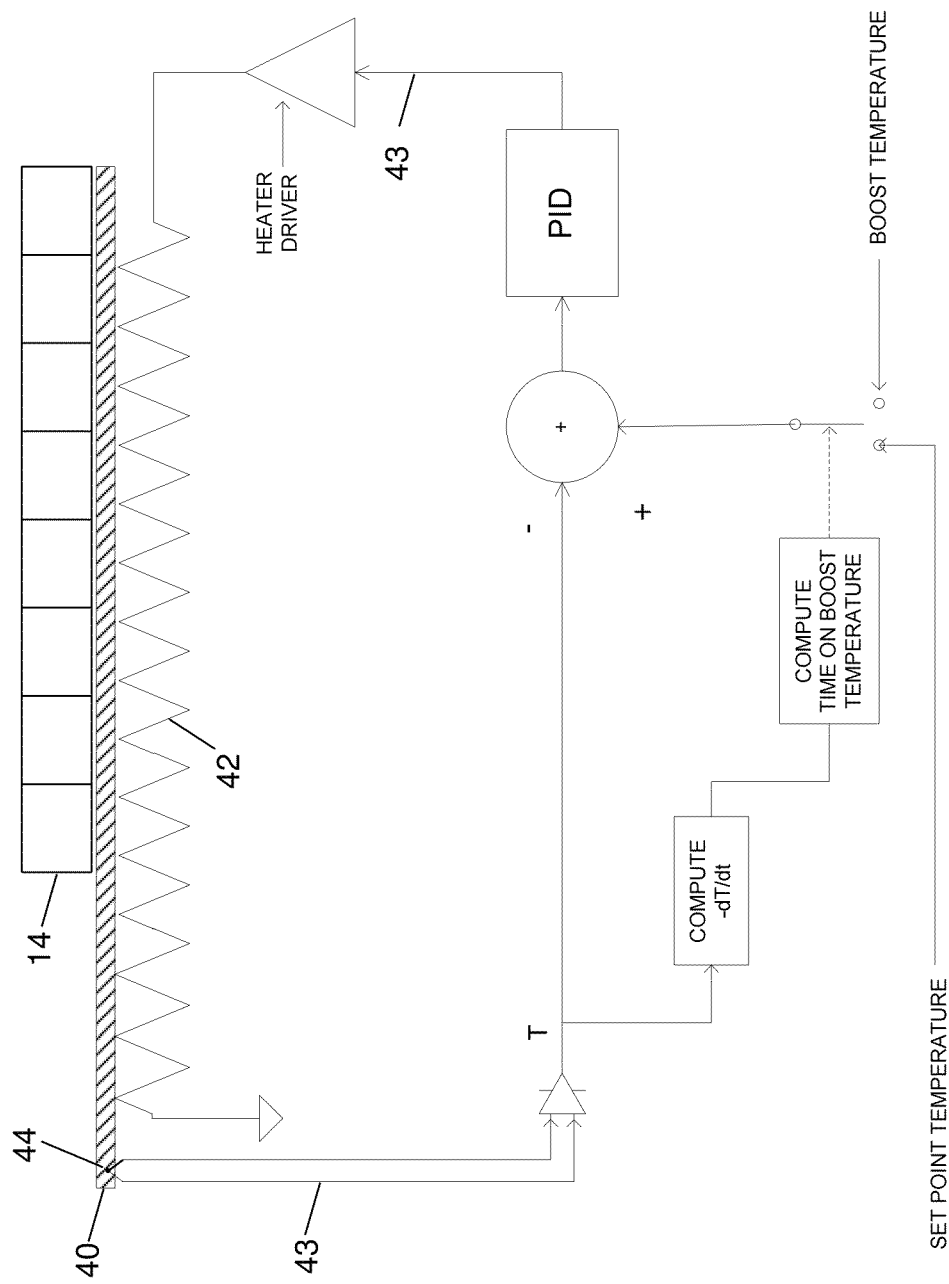
FIG. 4A is an illustration depicting the components as well as the feedback control loops of a single zone incubation system of an embodiment.
Figure 4B:
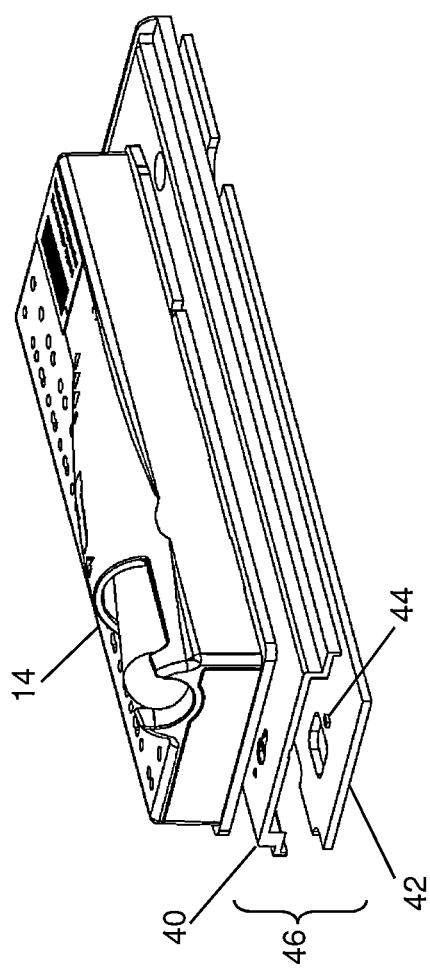
FIG. 4B is an alternative perspective view depicting the components of an incubation system of an embodiment.

FIG. 4A is an illustration depicting an incubator plate 40, a heater 42, a sensor 44, and a control loop 43 used in measuring the starting temperature of the cartridge 14 and providing a temperature control mechanism for the incubation of the sample in the cartridge 14. FIG. 4B provides a perspective view of the spatial relation of the cartridge 14 and the incubator 46 comprising the individual components of heater 42, sensor 44, incubator plate 40 within a diagnostic system, and wherein the surrounding components of the diagnostic instrument are not presently depicted.

In an embodiment, a method of temperature control of a cartridge 14 comprises measuring with a sensor 44 the starting temperature of the cartridge 14 containing a biological sample and at least one reagent; adjusting a set of predetermined pre-incubation parameters depending on the measured starting temperature; heating with a heater 42 the cartridge 14 to a target temperature; maintaining the target temperature for a period of time equal to or less than the time it takes to complete a diagnostic test; intermittently measuring the temperature of the disposable cartridge 14 throughout the segment of time of the diagnostic test to ensure temperature control; and heating at least a portion of the disposable cartridge 14 to the target temperature when the temperature of the disposable cartridge 14 is less than the target temperature. The term "starting temperature" as used herein refers to the initial temperature of the bottom of a cartridge 14 the instant the cartridge 14 is inserted into the instrument 12.

In certain embodiments, the at least one heater 42 and/or at least one temperature sensor 44 can detect the cartridge 14 temperature. The heater 42 and temperature sensor 44 can be on a printed circuit board, which is integrated into a motion assembly (not depicted) of the diagnostic instrument. The same temperature sensor 44 can be used to measure the cartridge 14 temperature and used in the closed loop control to maintain the temperature of the cartridge 14. Alternatively, different temperature sensors can be used to measure the cartridge 14 temperature and used in the closed loop control to maintain the temperature of the cartridge. The method of incubation can further comprise repeating the incubation method for the duration of the diagnostic test until completion. "Closed loop control" in this document refers to a control system with one or more sensors providing feedback signals to the control system that are used to modulate the system response. For example, the temperature control system shown in FIG. 4A modulates the incubator heater power based on output of temperature sensor 44. Here, the temperature sensor 44 provides the feedback signal that closes the control loop. Contrast this to "open loop control" systems, where no feedback signal is used to modulate the system response.

In certain embodiments, the incubation also can be performed by a multi-zone temperature control incubator. The multi-zone temperature control incubator can operate under independent control loops (See, e.g., FIG. 5). The incubator can achieve uniform and precise incubation of a biological sample within the cartridge 14. The multi-zone temperature control incubator can provide a more uniform temperature control along the body of the cartridge. This will allow for multiple measurements of the same sample for multiple tests, by allowing a uniform temperature to be maintained among the multiple measurements. Using the multi-zone temperature control incubator further improves temperature uniformity and precision during processing and operation of the diagnostic system.

In certain embodiments, during operation of the diagnostic system, a biological sample, such as a patient's blood, can be filtered to generate plasma within the cartridge using a filtration module. An example of a suitable filtration module is described in the co-pending International PCT Application No. PCT/US2012/067041, filed on Nov. 29, 2012, and which is herein incorporated in its entirety.

Figure 6A:
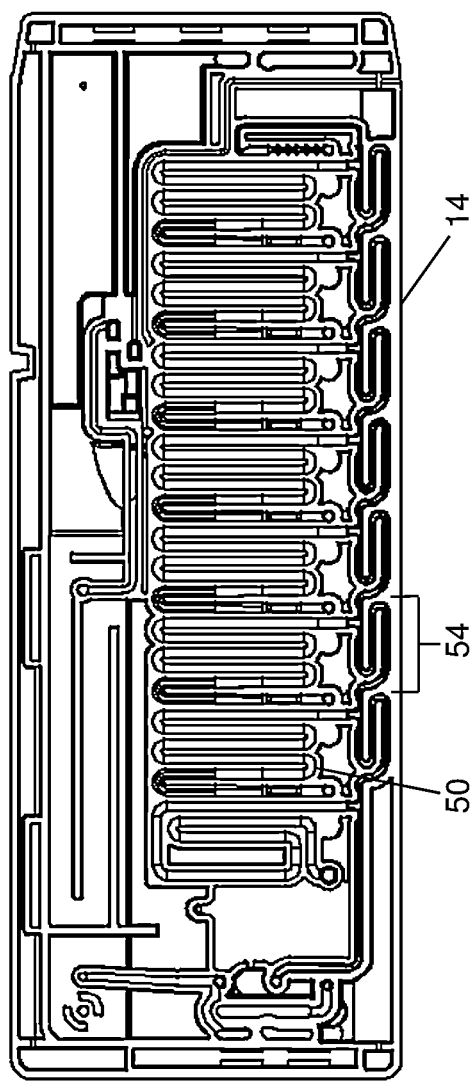
FIG. 6A is a plan view depicting multiple fluidic channels of a cartridge of an embodiment.
Figure 6B:
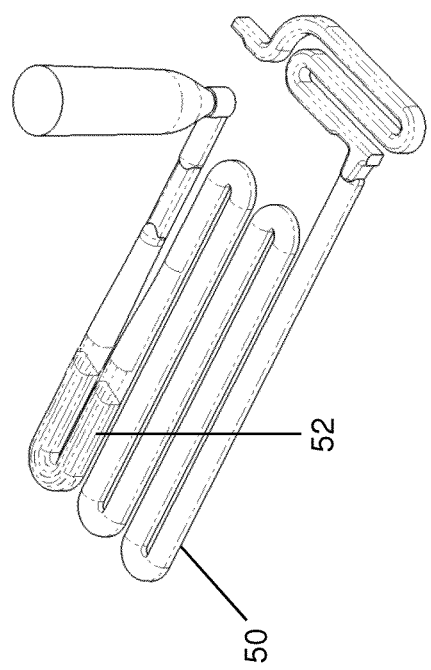
FIG. 6B is an isolated view of a single fluidic channel of a cartridge of an embodiment.

The plasma sample can be metered and moved into individual fluidic test channels 50, such as those depicted in the embodiments of a disposable cartridge in FIGS. 6A and 6B. FIG. 6A illustrates the bottom of a cartridge, showing multiple fluidic channels 50 arranged into single cartridge assay replicates (CAR) 54, which represent independent channels in a cartridge 14 that can process different tests for the same patient. A single CAR is shown in FIG. 6B, holding a sample 52 in a fluidic channel 50.

For each test channel, the metered plasma sample then can be moved and mixed with reagents, such as with lyophilized reagents. The mixture then can be moved to a location in the channel and parked. The bottom of the cartridge where the mixed plasma makes contact can be a thin film, such as a bottom seal that is transparent. The cartridge 14 can be positioned on a flat surface of an incubator which is comprised of various components including an incubator plate 40 that can be heated by a heater 42 usually positioned under the incubator plate 40.

A temperature sensor 44 can be located at several varying locations on the heater 42. It is contemplated that more than one sensor may be incorporated into the incubator. The sensors 44 can measure the temperature of the incubator plate 40 that is heated by heater 42. The sensor 44 measurements can be monitored by the Central Processing Unit (CPU) (not depicted), and a closed loop proportional-integral-derivative (PID) control can be used to maintain the temperature of the incubator 40 at the target temperature for a period of time. The period of time for incubation of the cartridge 14 can be equal to or less than the time it takes to run a complete diagnostic test on the cartridge. In general, the incubation occurs as an initial step in the diagnostic system processing and is used to prepare the sample before and during sample measurements take place within the diagnostic instrument. Thus, depending on how many tests are being run off of any given cartridge, the time period for incubating the cartridge will span at least the time of processing all the tests on a cartridge.

In some embodiments, measuring the starting temperature of the cartridge can be achieved when, after a cartridge 14 is inserted, the heater 42 is momentarily shut off. The rate of the incubator plate's 40 temperature loss is computed, for example, by monitoring the same sensor 44 that is being used to control the temperature. The rate of temperature loss is related to the rate that heat transfers from the incubator plate to the cartridge 14. The rate that heat transfers from the incubator plate 40 to the cartridge 14 is related to the temperature difference between the incubator plate 40 and cartridge 14. By computing the temperature difference between the incubator plate and cartridge, the temperature of the cartridge can be found. Finally, having determined the temperature of the cartridge 14, the duration of the Idle (Boost) Target Temperature is adjusted accordingly. The term "boost" as used herein refers to an initial application of temperature for a certain time and at a certain location on an incubator that can be used to heat up the cartridge. The incubator heats up the cartridge by applying a higher incubation temperature set point than a normal incubation temperature set point for a duration of time at a location on the incubator.

The diagnostic instrument 12 when there is no cartridge inserted, can maintain the temperature of the incubator plate 40 at an idle target temperature. When a cartridge 14 is inserted into the diagnostic instrument 12 and positioned on the incubator plate 40, the diagnostic instrument 12 can start detecting the temperature of the cartridge 14, by measuring with a sensor 44 the rate of the temperature drop of the incubator plate 40 due to the different temperature of the cartridge 14. The drop rate (calculated by the CPU) can be used to determine the starting temperature of the cartridge. The drop rate can then be used to select the duration (from a pre-constructed table or an equation) that the cartridge can be kept on the incubator plate 40 at the Idle (Boost) Target Temperature. This process ensures that the cartridges, regardless of storage temperatures, will have reached a similar temperature by the time the sample is ready to start a reaction with the reagent. Since the cartridge temperature can become the same prior to the beginning of incubation, all cartridges receive uniform incubation regardless of their individual storage temperatures.

The presently disclosed method of temperature control ensures, among other things, that all samples start incubation at the same temperature regardless of cartridge storage temperature and that all samples receive the same amount of incubation activity regardless of cartridge storage temperature.

Figure 5:
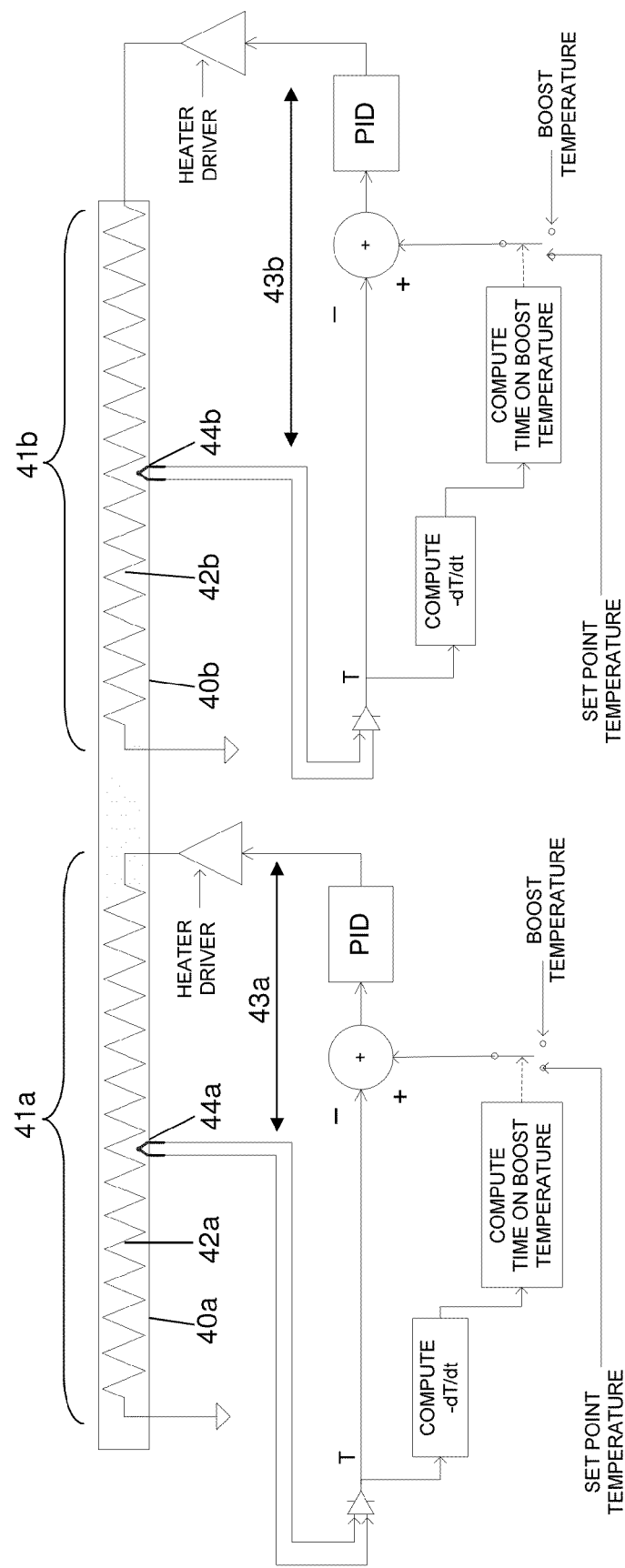
FIG. 5 is an illustration depicting the components as well as the feedback control loops of a multi-zone incubation system of an embodiment.

A multi-zone incubator, such as that shown in FIG. 5, allows the diagnostic instrument to heat up the cartridge while, for example, filtering blood without affecting the temperature of the portion of the incubator that is not being cooled off by the cartridge. The multi-zone incubation is achieved by having two separate heaters 42a, 42b under the incubation plate 40. Each can have its own temperature sensor 44a, 44b. Each can have its own closed loop control 43a, 43b of the kind previously described. During heat up, the cartridge while filtering blood can be positioned on one of or part of both of the incubation zones 41a, 41b depicted in FIG. 5, and can remain there during filtration for a long period of time, for example, up to about 150 seconds. The multi-zone incubator does not require an added temperature sensor to measure the starting temperature of the cartridge that is coming into the instrument from its storage temperature. The same temperature sensor 44a, 44b, for example, the thermistor 44a, 44b in FIG. 5, that is in the feedback control loop controlling the incubator is also used for determining the starting temperature of the cartridge in this embodiment.

Internal Standard (IS) Module and Method.

In various embodiments of the diagnostic system several failsafe mechanisms and processes are incorporated to ensure the precise and accurate function of the diagnostic system. One such mechanism is the addition of an internal standard to the diagnostic system.

An IS is a substance that is added in a constant quantity to samples and calibration standards in an assay or analysis. An IS is a substance that is very similar, but not identical to the substance of interest in the sample. The effects of assay construction should be the same for the IS as the substance of interest.

One purpose of an IS is to identify failures that might occur during assay construction. As such, the method to implement the IS operates as a failsafe mechanism. Another purpose of an IS to correct for normal variability in assay construction. As such, the method to implement the IS operates as a means to improve precision and accuracy.

As part of the diagnostic system, there is a device such as a cartridge, which contains all reagents and materials needed to perform a diagnostic test, such as an assay. For diagnostic assays based on electrochemiluminescence (ECL) detection, one reagent is beads. This substance is used in the method to construct a diagnostic assay. In particular, the bead surface is the bound phase for a binding assay. For ECL-based assays, the quantity of label bound to the bead is measured by ECL detection and the ECL signal to concentration. In this aspect, the quantity of beads present during assay construction is critical to the overall performance of the diagnostic instrument.

For ECL-based assays, assay construction involves various processing steps. These may include free-bound separations, which generally consist of magnetic collection of the beads and bead wash steps. Any variability in the quantity of beads after such processing is undesired, as this may in some cases reduce precision and accuracy, in other worse cases cause an error in the reported result of the diagnostic assay.

In certain embodiments, fluorescent labeled beads are employed as an IS to prevent errors, and/or improve precision and accuracy in the reported results for ECL-based diagnostic assays.

Further, in certain embodiments, fluorescent labeled beads process identically to ECL labeled beads. As such, any variability experienced by ECL labeled beads are also found within the quantity of fluorescent beads. For example, if during magnetic collection, 95% of the ECL labeled beads in the sample were captured onto a magnet surface, then 95% of the fluorescent beads were likewise captured onto the magnetic surface.

In other embodiments, fluorescent labeled beads are employed as an IS to measure bead recovery after assay construction for ECL-based diagnostic assays. Bead recovery is the relative quantity (or percentage) of beads measured compared to the quantity of beads intended to be used in assay construction. For example, if 100,000 beads were initially contained within the diagnostic instrument, and upon completion of assay construction, 95,000 beads were measured, then bead recovery would be 95%.

Bead recovery is derived by comparing the fluorescence signal from the IS to the fluorescence signal from a standardized quantity of fluorescent beads.

Fluorescent beads can be labeled by coating fluorophore onto the bead surface. Coating can involve many different chemical or physical methods. Any one skilled in the art of conjugation can readily coat beads with fluorophore. Further, fluorescent beads can be alternatively be labeled by incorporating fluorophore within the interior of the bead. Further the beads can be labeled by both of the above methods.

IS can be comprised of fluorescent labeled beads, or fluorescent labeled and ECL labeled beads. In the first case, the sample would contain a mixture of fluorescent labeled beads and ECL labeled beads. In the second case, the sample would contain beads with both fluorescent and ECL label on the same bead.

Fluorophore can be allophycocyanin (APC) with an absorption maximum of 652 nm and an emission maximum 658 nm. Alternatively, the fluorophore can be Sky Blue (Spherotech) with an absorption maximum of 660 nm and an emission maximum 705 nm.

The beads can be superparamagnetic beads such as Invitrogen™ Dynabeads® M-280 Streptavidin or SPHERO™ Magnetic Particles.

The ECL label can be ruthenium (II) tris(2,2'-bipyridine).

In further embodiments, the diagnostic instrument of the diagnostic system includes a measurement and detection module, called an internal standard (IS) module, that is independent and distinct from an ECL detection system. The ECL detection system measures an ECL signal obtained from ECL labeled beads. The IS module and IS do not interfere with the ECL measurement. The IS module is a flow cell that measures fluorescence. The IS module performs a non-contact measurement to quantify fluorescence, and hence bead recovery. It is contemplated that the IS module can be in a separate location from the location of the ECL measurement, i.e., separate from the ECL detection system.

The IS measurement also can occur at a different time during an individual cartridge processing cycle, for example, prior to or at the same time as the ECL measurement during an individual cartridge processing cycle.

No physical contact is made with the sample and inside the tubing assembly except for the application of the laser light as the sample flows through the fluidic pathway or tubing assembly. A fluidic pathway can include any part of the diagnostic system where fluids can flow and is not limited to a tube structure such as the tubing assembly.

In general, the IS module uses a light source, such as a laser, laser diode, or light emitting diode to excite fluorescent labeled beads present within the sample moving through the IS module. The fluorescent labeled beads emit fluorescent light that can be accurately measured using a light detector such as a photodiode or photomultiplier tube. The measured light fluorescence signal can be compared with the fluorescence signal obtained for a known number of fluorescent labeled beads, and a percentage bead recovery calculated.

Figure 7A:
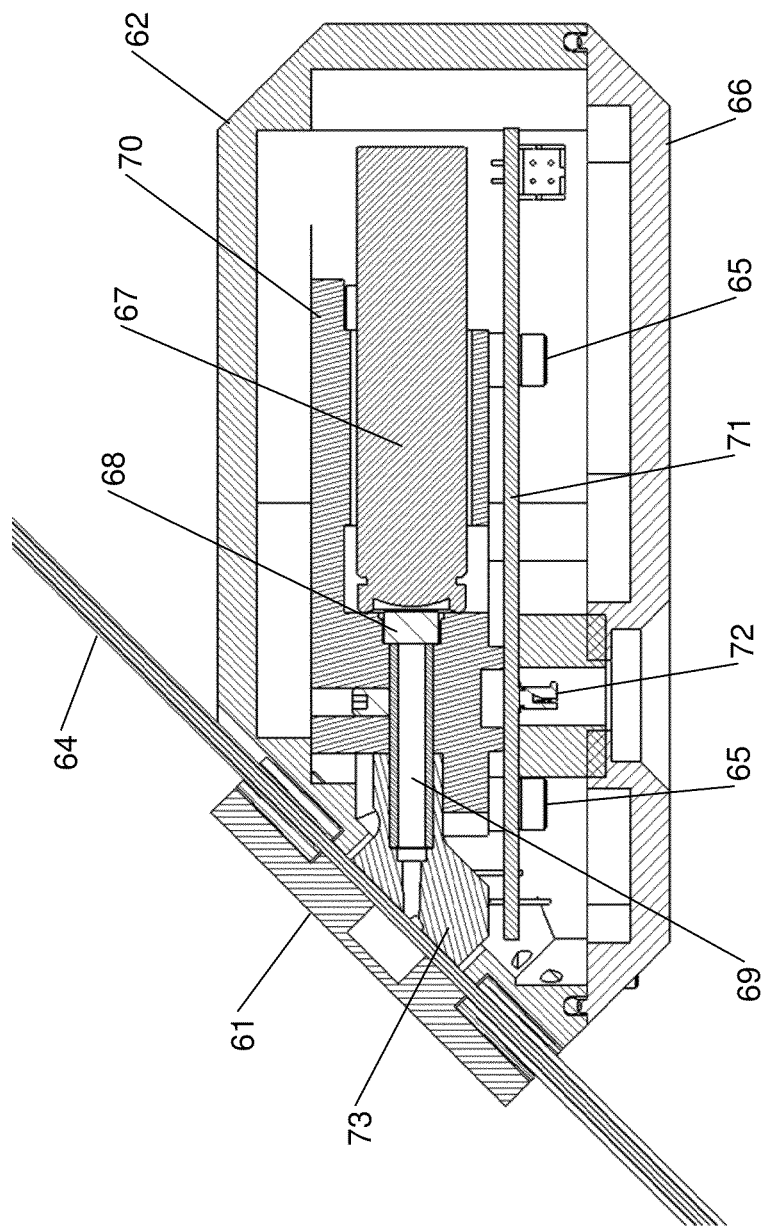
FIG. 7A is a cross-section view of an internal standard (IS) module of an embodiment.
Figure 7B:
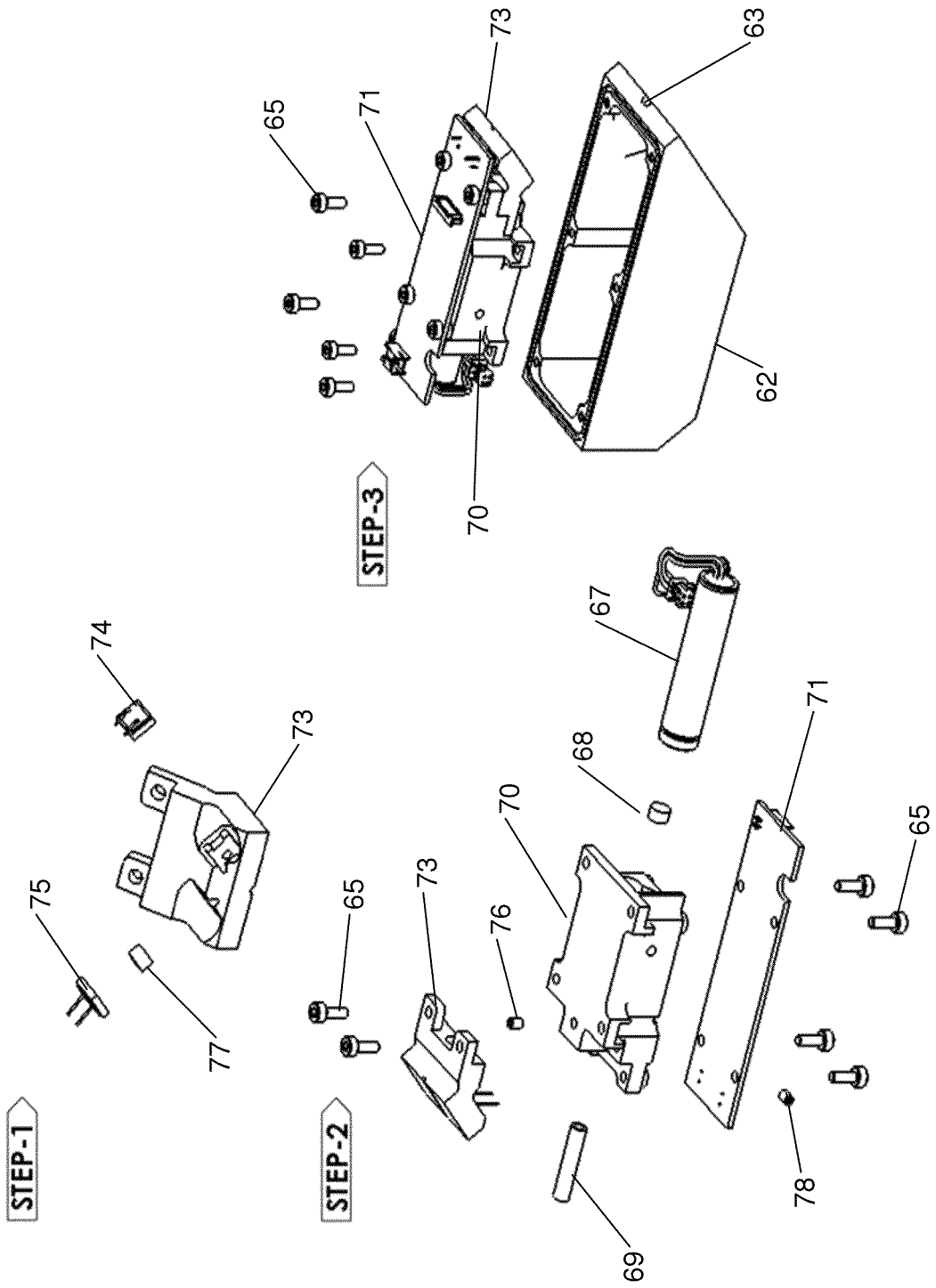
FIG. 7B is an exploded view of the components of an IS module of an embodiment.
Figure 7C:
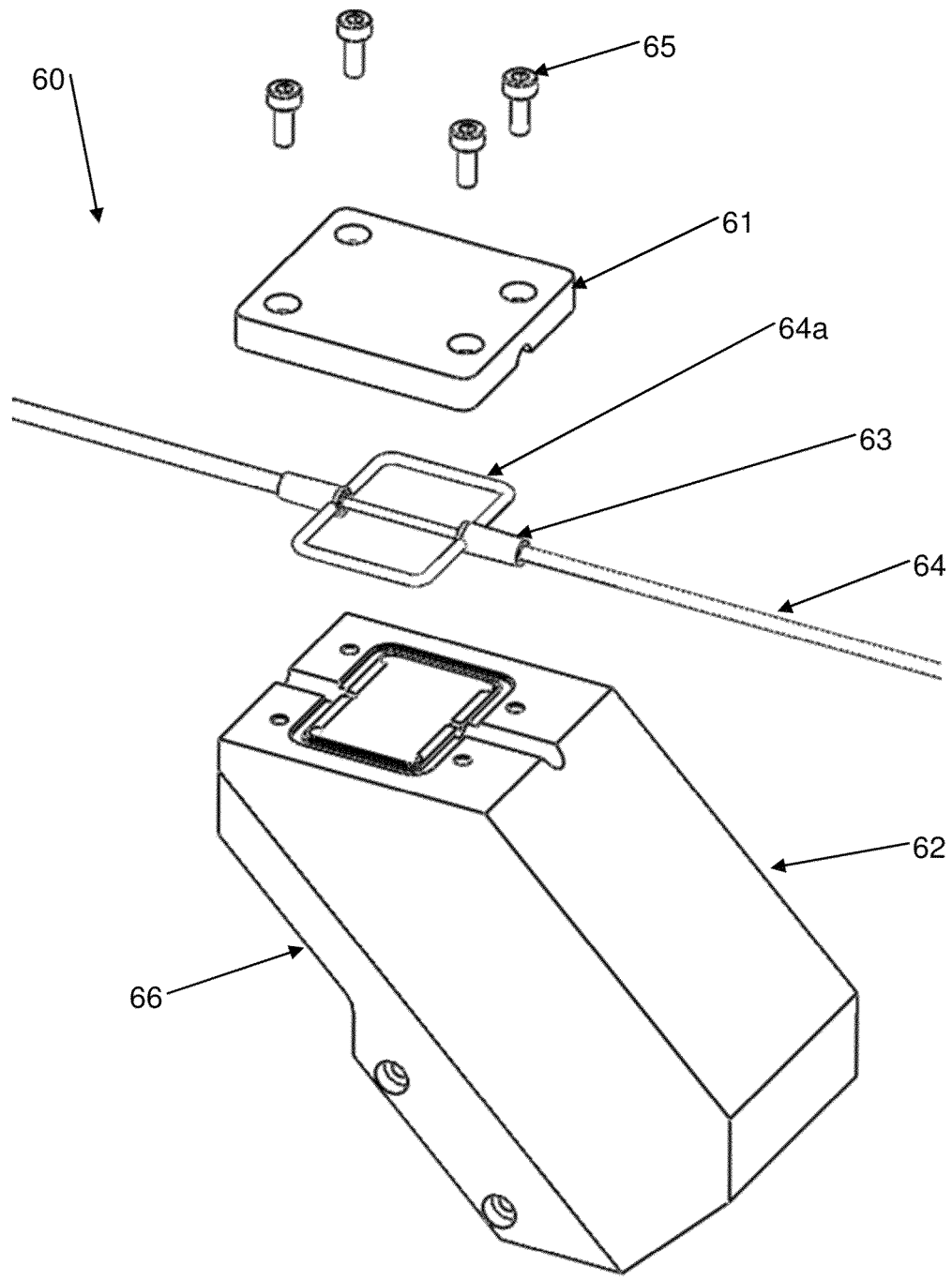
FIG. 7C is an exploded perspective view of the internal components of an IS module of an embodiment.

With reference to FIGS. 7A-7C, FIG. 7A is a cross-section view of an IS module of an embodiment. FIG. 7B is an exploded view of the components of an IS module of an embodiment. FIG. 7C is an exploded perspective view of the internal components of an IS module of an embodiment. In certain embodiments, an IS module 60 is a flow-through cell having a housing 62 with a tubing assembly 64 and at least one opening 63 in the housing 62 to facilitate the entry and exit of the tubing assembly 64 to and from the IS module 60, as shown in FIGS. 7A-7C. The IS module can also include a first photodiode 74 and a second photodiode 75 connected to and powered by a printed circuit board (PCB) 71. Within the housing 62 of the IS module 60, a laser mount 70 holds a laser 67 and an excitation filter 68, which is used to remove light at wavelengths may interfere with fluorescence measurement. The laser mount 70 also has a small aperture (not depicted) at one end through which the laser light exits as it is guided by a light pipe 69. The light pipe 69 directs the laser light to a portion of the tubing assembly 64. When the laser light is incident the tubing assembly, both the laser light and laser-induced fluorescent light can be detected by the first 74 and the second 75 photodiodes. Light pipe 69 is secured to laser mount 70 using screw 76.

The IS module 60 can be formed from housing members including a housing 62, at least one panel 66 and at least one cap 61. The at least one cap 61 also is removable to aid in assembly of the IS module 60. The at least one panel 66 and the at least one cap 61 can be removable and therefore securable to the housing 62 with standard fasteners 65. Screw 78 secures laser 67 to laser mount 70.

When present the at least one cap 61 can be positioned over an uncovered portion of the housing 62 through which the tubing assembly 64 passes. The tubing assembly 64 can be made of a variety of suitable plastic materials. For example, in one embodiment, the tubing assembly 64 can be made from a clear FEP (fluorinated ethylene propylene) with an internal diameter of 0.020". The tubing assembly can be held in place with vacu-tight fittings (not shown) on either side of the housing 62. To prevent light from entering the housing 62, black heat shrink (on the probe side) and black FEP tubing (on the ECL detection side) covers the clear FEP tubing. It is contemplated that other methods can be used to light seal the tubing assembly such as applying an opaque sleeve and coating, painting or tinting the tubing assembly in opaque light blocking materials. The sizing of the aperture 63 in housing 62 correlates to the size of the tubing. In particular, the opening 63 is big enough to allow the tubing assembly 64 to pass through, yet small enough that it can be easily light sealed with a fitting or gasket.

Alternatively, underneath the at least one cap 61, a gasket 64a can be positioned within a recess of the housing 62. The gasket 64a can be formed to fluidically seal the tubing assembly 64 as it passes through the at least one opening 63 in the housing 62. The gasket 64a also functions to form a light tight seal for the contents of the tubing assembly 64, particularly during the IS measurement.

The housing 62 can be comprised of an opaque material that is sturdy and supportive. Suitable materials include, but are not limited to, aluminum, steel, or brass. The inside surfaces of the housing can be painted black or coated with a seal or tint to absorb stray light that may find a way into the IS module. It is important to have a light tight surrounding to receive an accurate light reading within the IS module.

The light source can be derived from a laser 67. The laser 67 can fit inside a drilled out cylindrical hole of the lasermount 70, which in turn is positioned in the housing 62, an example of which is shown in FIGS. 7A and 7B. Light from laser 67 is filtered using excitation filter 68 which is used to remove light at wavelengths may interfere with fluorescence measurement. For example, in certain embodiments, before striking the tubing assembly 64, the laser light passes through a 632 nm band pass filter, light pipe 69 and exits the IS module through a round 0.065" aperture. It is contemplated that depending on the fluorophore, different lasers can be used within the IS module. For example, when APC or Sky Blue is the fluorophore, the IS module can employ a 635 nm laser light source.

The printed circuit board 71 can be mounted to the laser mount 70 and can hold the first and second photodiodes 74, 75 (see, e.g., FIGS. 7A and 7B). The first photodiode 74 detects the fluorescent light. The second photodiode 75 measures the power of the laser light. The first and second photodiodes 74, 75 are mounted on opposite sides of a detector mount 73 attached to the printed circuit board 71. Emission filter 77 is attached to first photodiode 74, and used to remove light of wavelengths that may interfere with the fluorescence measurement. For example, emission filter 77 is a color glass filter RG695. The first and second photodiodes are mounted on opposite sides of a diode mount attached to the printed circuit board. Both the fluorescent light as well as the laser light can be detected with photodiodes which converts the light into a measurable electrical signal through connector 72. As the laser strikes the tubing assembly the first photodiode measures and detects the fluorescent light emitted by the fluorescent beads flowing through the tubing assembly. Concurrently, the second photodiode measures and detects the laser light originating from the tubing assembly.

Figure 7D:
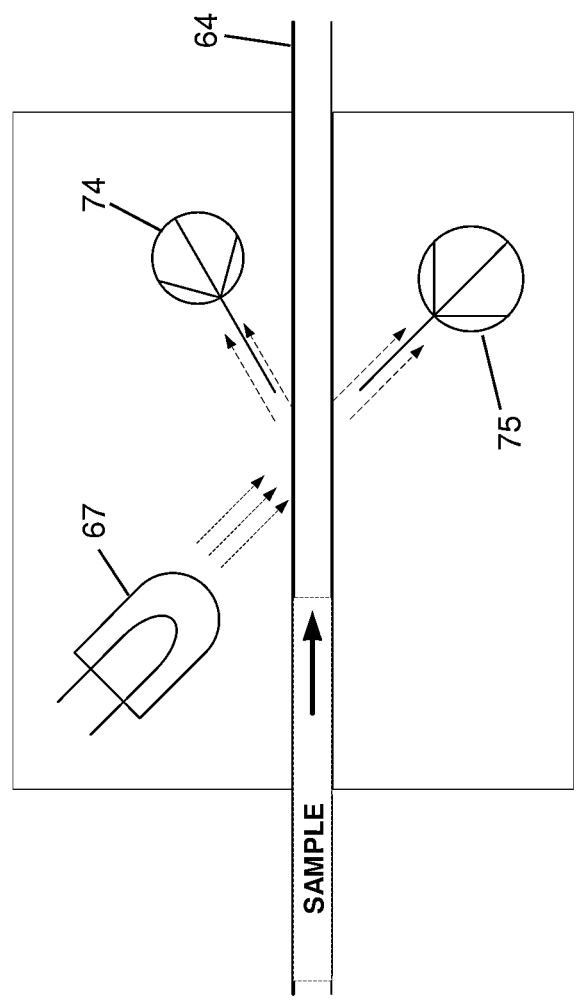
FIG. 7D is an illustration of the transmission and reflection of a light source within an IS module of an embodiment.

FIG. 7D provides a depiction of optical path of the laser light within the IS module in an embodiment. The light from laser 67 passes through excitation filter (not shown) and is guided through the light pipe (not shown) onto the tubing assembly 64 containing the sample. The laser light beam is incident the tubing assembly at a 45° angle. The photodiodes are oriented 45 degrees respect to laser beam, and 90° in rotation with respect to each other around the tubing.

Certain embodiments provide a fluorescence based, non-interfering method to detect and measure ECL bead recovery, if any, during the processing of a cartridge, comprising the steps of illuminating with a light source a processed sample flowing through a tubing assembly; wherein the sample contains fluorescent labeled beads and ECL labeled beads and the light source is of a specific wavelength to excite the fluorophore; detecting fluorescent light emitted by the fluorescent beads flowing through the tubing assembly; converting the fluorescent light into measurable electrical signals; processing the electrical signals to calculate ECL bead recovery by comparing the fluorescence signal to a fluorescence signal from a standardized quantity of fluorescent bead. When certain conditions exist where the bead recovery is below normal acceptable limits, the IS method provides a failsafe mechanism to prevent reporting erroneous results. When certain conditions exist where the bead recovery is within normal acceptable limits, the IS method provides an improvement is precision and accuracy results.

Electrochemiluminescence (ECL) Detection System Improvements.

Electrochemiluminescence (ECL) is a quick and sensitive technique. It has been described in detail in the following U.S. Pat. Nos. 5,714,089, 6,165,729, 6,316,607, 6,312,896, 6,808, 939, 6,881,589, 6,881,536, and 7,553,448, all of which are herein incorporated in their entirety. It is contemplated that a label is an ECL label and the presence of the bound labeled molecule is detected by ECL. ECL signals are generated by a redox reaction between an ECL label with a substrate. In certain embodiments the ECL label is a ruthenium-containing reagent. One example of a suitable ECL label is Tris(bypyridine)ruthenium(II) [Ru(bipy)3]2+, also referred to as TAG. In certain other embodiments, the substrate is tripropylamine (TPA). One advantage of the method of using ECL is improved speed of the assay.

ECL technology is advantageous in that it is a regenerative process, in which a luminescent signal can be generated by a reaction involving a ruthenium (Ru) conjugate at the surface of an electrode (DEAVER, DR., "A New Non-Isotopic Detection System for Immunoassays," Nature 377(6551):758-760 (1995)). A magnet usually below an electrode will attract the magnetic beads, pulling down the Ru-tagged complex near the electrode. The Ru can then be oxidized. Oxidized tripropylamine (TPA) reacts with the oxidized Ru, which then emits a photon. The redox reaction between Ru and the substrate tripropylamine (TPA) that occurs only in the electric field near the electrode is a regenerative process, which allows for an ECL signal that undergoes amplification over time. Because photons can only be generated near the electrode surface, electrochemiluminescence only occurs when the Ru is brought into proximity with the electrode by the magnet; thus, background is reduced.

Some embodiments provide a new and improved ECL detection system for diagnostic applications. The improvements include, but are not limited to: (I) improvements in the design and use of gasket materials by which a precisely sized measurement containment area is established in order to increase the accuracy and precision of sample measurements; (II) a novel use of differential compliance to enable mounting and precise spacing of two or more electrodes while also creating feature seals to prevent leaking; and (III) a new method to accomplish light sealing of an enclosure by means of a substantially opaque printed circuit board while at the same time permitting electrical connections and/or the introduction of other components between the inside and outside of the light enclosure; (IV) a new method to accomplish light sealing of an enclosure by using an opaque material beneath enclosure openings, such as, fluidic ports that connect fluidic pathways inside and outside of the light enclosure.

Accordingly, in certain embodiments, the diagnostic system includes an ECL detection system having an ECL detection module (also referred to as a flow cell) with fluidic and electrical connections to the closed fluidic pathway, such as that previously discussed (not depicted). For example, in some embodiments, and as depicted in FIGS. 8A-8E, an ECL detection system can include an ECL detection module 80 having an enclosure made of a top 82 and a base 84, wherein the upper surface of base 84 is flat and forms a working surface. The top 82 can be attached to the working surface of base 84, thereby forming a cavity of precise height Z.

The ECL detection module 80 also can have a first electrode 86 and a second electrode 87 that are stacked upon each other and separated by a first gasket 88. The base 84 can support the first electrode 86 and the electrode/gasket stack. First gasket 88 is sufficiently thick and compliant to require forceful closure of top 82 onto base 84 and presses electrodes 86 and 87 firmly against the cavity walls, and thereby creates a precise predetermined separation gap H between the first and second electrodes 86, 87.

A change in compliance can be associated with a change in thickness or a change in hardness between two different materials, or a change in geometry of the compressed area between two different materials or two of the same materials. Thus, the term compliant can refer to the displacement of material for a given load and it can also refer to the softness of a material wherein a material can be more compliant due to the material being softer.

Figure 8A:
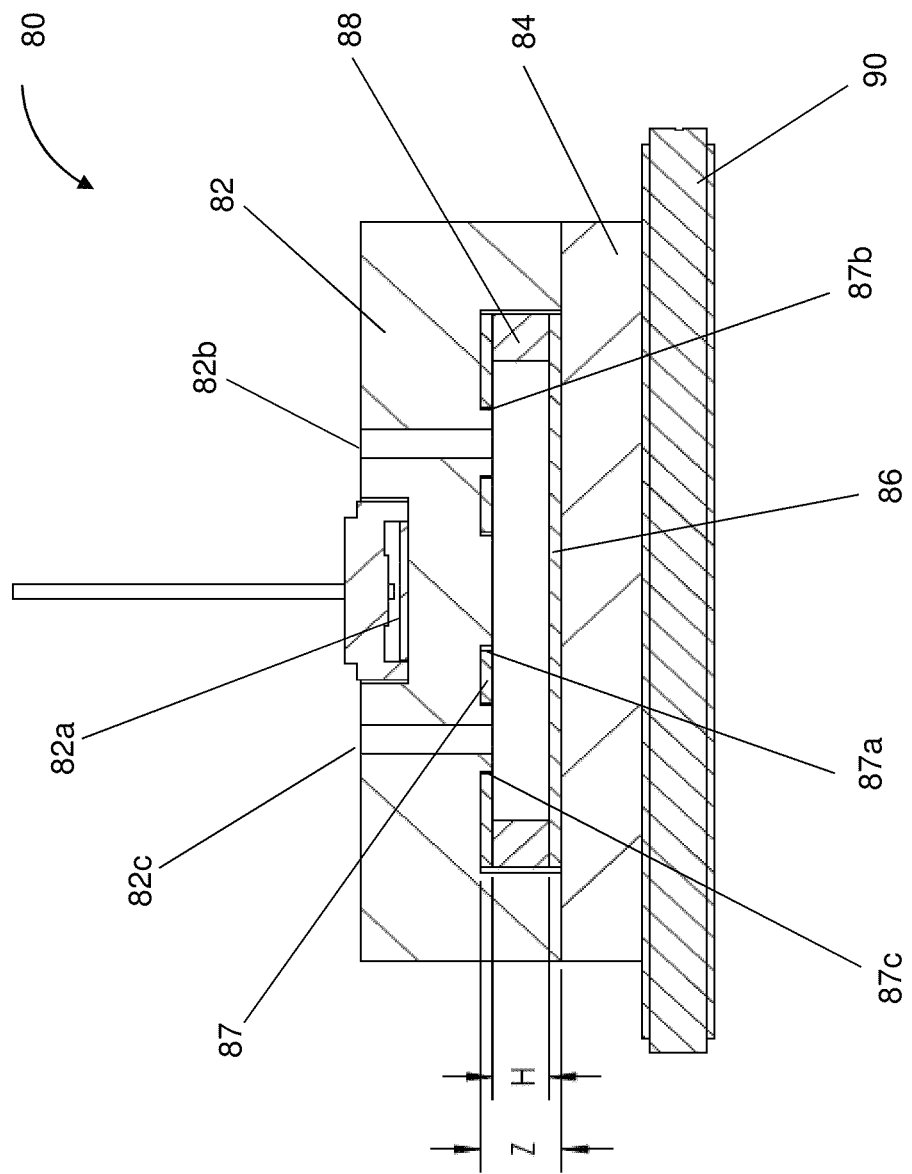
FIG. 8A is a cross-section view of an electrochemiluminescence (ECL) detection system of an embodiment.

A cut out opening 87a in the second electrode 87 permits light to pass through the electrode during the ECL measurement. The cut out 87a in the second electrode 87 aligns with a transparent window in top 82, such that light from the ECL reaction can be measured by the photodetector 82a. Fluids must enter and exit the measurement containment area to setup the ECL reactions and flush the cell of prior reactants. FIG. 8A shows fluid inlet and outlet ports 82b and 82c aligned to two additional apertures 87b and 87c in electrode 87. The ECL detection system also includes a printed circuit board 90 that is positioned next to the base 84 and connects the components within the ECL detection system electrically.

The first and the second electrodes 86, 87 can be made from a variety of conductive noble metals, including, but not limited to, platinum, gold, iridium, palladium, osmium, and alloys thereof. The first and second electrodes 86, 87 may also be made of conductive non-metals, such as carbon. The top 82 can be made from a variety of durable materials, including, but not limited to, acrylic, polyether ether ketone and acetal polymers. The base 84 can be made from a variety of durable materials, including, but not limited to aluminum, copper and stainless steel.

Figure 8B:
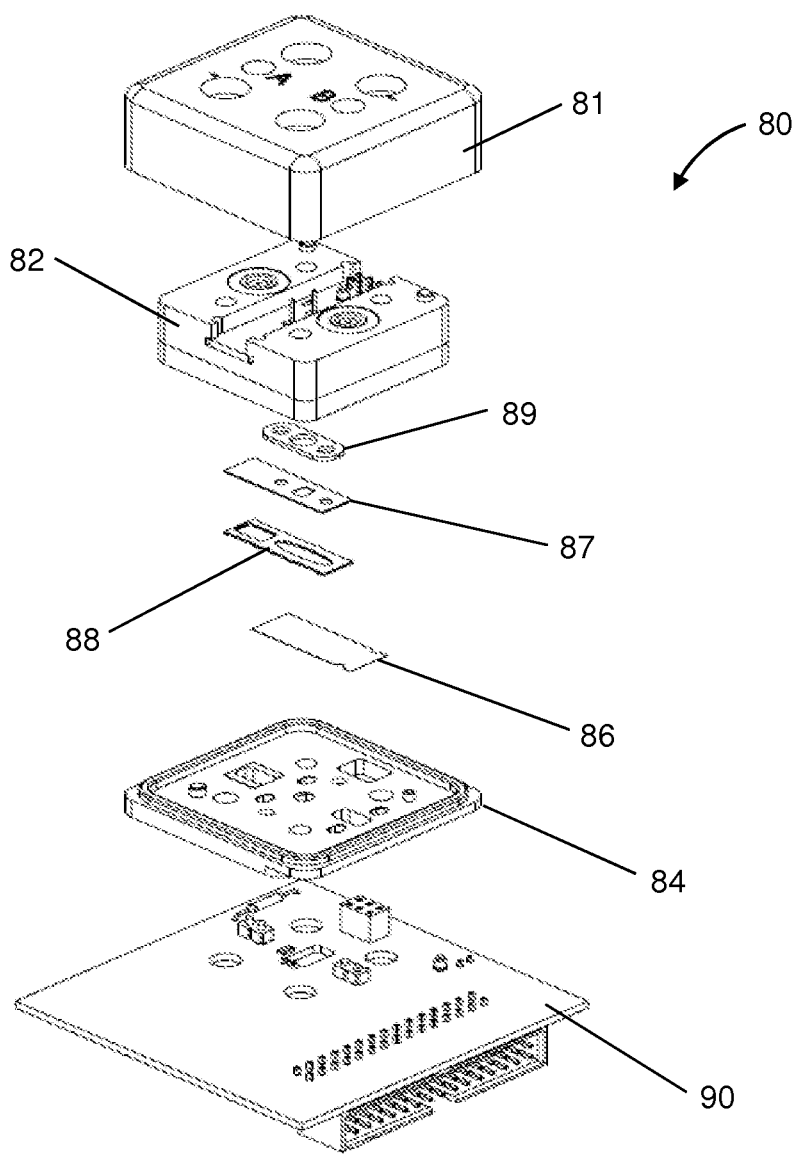
FIG. 8B is an exploded view of an ECL detection system of an embodiment.
Figure 8C:
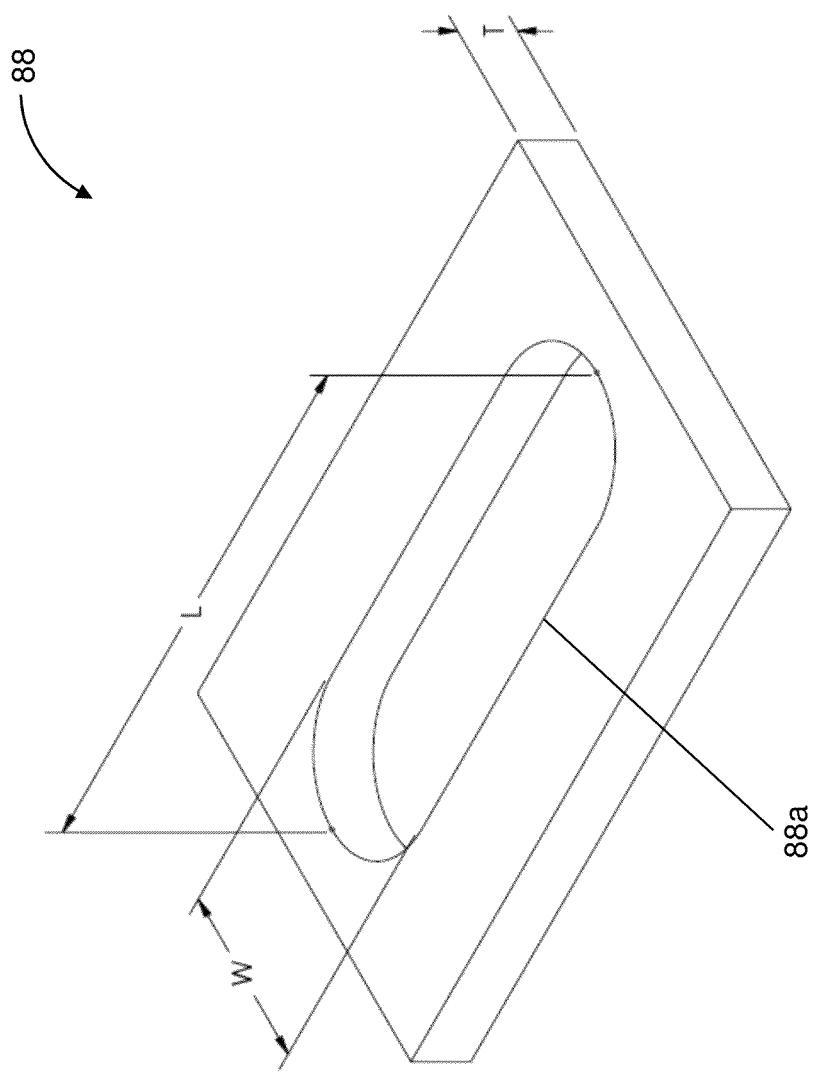
FIG. 8C is a perspective view of a gasket of an ECL detection system of an embodiment.

The gasket 88 has an elongated cutout 88a shown in FIG. 8C. When gasket 88 is clamped between the electrodes 86 and 87, the elongated cutout 88a creates a measurement containment area (i.e., the ECL reaction chamber). The measurement containment area must be sealed liquid tight and airtight, so it is desirable to have a gasket that is made from a compliant material that seals against the electrode surfaces. Accordingly, gaskets can be made from a variety of compliant materials including, but not limited to, perfluoroelastomers such as Chemraz 631 or Kalrez 2037, fluoroelastomers, nitrile and silicone rubbers, and polymers such as polytetrafluorethylene (PTFE) and polychlorotrifluoroethylene (PCTFE). Electrode surfaces are only exposed to chemical fluids within the gasket cutout 88a, and consequently only this portion of the electrode surfaces are active during ECL reactions.

Consistent ECL reactions and measurements among instruments requires the measurement containment area geometry and electrode spacing to be uniform and precise from flow cell to flow cell. When the gasket 88 thickness T is compressed between the electrodes, the cut-out or gasket opening 88a distorts laterally and dimensions L and W are diminished from the uncompressed state. Thus it is necessary to control both the gasket thickness compression and the gasket opening distortion to achieve precise flow cell geometry and electrode spacing. The cavity pocket depth Z in FIG. 8A is precision machined in top 82 to ensure uniform spacing between the electrodes 86, 87 and consistent clamping of gaskets. In addition, the thickness of electrodes 86 and 87 are made to precision tolerances.

Compliant materials, when compressed across their thickness, spread laterally. Thus, cut-out or gasket opening 88a closes down as gasket 88 is clamped between the electrodes. Limiting the final clamped dimension of cut-out 88a requires tight control of the gasket thickness, and can minimize variations of the measurement containment area geometry. Compliant materials used to create gaskets are often fabricated from sheets or slabs that are molded, extruded, calendered or cut into appropriate thicknesses by slicing or skiving. However, the gasket thickness precision is generally inferior to the tolerances of other rigid components used in the system.

Gaskets of varying thicknesses cut to the same inside profile 88a will, when compressed, result in different-sized internal areas, which can in turn result in undesirable ECL signal variations when used in an ECL detection system. It is desirable to improve the measurement containment area geometry precision by sizing the gasket cutout 88a in proportion to the thickness of the gasket, such that when the first gasket is constrained to a fixed compression distance, the desired size measurement containment area is achieved. Sizing the inside profile 88a based on the thickness of the gasket raw material, while taking the compressive characteristics of the material into account, results in maintaining the compressed gasket cutout area to an acceptable tolerance.

Accordingly, the precise, predetermined separation gap H provides the desired accuracy of an ECL measurement. The compliant gasket provides expansive force to maintain a precise distance between the electrodes as is required in order to obtain precise ECL measurements. As ECL measurements depend on both the distance H between the electrodes and the area of the exposed portion of the electrodes, the cutout in the gasket that forms the measurement containment area must be precise. In order to establish a precise electrode exposure area after compression of the first gasket 88 (as shown in FIGS. 8A and 8D), the size of the cutout that will form the measurement containment area is adjusted based on the thickness T of the raw material of the first gasket and the compressive characteristics of the raw material.

For example, in FIG. 8C, the first gasket 88 is depicted as being formed from a raw material of nominal thickness having a thickness tolerance of ±0.002 in. This depicted first gasket requires that a different size L×W cutout be made for each 0.001 in. of thickness variation in order to achieve adequate precision of the compressed cutout area. Alternately, the L×W cutout dimensions could vary continuously with the gasket material thickness deviation from nominal thickness. Gasket material characteristics and thickness tolerances range widely, and the particular design requirements of the measurement device will determine how the gasket cutout dimensions must be adjusted to achieve adequate precision of the clamped, in situ gasket cutout area.

In FIG. 8A, a first (cell) gasket 88 seals the perimeter of the measurement containment area against the electrodes, but no seal is shown around the window aperture 87$a$ or the fluid port apertures 87$b$ or 87$c$ in electrode 87. These areas are often sealed by cementing the second electrode into the body with epoxy, acrylic or other permanent adhesives. The adhering process is slow, messy, difficult and time consuming. In addition, the cemented joints erode away during flow cell use, causing the second electrode to delaminate or develop leaks and servicing or replacement of individual components is made difficult or impossible. Some embodiments do not require adhesives to create the fluidic seals within the ECL detection system. These embodiments also maintain the precise positioning of the components relative to each other as is required to make an ECL detection system precise and accurate.

Figure 8D:
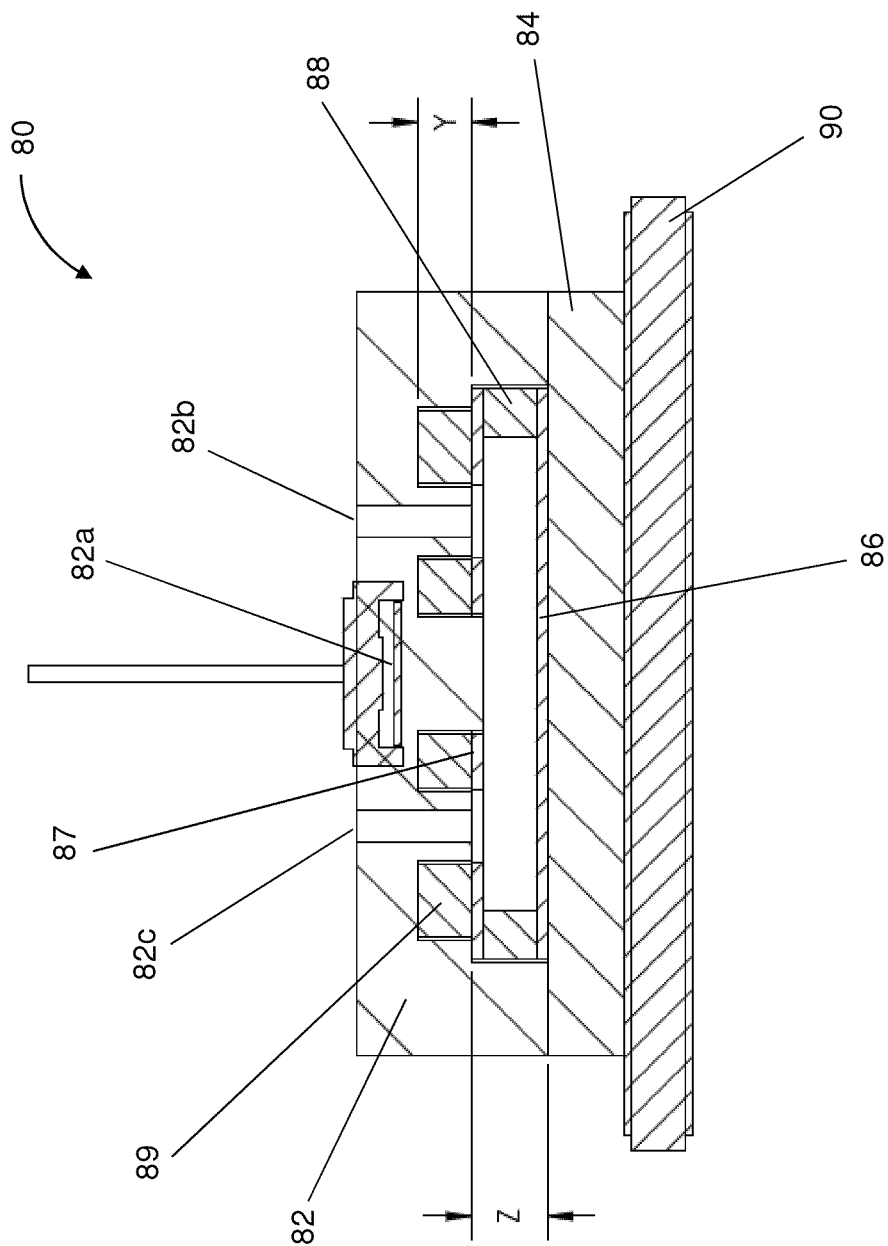
FIG. 8D is a cross-section view of an ECL detection system of an embodiment.

Accordingly, in certain embodiments, for example as shown in FIG. 8D, a second gasket 89 backs at least one of the electrodes in order to establish fluidic sealing. The second gasket 89 can be more compliant than and have a lower compressive force than the first gasket 88 so as not to change the separation gap H set for the first and second electrodes 86, 87 by the first gasket 88. This second gasket 89 eliminates the requirement to adhere the electrodes to the enclosure with adhesives such as epoxy, improving the ease of assembly, the reliability and longevity of the seal and makes servicing components practical.

The light levels generated by ECL are low and photodetector 82$a$ is very sensitive to light. FIG. 8B shows an example of how the ECL detection module 80 can be enclosed in an opaque case 81 and the base 84 to exclude ambient light that would otherwise interfere with detection of the internal low level ECL light signals. The opaque case 81 and base 84 have openings for the required fluidic and electrical connections to the flow cell, and these openings must also exclude ambient light.

For example, the fluidic openings A and B of opaque case 81 are depicted on top of the ECL detection module 80. The fluidic tubing and fittings that fit to these openings are designed to transport fluids, and often have limited ability to block ambient light. Ambient light travelling through the fluidic tubing and connections may enter the ECL detection module 80 through the fluidic openings A and B of opaque case 81, and pass through the inlet and outlet ports of the opaque top half of flow cell top 82 seen in FIG. 8B which blocks this light from reaching the detector.

In still other embodiments, the opaque enclosure of the ECL detection system can further include at least one opening 94 to permit electrical connections to be introduced into the enclosure (as shown in FIG. 8E). The electrical connections 93 are provided by the printed circuit board (PCB) 90. The printed circuit board 90 may be made from an inherently opaque material, or can have an opaque coating 91, such as solder mask or screen printed layers, on its surface to prevent light leakage into the enclosure through the at least one opening 94. Examples of inherently opaque materials and opaque coatings include black glass fiber/epoxy laminates and black matte liquid photo-imageable solder masks meeting IPC SM 840 Qualification and Performance Standards for permanent solder mask. The printed circuit board 90 can also include an internal or external conductor layer 92 which can further block undesired light entry.

There are various configurations that can be used when constructing an ECL detection system and those described herein and depicted in the figures are merely for illustrative purposes and not meant to be limiting. It is contemplated that some of the configurations may be combinations of all or part of the embodiments described herein. Some of the various embodiments include an ECL detection system 80 comprising an enclosure having a top 82 and a base 84. A stack is formed within the enclosure with a first electrode 86, a second electrode 87 and a first gasket 88 sandwiched between the electrodes.

A cavity or gap formed by the pieces of the enclosure define the desired gap (Z) in which to house the electrode/gasket stack, thereby establishing the distance between the electrodes. The first gasket 88, made of compliant material, has a thickness greater than the desired distance between the first and second electrodes 86, 87. A measurement containment area of precise size is defined by a cut-out 88$a$ once the first gasket 88 is compressed. The first gasket 88 is fabricated with a cut-out 88$a$ that has been sized such that the known compression height (Z) of the electrode/gasket stack and gasket raw material thickness will produce a measurement containment area of the desired size when compressed. The size of the measurement containment area is determined by many factors including, but not limited to, the thickness of the raw material of the first gasket 88 and the compressive characteristics of that raw material; the cutout geometry, WE and CE thickness and body pocket depth Z. A transparent window for ECL detection may be provided through an opening in the second electrode 87.

Another embodiment provides an ECL detection system comprising an enclosure having a top 82 and a base 84. A first electrode 86 forms a stack with a second electrode 87 with a first gasket 88 sandwiched between them within the enclosure. A cavity or gap is formed by a pocket in the top 82, which defines in part the desired gap (Z) in which to house the electrode/gasket stack, thereby establishing the distance between the first and second electrodes 86, 87. The second electrode 87 has cutout openings for ECL detection and two fluidic ports. A second cavity in the top houses a second gasket 89, which has openings for two fluidic ports 82$c$, 82$b$ and a transparent window 85 for ECL detection in top 82. The second gasket 89 fluidically seals the cut-out openings 88$a$ in the second electrode 87. The compressive characteristics of the first and second gaskets 88, 89 along with the height of the gaps (Y) and (Z) are selected such that the compressive force of the second gasket 89 is adequate to create the desired fluidic seals without displacing the second electrode 87, and thereby maintains the desired gap between the first and second electrodes 86, 87 created by the first gasket 88.

Still another embodiment provides an ECL detection system comprising an enclosure having a top 82 and a base 84. A first electrode 86 forms a stack with a second electrode 87 with a first gasket 88 sandwiched between them within the enclosure. A cavity or gap is formed by a pocket in the top 82, which defines in part the desired gap (Z) in which to house the electrode/gasket stack, thereby establishing the distance between the first and second electrodes 86, 87. A second cavity in the top houses a second gasket 89 which forms fluidic seals to two fluidic passages. A transparent window 85 for ECL detection may be provided through an opening in the second electrode 87 and the second gasket 89. Additional gaskets (not shown) behind the second electrode 87 may be used to create additional fluidic seals under the same constraints as the second gasket 89. The compressive characteristics of the first and second gaskets 88, 89 along with the height of the gaps (Y) and (Z) are selected such that the compressive force of the second gasket and/or additional gaskets are adequate to create the desired fluidic seals without displacing the second electrode and thereby changing the desired gap between the first and second electrodes created by the first gasket.

Still another embodiment provides an ECL detection system comprising an enclosure having a top 82 and a base 84, and a first electrode 86 and a second electrode 87 stacked upon each other with a first gasket 88 sandwiched between the electrodes. The first gasket 88 provides a mechanism to maintain relative positions between the components within the enclosure. At least one opening 94 in the base provides for connections of electrical connectors 93 or other components between the exterior of the enclosure and components within the enclosure. At least one of the electrical connectors 93 can establish electrical contact with the first electrode 86. A printed circuit board 90 forms a portion of the light tight enclosure, specifically around the at least one opening 94. An inner conductor layer 92 within the printed circuit board 90 creates a substantial barrier to undesired light, as does screen printed layers 91 on the surfaces of the printed circuit board 90.

Still another embodiment provides an ECL detection system comprising an enclosure having a top 82 and a base 84, where it is a light tight enclosure and a portion of the enclosure is established by a printed circuit board 90 used to make electrical connections between components within and outside of the enclosure. A first electrode 86 and a second electrode 87 are stacked upon each other with a first gasket 88 sandwiched between the electrodes. The printed circuit board 90 can be made of material that is inherently opaque of have one or both of (a) a light shield in the form of either an internal or surface conductor layer, and (b) a light shield in the form of a polymeric layer on either or both of the printed circuit board faces where the polymeric layer is substantially opaque. The resulting enclosure is light sealed while allowing electrical connections through the openings in the enclosure.

The various embodiments described herein provide improvements in the accuracy and precision of an ECL detection system by any one or any combination of the following: (1) use of a compliant material used to define the measurement containment area; (2) sizing an uncompressed cutout of a compliant gasket which will define the measurement containment area to a desired size after compression; (3) varying the size of the cutout relative to the compliance characteristics and thickness of the raw gasket material; (4) the use of differential compliance of gaskets and/or other compliant mounting components; (5) the use of differential compliance of gaskets and/or other compliant mounting components in order to create a gap of a desired size between one or more electrodes; (6) the use of differential compliance of gaskets and/or other compliant mounting components in order to create a gap of a desired size between one or more electrodes where a compliant gasket defining a measurement containment area is made of a compliant material with a known stiffness and one or more additional gasket(s) is/are used to seal one or more of the electrodes while not changing the previously mentioned gap by having a lesser stiffness; (7) the use of a substantially opaque screen printed mask on a printed circuit board that comprises part of a light sealing system; (8) the use of a relative opaque screen printed mask on a printed circuit board that comprises part of a light sealing system thereby allowing the establishment of electrical communication between the inside and outside of the light sealing system; (9) the use of a substantially opaque screen printed mask on a printed circuit board in conjunction with internal conductor planes of the printed wiring board that comprises part of a light sealing system; (10) and/or the use of a substantially opaque screen printed mask on a printed circuit board in conjunction with internal conductor planes of the printed circuit board which comprise part of a light sealing system thereby allowing the establishment of electrical communication between the inside and outside of the light sealing system; (11) the use of a printed wiring board made of relatively opaque material that comprises part of a light sealing system, thereby allowing the establishment of electrical communication between the inside and outside of the light sealing system; (12) the use of a printed wiring board made of relatively opaque material in conjunction with internal conductor planes of the printed wiring board that comprises part of a light sealing system.

Pump Instrument Improvements.

The diagnostic system can also include a pump. The diagnostic system provides methods to minimize communication of gasses and liquids between the inlet and outlet ports of a dual-action piston pump (e.g., a pump in which the piston serves to move fluids into and out of the chamber and also serves as the means of establishing communication between the chamber and one of two or more ports by means of both linear and rotational action). Because of the properties of the updated design, improvements are realized in the precision and accuracy of aspiration and dispensing to and from the pump.

Some embodiments further provide a means to stop or at least reduce communication between the input and output ports of a pump. Also provided is a means to stop or at least reduce communication between the chamber of a pump and either or both of the pump's input and output ports. Additionally, a means to improve the aspiration and dispensing accuracy of a pump is provided where the aspiration and dispensing precision of a pump is also improved.

Certain embodiments provide an improved dual-action piston pump that can prevent or reduce undesired communication between (i) the input and output ports of a pump; (ii) the chamber and input port of a pump; and/or (iii) the chamber and output port of a pump. The improved dual-action piston pump can also improve aspiration and dispensing accuracy and also dispensing precision by preventing or reducing communication between any of the input port, output port, or chamber of a pump.

Figure 9:
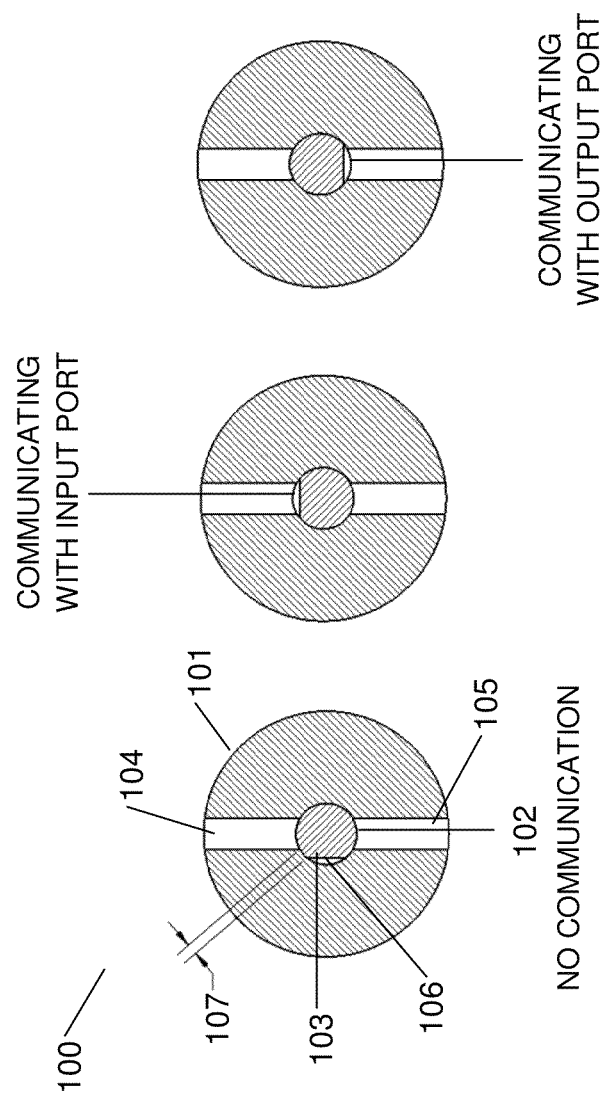
FIG. 9 is a series of cross-section views of fluidic communications of a pump system of an embodiment.

An embodiment of the diagnostic system provides a pump 100, for example, such as the cross-section of a pump shown in FIG. 9, comprised of a cylinder 101 made of a zirconia ceramic which houses a piston 102, also made of a zirconia ceramic, and serves as a fluid containment chamber 103 during pumping. The cylinder 101 has a fluidic pathway that serves as an input port, 104 and a second fluid pathway that serves as an output port 105. The input port 104 and output port 105 fluidic pathways breach the cylinder wall thereby establishing a communication path for fluids. The input port 104 and the output port 105 are situated diametrically opposed to each other within the cylinder wall. The piston 102 is sealed to the cylinder 101 by close tolerance matching between itself and the cylinder bore 101 with a nominal clearance ranging from about 1.75 microns to about 2.75, such as, for example, about 2 microns, or about 2.5 microns.

A close fit created by this configuration creates a substantially watertight seal between the cylinder 101 and piston 102. Once the gap between the piston 102 and the cylinder 101 is wetted, the seal becomes airtight. The terminal end of the piston 102, the end which faces into the chamber, is flatted on one side along between about 0.6 inches and about 0.75 inches of its length. The flat 106 allows communication between the port 104 or 105 that the flat 106 faces and the fluid containment chamber 103. The small wetted gap between the non-flatted side of the piston 102 and the cylinder wall produces a seal preventing communication of fluid between the fluid containment chamber 103 and that port effectively closing it. As a pressure differential develops between the fluid containment chamber 103 and the closed port, the wetting fluid between the piston 102 and cylinder 101 becomes inadequate to prevent some leakage to the closed port. Decreasing the width of the flat 106 increases the distance between the fluid containment chamber 103 and the closed port thereby preventing or reducing the undesired communication. Using the above design configuration the pump can aspirate or dispense out of either port without undesired communication with the opposite port.

The sealing distance 107 between the input port 104 or output port 105 on a commercially available pump 100 may be as small as 0.006 inches depending on the orientation of the flat 106. In one embodiment, reduction of the size of the flat 106 increases the sealing distance 107 to 0.044 inches improving sealing by a factor of about 7.33. In the some embodiments, rotational positioning of the flatted piston 102 is about ±0.002 inches allowing the sealing distance 107 to be as small as 0.004 inches, in which case the sealing improves by a factor of about 10.5 with the reduced width flat 106. It is contemplated that the sealing distance 107 can be up to about 0.090 inches with an improvement of about 22.25. It is further contemplated that the flat size could be further reduced, limited only by the requirement that the cross-section of the flat is not smaller than the cross-section of the port in order to not cause pressure restrictions within the pump chamber. A housing in the form of a cylinder 101 is constructed of a suitable material such as a plastic, ceramic or metal. A bore is created within the cylinder 101 to house a piston 102 made typically of the same material as the cylinder 101 or of a material with a close thermal expansion coefficient to prevent binding due to differential thermal expansion. The bore and piston 102 are sized to produce a clearance small enough to prevent liquid leakage but large enough to allow free movement of the piston 102 within the cylinder 101. The portion of the cylinder bore which is not occupied by the piston 102 creates a fluid containment chamber 103. At least one fluidic pathway, including input port(s) 104 or output port(s) 105, pierce the wall of the cylinder 101 to establish communication channels into and out of the cylinder 101. A flat 106 is sized and formed onto one side of the piston 102, so that when facing a fluidic pathway of choice, a fluidic communication is established between the fluid containment chamber 103 and the selected fluidic pathway while blocking communication to the other fluidic pathway(s).

The flat size is governed by several driving factors including (a) the flat 106 should be sized to create a path between the selected fluidic pathway and the fluid containment chamber 103 that has a cross-section that is greater than or equal to the cross-section of the fluidic pathway so as not to restrict fluid flow; and/or (b) the flat 106 should be sized to maximize the seal distance between the edges of the flat and the unselected fluidic pathway(s) so as to prevent undesired communication of fluids.

The stroke of the piston 102 can be limited so that the non-flatted portion opposite the flat 106 never reaches the unselected fluidic pathway, else unrestricted undesired communication between the fluidic pathways will occur. It is contemplated that there may be certain circumstances where this communication would be permitted or desired, for example, with a flush of the fluidic system during decontamination.

Due to the geometry of the parts described above, it can be possible to position the flat 106 of the piston 102 within the cylinder 101, such that is not in communication with any port. This arrangement permits creating a pressure differential between the fluid containment chamber 103 and a non-connected port, preferably while there is a compliant medium (such as air) in the chamber. Subsequent establishment of communication with a port will generate a burst of fluid motion into or out of the chamber depending on the polarity of the pressure. Such bursts can be used for manifold fluidic motion purposes such as dislodging debris or unclogging fluidic pathways.

Methods for Calculating and/or Compensating for Backlash in a Fluidic Pump.

Electromechanically driven fluidic pumps, and in particular, positive pressure piston pumps, have backlash. When a direction of the pump is changed from aspirate to dispense or dispense to aspirate, the electromechanical system that drives the piston will start driving the piston in the opposite direction, but the actual engagement of the mechanism where the piston will actually move in the opposite direction may be delayed for the backlash amount. Measuring the backlash amount and adding the backlash amount to the desired volume to compensate for the backlash is a common approach used to compensate for the backlash. However, systems have relied on indirect measurement of the motion of the piston, rather than the direct. Indirect measurements are likely to be less accurate than direct measurements.

Some embodiments provide methods for measuring and, optionally, then compensating for the amount of backlash from motor driven fluid pumps. These methods achieve a highly accurate backlash measurement, by monitoring the changes in pressure occurring in the pump chamber when changing directions, processing the data in firmware and calculating the amount of backlash, and then using the calculated backlash under regular operation when direction is changed. The pressure measurement system described herein is sensitive to detect a pressure change in the chamber for the smallest pump motion, therefore the backlash measurement is very accurate. Indeed, driving the backlash amount from pressure changes is highly accurate and superior to existing methods since it is a direct measure of the fluid that is pumped when the piston direction is changed. Also provided in the present disclosure is an integrated electronics housing a non-volatile memory packaged with the pump, eliminating the need to recalculate backlash when a pump assembly is replaced in an existing instrument.

Some embodiments provide a method to calculate accurate pump backlash. Pump backlash is the amount of volume that is not pumped (i.e., not moving) when a direction (from aspirate to dispense or dispense to aspirate) is changed, although the mechanism moving the pump provides the necessary electrical input to pump that volume. It is then a benefit of the diagnostic system disclosed herein that an accurately measured and compensated backlash will yield to accurate volumes pumped even after changing the direction of pumping. Some embodiments retain the calculated backlash with the pump in an electronic memory instrument, such that when a pump is replaced in the diagnostic instrument in the field, the measurement does not have to be repeated, which will save time and make it easier to do field repairs. Example 5 describes the effects of compensating for the amount of backlash in a pump and showing the improvements made after compensation.

Figure 12:
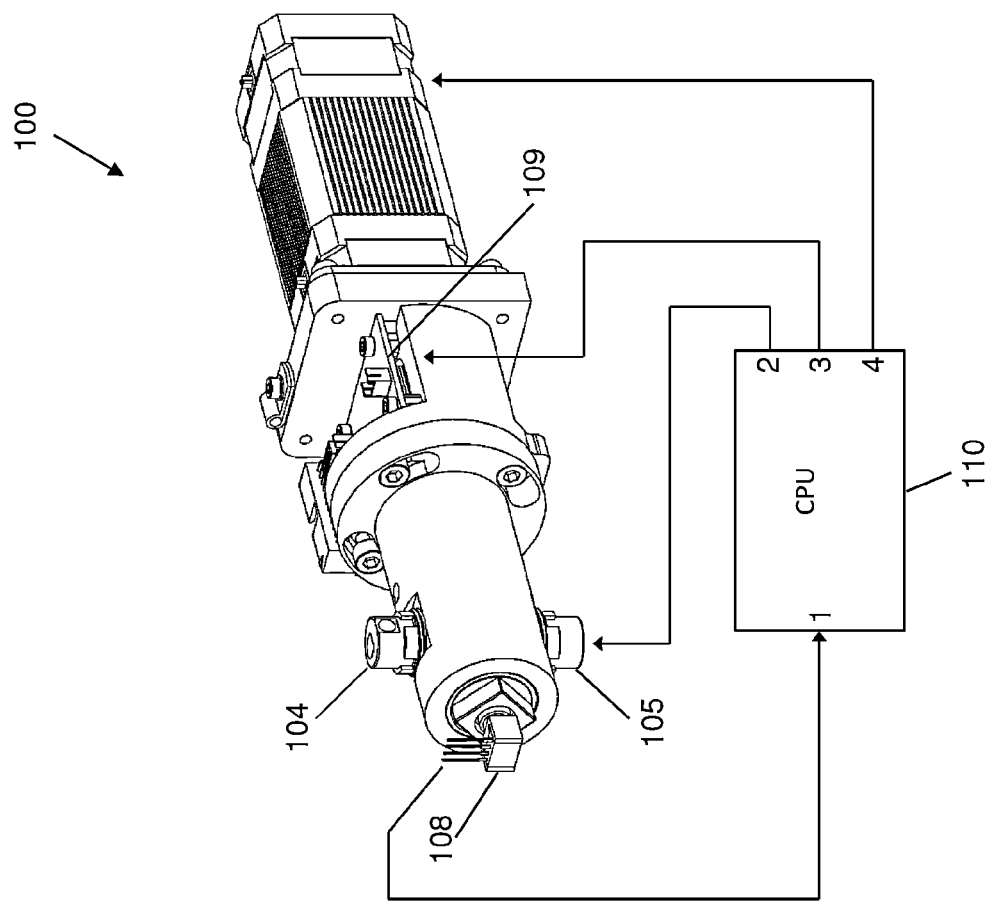
FIG. 12 is a block diagram depicting a pump system of an embodiment.

With reference to FIG. 12, a block diagram of a pump system is depicted. Some embodiments provide a fluid pump 100 for use in high performance systems, such as in diagnostic systems, using micro fluidics and volumes in the micro liter range, where moving fluidics directly or moving air in a closed system in order to move fluidics and position the fluidics accurately while changing direction having a piston movable in a chamber for drawing air or fluid into, pressurizing, and delivering the pressurized air or fluid from the chamber. For example, in FIG. 12, a pressure transducer 108 can be used, directly connected to and measuring the chamber pressure. Electronics 109 can be used to process the signal generated by the pressure transducer 108 and feed it to a microprocessor. The pump motion can be driven by firmware. The firmware converts the requested volume to be pumped into electrical signals which through driver electronics and mechanicals drive the piston.

An embodiment provides a method of backlash calculation wherein the pump inlet and outlet can be closed such that the chamber is connected to neither the inlet nor the outlet (or if a syringed type piston, only the inlet). The piston can be moved in one direction, and since the chamber is closed, pressure (or vacuum) can build up in the chamber. Once this is established, the motion can be stopped, and a pressure measurement can then be stored by the system. The direction can be changed and the system can be driven to move the piston in the opposite direction while monitoring the pressure. This motion can be as resolute as possible. The pressure does not change direction until the backlash amount is moved and until the piston has actually started moving in the opposite direction. The amount of volume pumped until the pressure change in the other direction occurs is the backlash measured. The data to determine the backlash can be analyzed by the microprocessor that is generating the sequences to move the pump to enable the measurement. The microprocessor then will store the measured backlash onto a nonvolatile memory being housed by the electronics that are packaged with the pump. Every subsequent request of the pump motion will compensate by moving the piston more than the requested amount by the backlash amount, only for the first pump motion after a direction change.

One detailed description of a possible procedure for automated implementation of the backlash measurement follows. It is assumed that (a) a valve or other means exists such that the pump chamber can be either vented to the ambient environment (open) or sealed (closed) under the control of firmware; (b) the pump piston can be moved within the chamber under the control of firmware; and (c) a pressure transducer exists such that the pressure in the chamber can be sampled periodically by firmware. The procedure consists of three phases: 1) setup, 2) data capture, and 3) analysis.

The setup phase moves the piston to a desired initial location and vents the chamber such that the initial pressure is ambient (zero). The procedure in one embodiment includes the following steps: (1) Set the valve to the "open" position; (2) Set the piston to the initial location (near the fully aspirated position); (3) Pause to allow the chamber reach ambient pressure; and (4) Set the valve to the "closed" position.

During the data capture phase, pressure samples are captured and stored into memory at a fixed rate while the piston is moved through a sequence of operations. This sequence in one embodiment is (1) Repeat the following for N iterations; (2) Move the piston x distance in the dispense direction; and (3) Move the piston x distance in the aspirate direction. Each operation in this sequence can commence immediately following the completion of the previous operation.

Figure 10:
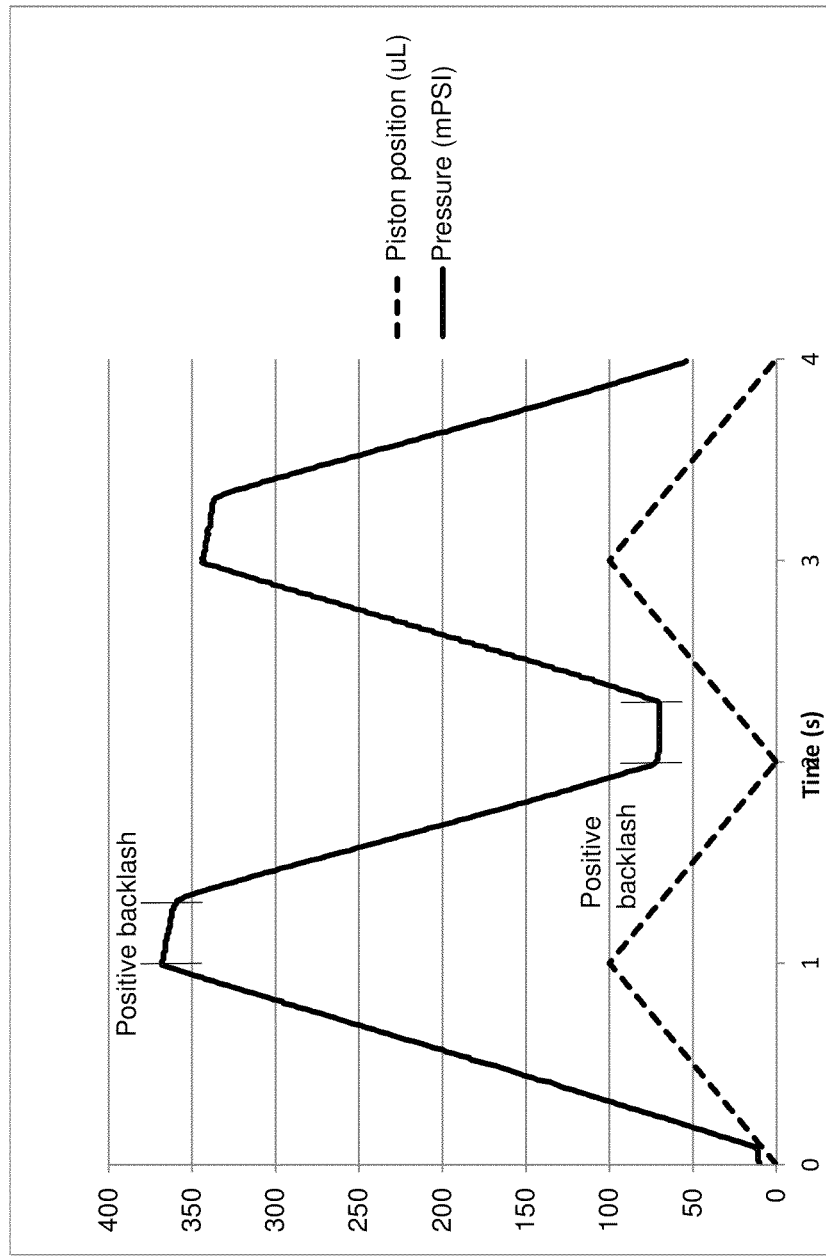
FIG. 10 is a graphical representation of varying piston positions and resulting pressures of a pump system of an embodiment.
Figure 11:
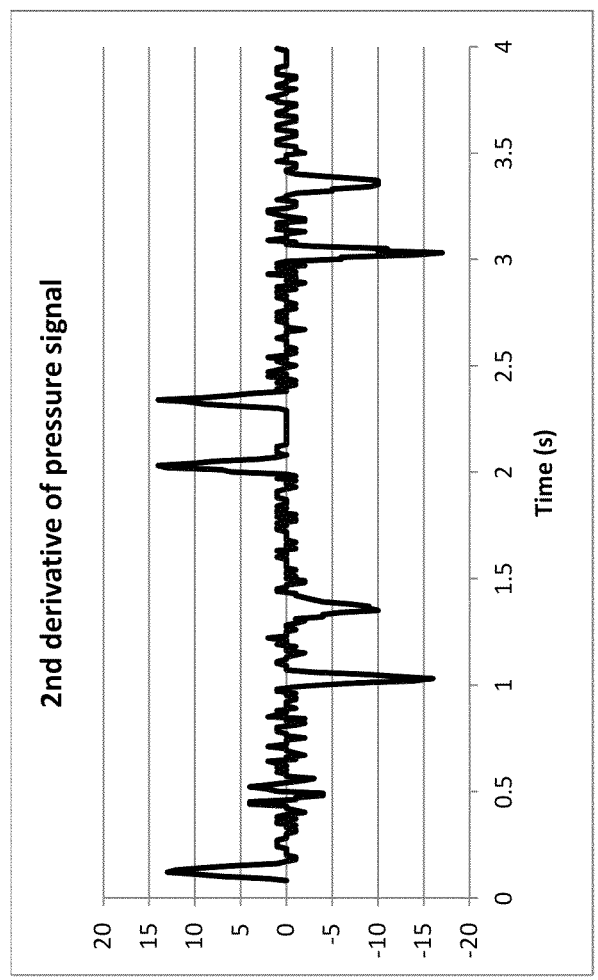
FIG. 11 is a graphical representation of the second derivative of the pressure signal in FIG. 10.

During the analysis phase, the captured pressure data is processed to produce the desired output: the pump backlash. FIG. 10 shows pressure measurement data for an example pump. The piston position plot shows the expected piston position if the backlash was equal to zero (ideal pump). Starting at time t=[1, 2, 3] seconds, there are time periods in which the motor driving the piston is moving but the pressure is not changing at the expected rate. The duration of one of these periods (in seconds) multiplied by the flow rate (in µL/s) equals the backlash (in µL). The duration of each backlash period is the distance between the locations where there is a step change in the slope of the pressure signal. These locations can be easily obtained by taking the second derivative of the pressure signal and looking for local maxima. A plot of the second derivative of the pressure signal in FIG. 10 is shown in FIG. 11. For N cycles, 2*N backlash measurements are produced. These can be averaged to produce a single value that is used to compensate for backlash during pump operations.

During normal operation, backlash compensation is performed by firmware in response to commands to move the pump piston. When the piston is commanded to move opposite the last direction, the backlash distance is added to the commanded distance and the motor is driven by this amount. This causes the piston to move the desired distance and displace the desired volume.

Commonly a pump will be commanded to aspirate a given volume at a given flow rate. For relatively low flow rates, the backlash compensation period may be large enough to cause the actual flow rate to be significantly lower than the commanded flow rate, even though the total volume is correct. In such a case, it is desirable (because it will be faster and save time) to compensate for the backlash using a higher velocity than the commanded flow rate and then switch to the commanded flow rate. Also in this case, the pump can be made to perform in the same way as a pump with no backlash at all flow rates.

Figure 13:
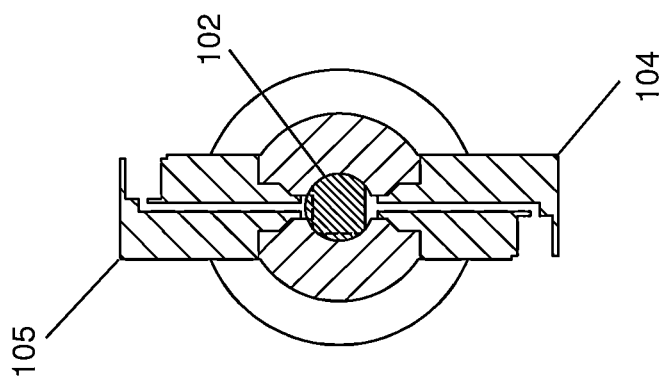
FIG. 13 is a cross-sectional view of a pump and piston of a pump system of an embodiment.

FIG. 12 illustrates an embodiment of a pump 100. The depicted pump 100 consists of a piston in a cylindrical chamber which contains inlet 104 and outlet 105 ports, and an attached pressure transducer 108. The piston is cylindrical with the exception of a flat surface. The piston can be rotated such that its flat surface points to the inlet port 104, the outlet port 105, or neither port. This arrangement is further illustrated in FIG. 13, which provides a pump/piston arrangement that has no valves, and depicts how the ports can be sealed off in order to facilitate the measurement of the backlash. Motors controlled by firmware drive the piston linear motion (to aspirate or dispense) and rotational motion (to connect to a port, acting as the valve). The electronics or printed circuit board (PCB) in FIG. 12 houses a nonvolatile memory which is used to store measured backlash for each individual pump.

The central processing unit (CPU) 110 of a microprocessor which performs the backlash measurement uses one sensor input and three control outputs. As shown in FIG. 12, the input (1) connects to the pressure transducer to collect the pressure data used to measure the backlash. Output (2) controls the piston rotation and is used to control whether the chamber is vented to ambient pressure or sealed. Output (3) connects to the nonvolatile memory and is used to store the computed backlash. Output (4) controls the piston linear motion and is used to move the piston in an iterative dispense/aspirate sequence while the pressure data is collected.

Pump Storage Liquid.

Certain embodiments of the diagnostic system provide a pump storage liquid which prevents unwanted freezing, seizing, or stiction (static friction) of a piston and cylinder type pump (such as IVEK's rotary/reciprocating Metering Pumps) during periods of non-use. The pump storage liquid is also referred to as pump storage fluid and pump prime fluid. Pump designs based on close-fitting ceramic-on-ceramic piston and cylinder sets are highly susceptible to freezing, seizing or stiction. During periods of non-use, residual liquid inside the pump (dead volume) may evaporate if allowed to dry out (open to ambient) and leave behind solids. These solids, while possibly very low in concentration or mass, may increase significantly the friction between the piston and cylinder. Under such conditions, the piston motion becomes frozen. This may require complete disassembly and cleanup of the pump. Additionally, this may cause mechanical breakdown of the coupling mechanism between the piston and motor.

The pump storage liquid can be used to provide a clinical laboratory instrument which is free of normal user maintenance or free of or has reduced mechanical breakdown (related to the pump) is an improvement. Normal user maintenance that may be eliminated includes operations that service a pump such as requiring the instrument operator to flush liquids and/or empty waste containers. Eliminating user maintenance saves operator time, and therefore lower costs. Eliminating components from an instrument such as liquid loops from an instrument reduces costs.

IVEK Corp. produces and sells ceramic positive displacement pumps with adequate volume metering precision and accuracy. The pumps are valve-less with close-fitting ceramic-on-ceramic piston and cylinder set. IVEK Corp. states in its use instructions that ceramic piston/cylinder sets are sensitive to neglect and may freeze if allowed to dry. Further, IVEK Corp. recommends the pump to remain wet at all times by means of liquid loop. If allowed to dry out, disassembly and cleaning of the pump is usually necessary. These manufacturer's storage options/requirements render its pump unsuitable for a clinical instrument designed for no or little user maintenance.

Thus, the pump system provides a means to employ a pump on an instrument where there is no or little user maintenance. Possible maintenance that the invention eliminates may include disassembly and cleaning of a pump, priming liquid for a liquid loop, and emptying waste from liquid loop. After proper application of a pump storage liquid of the invention, the pump does not require a liquid loop, and can be allowed to dry out (e.g., pump internal volume open to ambient) without risk of freezing, seizing or stiction. Upon re-start, the pump rapidly returns to its original performance. (See Example 6).

A pump storage liquid prevents or inhibits the formation of solids between the piston and cylinder by, for example, not evaporating and/or by solubilizing any residual salt or solids present in the dead volume of the pump. This non-volatile liquid acts as a lubricant for the seal or tight fitting piston and cylinder set. Stiction is avoided because lubricant persistently fills the gap between the piston and cylinder. In this manor the pump storage liquid prevents the pump seals or tight fitting piston and cylinder set from drying out and therefore prevents freezing, seizing, or stiction. Additionally, the present disclosure provides a pump storage liquid which enables the pump to recover from storage without wetting the seals or tight fitting piston and cylinder set.

The minimum amount of pump storage liquid required to protect a pump can be very low, e.g. 1 nL. The pump storage liquid can be present in an amount ranging from about 1 nL to about 2 nL, from about 1 nL to about 1.5 nL, or from about 1.5 nL to about 2 nL. The minimum amount of pump storage liquid required to protect the pump depends on the gap volume between the piston and cylinder set. For example, a one inch diameter piston and one inch length chamber with a two micron gap between piston and cylinder has a gap volume of 4 µL. This is the minimum amount of pump storage liquid required to protect such pump.

In some embodiments, a pump storage liquid of the invention contains a non-volatile, water soluble, salt solubilizing liquid that lubricates close-fitting ceramic-on-ceramic piston and cylinder set pumps. In some embodiments, a pump storage liquid is comprised of 30% by weight of diethylene glycol, 69.99% by weight of water, and 0.0013% by weight of PROCLIN® 200 (anti-microbial agent).

In some embodiments, a pump storage liquid is comprised of a lubricant such as diethylene glycol. The lubricant can comprise an ethylene glycol, including, but not limited to, ethylene glycol, diethylene glycol, triethylene glycol, tetraethylene glycol, polyethylene glycol or any combinations thereof. In some embodiment the lubricant can comprise a propylene glycol, including, but limited to propylene glycol, dipropylene glycol, tripropylene glycol, tetrapropylene glycol, polypropylene glycol or any combinations thereof. In some embodiments, a lubricant is comprised of glycerine. The lubricant can comprise both glycerine and glycols. In some embodiments, a pump storage liquid comprises between 5% and 95% by weight of lubricant. The pump storage liquid can contain water to reduce viscosity. The pump storage liquid can contain at least one anti-microbial agent or does not contain an anti-microbial agent.

In one embodiment, a pump storage liquid has at least one of the following properties: (1) Liquid at the operating temperature; (2) Low vapor pressure—does not evaporate; (3) Water soluble—readily flushed out of pump; (4) Solvent for residual salts or other solids within the pump dead volume; (5) Low surface tension—wets and fills gap between piston and cylinder; (6) Low viscosity—does not slow down fluid motions; (7) Chemically stable when inside pump or stored in intermediate containers; (8) Does not react with fluids for decontamination; (9) Chemically compatible with exposed materials; and (10) Does not interfere with adjacent operations. In some embodiments, a pump storage liquid has all of the above properties.

Some embodiments enable the use of a piston and cylinder type pump in a clinical instrument which has no installed liquids such as priming fluids, waste, wash liquids, cleaning liquids, or liquid loops. Some embodiments prevent unwanted freezing, seizing, or stiction of a piston and cylinder type pump, e.g., for up to six months, up to 9 months or up to 1 year periods of non-use. Some embodiments prevent unwanted freezing or seizing of a piston and cylinder type pump by the use of a pump storage liquid. Some embodiments provide a storage liquid for the pump which is chemically compatible with the parent instrument including the pump. Some embodiments provide a storage liquid which is chemically compatible with its intermediate storage container, e.g., a plastic clinical instrument. Some embodiments provide a storage liquid which also is suitable for priming a piston and cylinder type pump. Some embodiments provide a storage liquid which is operable at small volumes such as 1 nL.

Failsafe Mechanisms.

Some embodiments provide a failsafe mechanism for a cartridge-diagnostic instrument interaction, where the diagnostic instrument will detect whether the cartridge that the user inserted into the instrument was actually the identical cartridge that the user intended to run in the diagnostic instrument. For those cartridges that have an opened package expiry limit, the presented method will also detect whether the said time has expired or not, when the user inserts the cartridge into the instrument.

Certain embodiments of the diagnostic system make it impossible for the diagnostic instrument to process a cartridge that is different than the user indicated that he/she wanted to use. Other embodiments provide a mechanism to detect whether a cartridge has expired after it has been removed from its package, and scanned by the user. These mechanisms can provide easy and user transparent methods to assure fail-safe operation, where the possibility of producing wrong results is eliminated.

Figure 14:
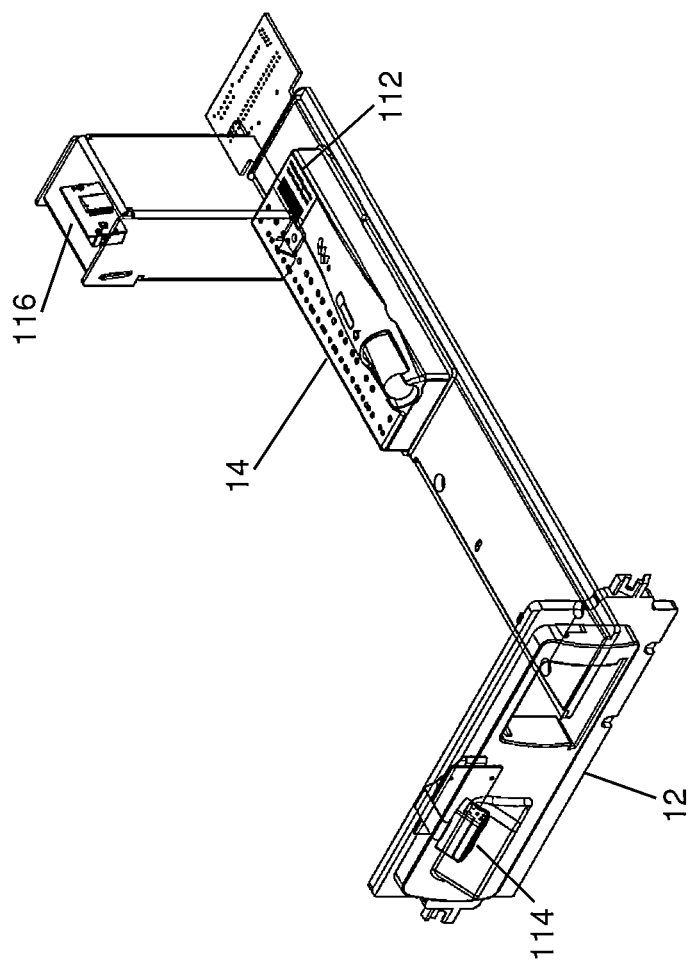
FIG. 14 is a perspective view of external and internal barcode scanners of a diagnostic system of an embodiment.

In certain embodiments, a failsafe mechanism is provided for a diagnostic instrument that processes cartridges with at least one patient sample on them. In some embodiments, cartridges are disposables. In some embodiments, the cartridges are labeled with computer scannable codes or machine readable codes, such as, a barcode 112, as shown in FIG. 14. A code reader, such as a 2-D barcode reader can be used on the diagnostic instrument that can read the barcode or other two-dimensional code on the cartridge 14 before the user inserts the cartridge into the diagnostic instrument 12. Information about the cartridge 14 and the test protocol to be applied (enabling the same diagnostic instrument to be able to process different types of cartridges) could be encoded on the barcode 112 along with the unique identifier for the specific cartridge, such as Lot Number and a Serial Number. It is contemplated that other machine readable or computer scannable codes can be used and read by other code readers and that additional mechanisms of scanning and reading digital information may be incorporated into the diagnostic instrument, such as a Q-reader with a 3-D scan code.

The diagnostic instrument 12 can be equipped with a computer code scanner, such as a barcode scanner, or an external scanner 114, that can scan the cartridge(s) outside of the diagnostic instrument 12, and a computer system running software that interacts with the barcode system and with the user through a display (not shown). In some embodiments, a cartridge 14 is removed from a protective package, and scanned by the diagnostic instrument 12. The diagnostic instrument 12 upon scanning and decoding the bar coded information will direct the software appropriately to display the cartridge information read from the barcode.

In some embodiments, the diagnostic system includes the use of a secondary barcode reader, or an internal scanner 116, that is housed inside the diagnostic instrument 12, that is aligned to read the barcode on the disposable cartridge 14, e.g., to compare via software with the previously read barcode (from outside) before starting the processing of the cartridge 14. This operation can be done totally transparent to the user, except when an inconsistency is detected with the cartridge that is scanned outside and with the one scanned inside, at which time the user is alerted.

Some embodiments can also include the start of a software timer when the user scans the cartridge outside the diagnostic instrument, and then when the cartridge is inserted into the diagnostic instrument and verified with the second bar code reader that the cartridge is the same as the one scanned outside. The software timer can be checked to ensure that the cartridge has been used within a recommended time limit after the first scan. Such a system is depicted in FIG. 14.

Instrument Software Steps.

Figure 15:
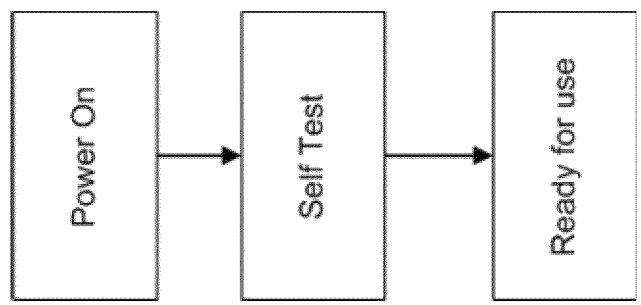
FIG. 15 is a flow chart for a startup sequence of an embodiment.

Various embodiments of the diagnostic system include software programs that control the electrical functions of the diagnostic system. Simple software guided workflows can be used, such as a simple start-up sequence set forth in FIG. 15. In some embodiments, upon daily power-up and prior to running each sample, a system completes a self-test and system is ready for use upon successful completion of these routines.

The operational specification describes the sequence of events that must occur in the course of a test cycle. For assaying an enzyme in a sample of blood or blood derivative, this specification discloses the following method: introducing the sample into a cartridge, metering of a portion of the sample, moving the metered sample with reagent at the analysis location, positioning the reacted sample at a sensor, and detecting the product of the reaction using a sensor.

The performance specification sets the criteria for parameters such as the range of results that will be reported, the necessary accuracy and precision of the test, and the acceptable operating conditions. The test results must match the sensitivity and range of the commonly accepted coagulation tests and must do so with comparable or better precision. Furthermore, as a point-of-care instrument may be operated by non-technically trained personnel, the instrument software must detect any cartridge errors that do occur.

Figure 16A:
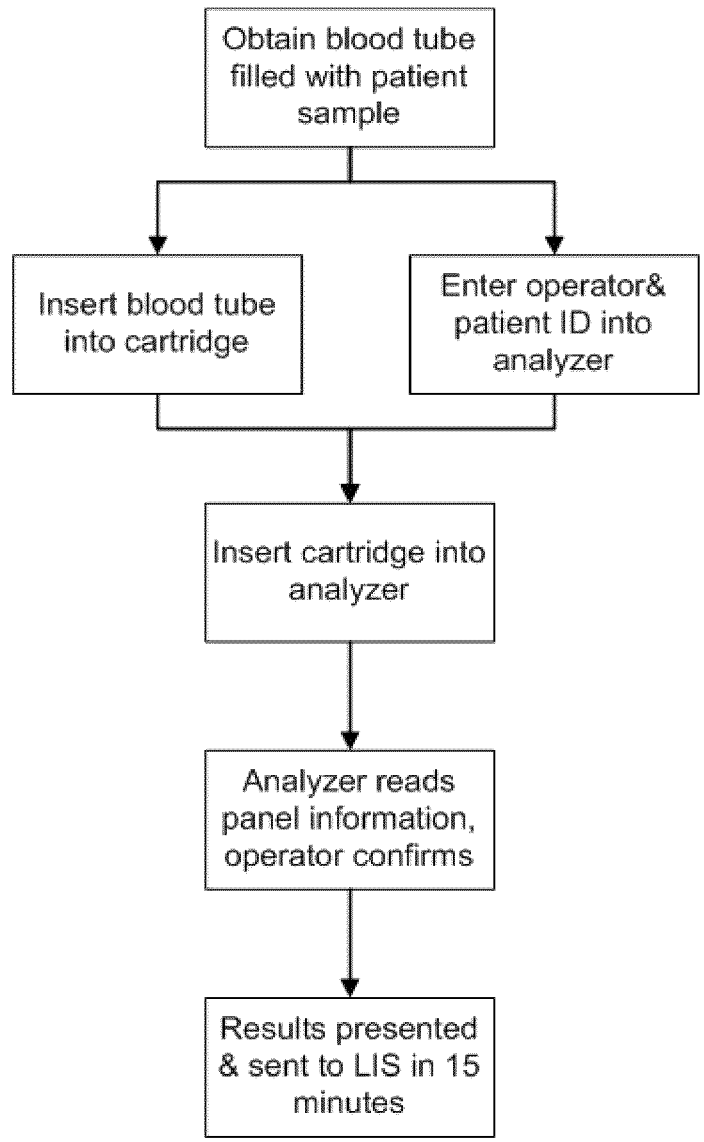
FIG. 16A is a flow chart for an instrument-driven work flow of an embodiment.
Figure 16B:
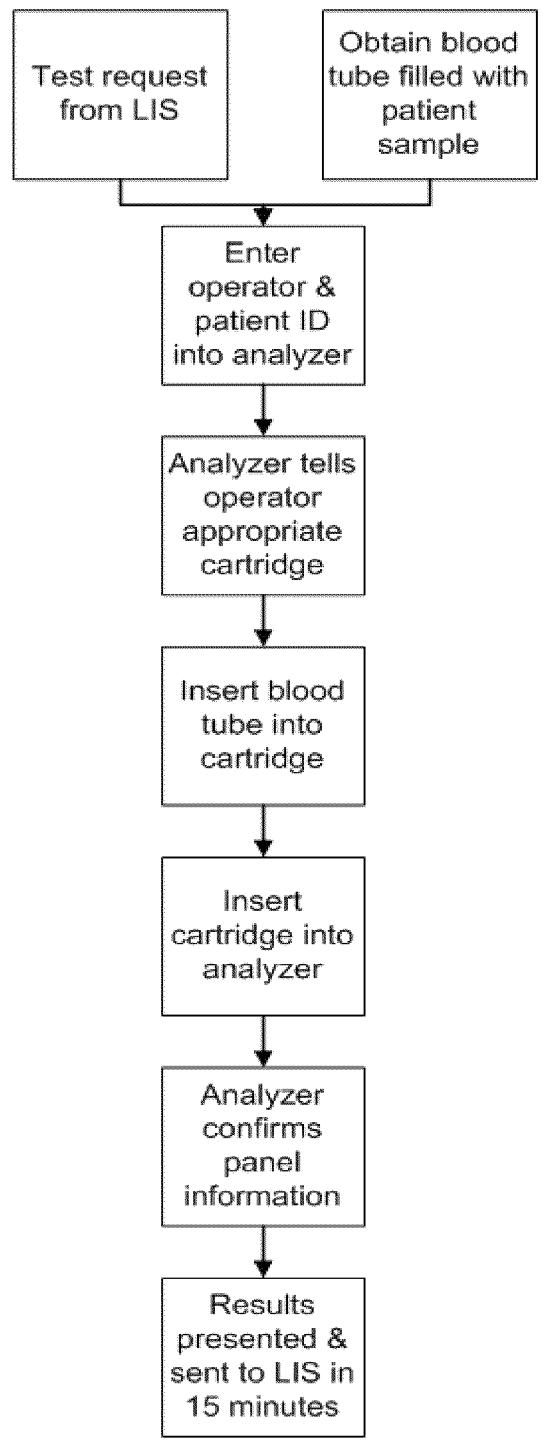
FIG. 16B is a flow chart for a laboratory information system (LIS)-driven work flow of an embodiment.

Additional steps for testing venous whole blood patient samples are shown in FIGS. 16A and 16B. Other sequences and options are possible and the following should be considered only as examples. An operator can draw blood into a blood tube using standard practices. In the instrument-driven mode, the operator (in either order) inserts the blood tube into the cartridge and enters the patient ID and operator ID into the diagnostic instrument. The operator can then insert the cartridge into the diagnostic instrument. The diagnostic instrument, after reading the panel information from the cartridge, may ask the operator to confirm the panel. Afterwards, the sample is processed and results are presented, for example, in roughly 15 minutes. In the laboratory information system (LIS)-driven mode, the diagnostic instrument is told the panel on the cartridge and the patient ID from the LIS. The diagnostic instrument, after the operator enters the patient ID, tells the operator which cartridge to use. The operator inserts the blood tube into that cartridge and inserts it into the diagnostic instrument. The diagnostic instrument confirms the correct cartridge is used, processes the sample, and presents the results.

All publications, patents and patent applications mentioned in this disclosure are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online.

Citation or discussion of a reference herein shall not be construed as an admission that such is prior art to the present invention.

As used herein the transitional term "comprising" is open-ended. A claim utilizing this term can contain elements in addition to those recited in such claim. Thus, for example, the claims can read on methods that also include other steps not specifically recited therein, as long as the recited elements or their equivalent are present.

For the purpose of illustrating the subject matter, there are depicted in the drawings certain embodiments of the subject matter. However, the present disclosure is not limited to the precise arrangements and instrumentalities of embodiments depicted in the drawings.

The following examples are merely illustrative and intended to be non-limiting.

EXAMPLES

Example 1

Internal Standard (IS)

A standardized quantity of 24,038 fluorescent beads yielded a fluorescent signal of 189,395. These fluorescent beads were processed as an IS in two test trials, with the following results in Table 1:

TABLE 1

|  | Test #1 | Test #2 |
| --- | --- | --- |
| Fluorescent signal | 149.608 | 167.056 |
| Number of beads | 18.989 | 21.203 |
| Bead Recovery | 79.0% | 88.2% |

In a test where the predetermined cutoff point for Failsafe mechanism is 85%, the run from test #2 did result in a PASS condition, when run from test #12 resulted in a FAIL condition.

Example 2

Use of IS as Failsafe to Detect False Negative Result

A standardized quantity of fluorescent labeled beads was added to assay reagents for a 5-fluorouracil assay. The reagents were incorporated onto a cartridge as part of a diagnostic system. Replicate measurements were made on a sample, where the sample was a 5-fluorouracil standard at 2000 ng/mL. The fluorescence signal and ECL signal results for four replicates are given in Table 2.

TABLE 2

| Test Number | ECL | Fluorescence |
| --- | --- | --- |
| 1 | 91775 | 81771 |
| 2 | 58521 | 49400 |
| 3 | 81484 | 79203 |
| 4 | 99932 | 78649 |

With the exception of test number 2, the ECL signal demonstrated consistent results, i.e. the precision was 10% CV for the three replicates. The fluorescent signal also demonstrated very consistent results, i.e. the precision was 2% CV for the three replicates.

The fluorescence signal for test number 2 was low, i.e. 49400 or 36% decreased from the fluorescent mean. The corresponding ECL signal for test number 2 was falsely low, i.e. 58521 or 38% decreased from the ECL mean. This indicated that the IS was able to detect as false negative ECL reading.

Example 3

Figure 17:
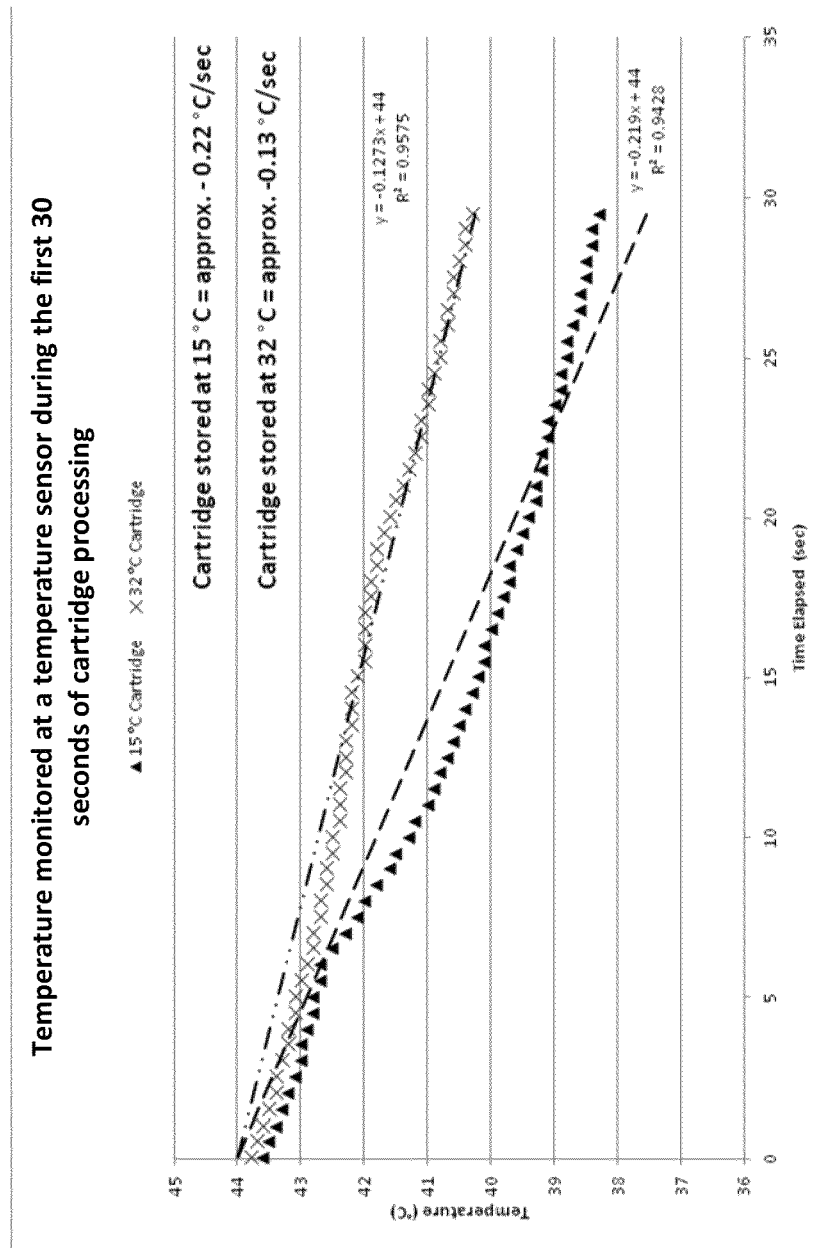
FIG. 17 is a graphical representation of temperature monitored for two cartridges in Example 3 and 4.

Detecting Cartridges Stored at Different Temperatures and Applying Different Incubation Set Temperatures for Cartridges Stored at Different Temperatures Cartridges stored at two different temperatures were differentiated by monitoring the temperature at a temperature sensor and evaluating the temperature loss over the first 30 seconds of cartridge processing. FIG. 17 is a graphical representation of the temperature monitored at a temperature sensor for two different cartridges stored at two different temperatures. When cartridges at two different storage conditions are detected, the instrument can apply different parameter values for the incubation.

Table 3 below shows a scenario when different incubation set temperatures were applied for the cartridges stored at two different storage temperatures. Table 3 below shows the set temperatures used for this example.

TABLE 3

| | Incubation temperature set points | |
| --- | --- | --- |
| CASE | For 15° C. Cartridge | For 32° C. Cartridge |
| A | 40.5° C. | 40.5° C. |
| B | 40.5° C. | 39° C. |

For Case A, both cartridges stored at 15° C. and 32° C. were incubated at the same incubator temperature set point. For Case B, cartridges stored at 15° C. and 32° C. were incubated at different incubator temperature set points. The chart below shows the differences in the incubation quality (average temperature during the incubation) between the cartridge stored at 15° C. and the cartridge stored at 32° C. for each sample for CASE A and CASE B. Note that this particular cartridge in this example had 7 samples available. The difference in the incubation quality shown in the chart below is the difference in average temperatures during incubation between the cartridge stored at 15° C. and the cartridge stored at 32° C. The lower difference in the incubation quality was desirable; the sample should be incubated identically independent from the cartridge's storage temperature.

Figure 18:
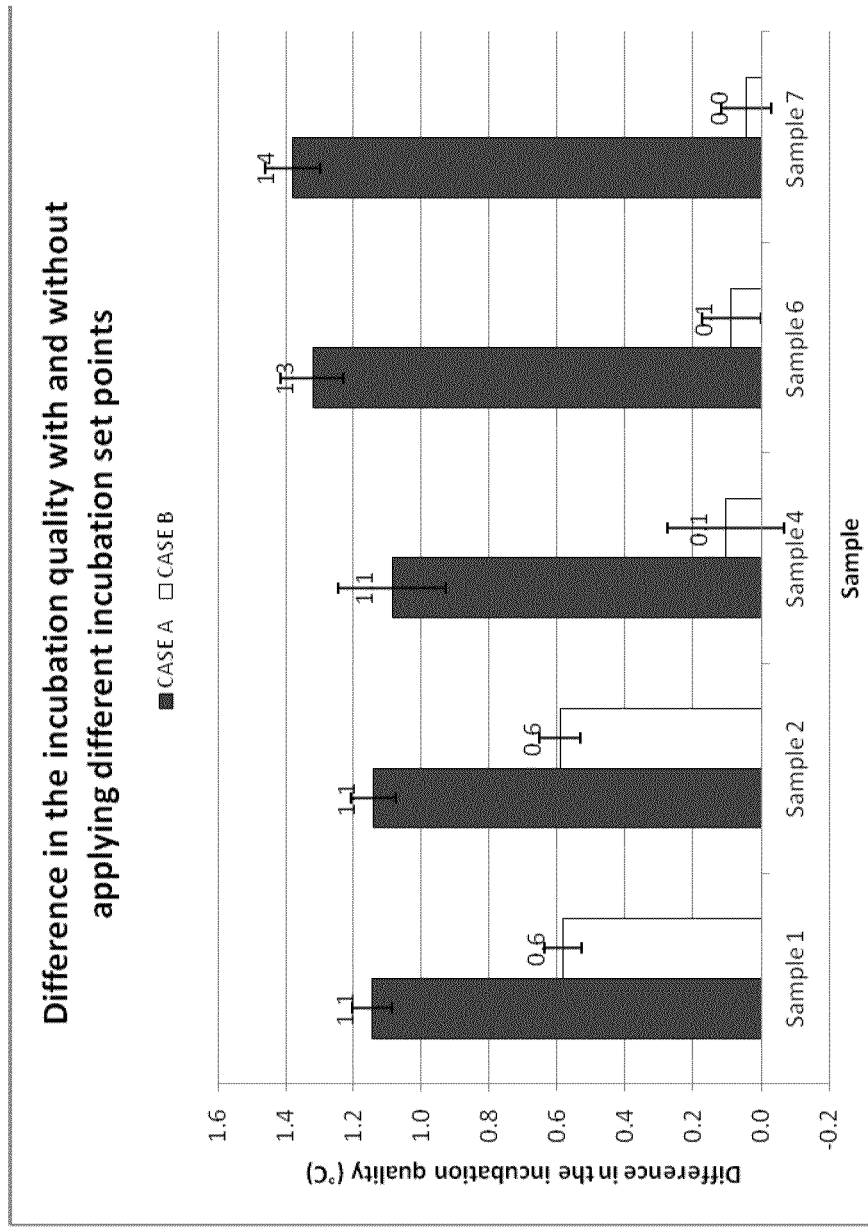
FIG. 18 is a graphical representation illustrating the difference in the incubation quality with and without applying different incubation set points in Example 3.

FIG. 18 is a graphical representation illustrating the difference in the incubation quality with and without applying different incubation set points. Without applying different temperature set points for cartridges stored at different temperatures, the difference in the incubation quality ranges between 1.1° C. and 1.4° C. When applying different temperature set points for cartridges stored at different temperatures, the difference in the incubation quality ranges between 0° C. and 0.6° C.

Example 4

Applying Different Boost Durations for Cartridges Stored at Different Temperatures The example below shows a scenario when cartridges stored at different temperatures were initially heated up for different durations. The initial heating up process was defined as boost in this example. Table 4 below shows different boost durations used for this example. The boost used in this example uses a 4° C. higher incubation temperature set point (44.5° C.) than the normal incubation temperature set point (40.5° C.) for 30 seconds or 330 seconds at the cartridge location during the blood filtration operation.

TABLE 4

| | Boost duration | |
| --- | --- | --- |
| CASE | For 15° C. Cartridge | For 32° C. Cartridge |
| A | 30 sec | 30 sec |
| B | 330 sec | 30 sec |

Notice that, for Case A, both cartridges stored at 15° C. and 32° C. had the same boost duration. For Case B, cartridges stored at 15° C. and 32° C. had different boost durations. The chart below shows the differences in the incubation quality (average temperature during incubation) between the cartridge stored at 15° C. and the cartridge stored at 32° C. for each sample for CASE A and CASE B. Note that this particular cartridge in this example had 7 samples available. The difference in the incubation quality shown in the chart below is the difference in average temperatures during incubation between the cartridge stored at 15° C. and the cartridge stored at 32° C. The lower difference in the incubation quality was desirable; the sample should be incubated identically independent from the cartridge's storage temperature.

Figure 19:
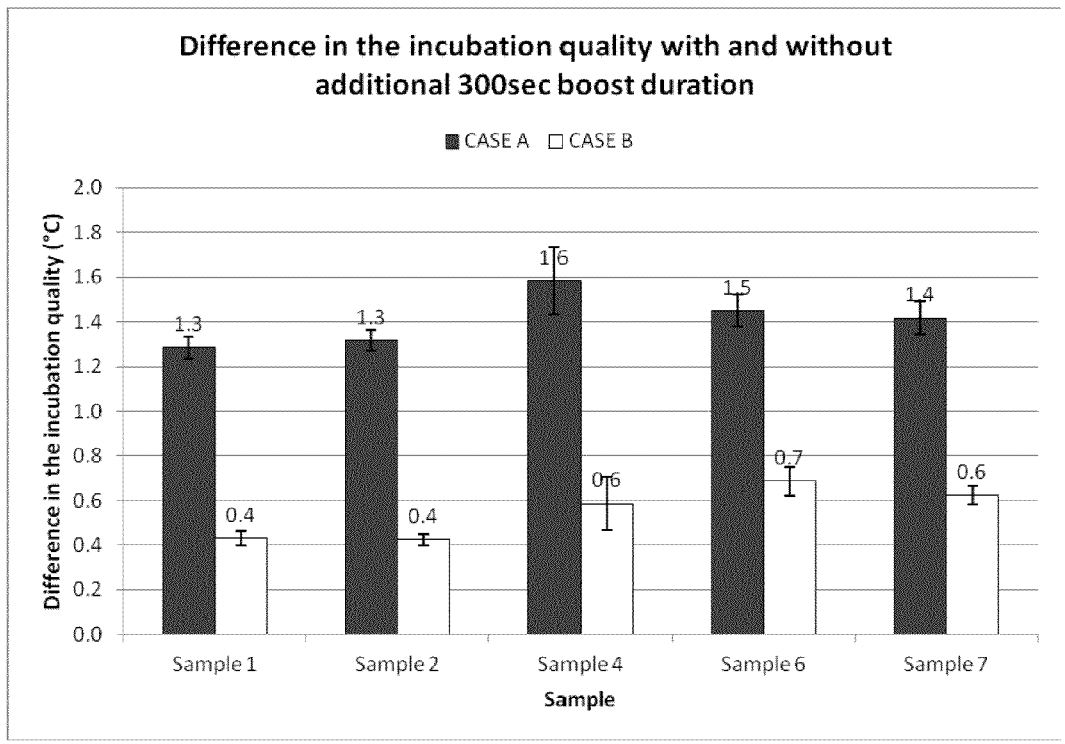
FIG. 19 is a graphical representation illustrating differences in incubation quality in Example 4.

FIG. 19 is a graphical representation illustrating differences in incubation quality with and without additional boost duration. Without applying different boost durations for cartridges stored at different temperatures, the difference in the incubation quality ranges between 1.3° C. and 1.6° C. When applying different boost durations for cartridges stored at different temperatures, the difference in the incubation quality ranges between 0.4° C. and 0.6° C.

Example 5

Measurement of Backlash

Currently pump backlash is measured by isolating the chamber and moving the piston back and forth at a constant velocity which capturing pressure data. The amount of time that the motor is in motion while the pressure is not changing directly translates to the pump backlash at that location.

Firmware compensates for this backlash by moving the pump linear motor an additional distance (equal to the backlash) when the piston is commanded to move in the opposite direction as its last displacement. The correct operation of this compensation mechanism can be verified by confirming using the same pressure method that the backlash is near zero once compensation is enabled. It is desirable however to have an independent verification of this functionality. For this reason, a test was devised to verify proper operation by measuring the mass of the displaced liquid.

An analytical balance was used to weigh the liquid. Pump storage liquid was used because its evaporation rate is lower than water. A container partially filled with Pump storage liquid was placed on the balance, and tubing which connects to the pump waste port was suspended in the liquid such that the tube was not in contact with any wall of the container.

The pump was thoroughly flushed to remove all air from the system. The piston flat was positioned toward the waste port. The piston was moved to the position 100 µL from home, with the last direction being dispense and the last velocity being 10 µL/s. Subsequent motion was at 10 µL/s, which was the velocity at which the backlash was measured using the pressure method.

The balance was tared, the piston was dispensed 10 µL, and the change in weight was recorded. The balance was tared again, the piston was aspirated by 10 µL, and the change in weight was again recorded. This procedure was executed with backlash compensation disabled and enabled.

Since the last piston direction before the test was dispense, the change in volume measured after the dispense stroke was expected to be 10 µL regardless of the backlash. For the aspirate direction, the change in volume was expected to be (10 µL—backlash) with backlash compensation disabled and 10 µL with it enabled.

The density of the pump storage liquid sample was measured to be 1.039 g/mL. This value was used to convert the measured weight into volume. The pump under test was 1_350194_008. Before running the verification, the backlash was measured using the pressure method in 4 trials. The results were [3.3 µL, 3.2 µL, 3.1 µL, 3.1 µL]. Based on these four measurements, backlash was determined to be 3.2 µL.

Table 5 below provides the change in volume (in µL) as measured by the analytical balance for both dispense and aspirate strokes of the test. Since the backlash was 3.2 µL, it was expected that the change in volume for the aspirate stroke would be 6.8 µL with backlash compensation disabled. 6.6 µL was actually measured, which is within the allowed measurement error. For the aspirate stroke with backlash compensation enabled, it was expected that the change in volume would be 10 µL and it was actually 9.9 µL, which was also within the allowed measurement error.

TABLE 5

| Backlash compensation in firmware (µL) | Disabled | Enabled |
| --- | --- | --- |
| Δvol dispense (µL) | 9.6 | 9.3 |
| Δvol aspirate (µL) | −6.6 | −9.9 |

Based on this test run, the displacement error in the aspirate direction improved from −34% to −1%. Thus, when applying the backlash correction, accuracy was improved. Without backlash correction the pump aspirated 6.6 µl when it was desired to aspirate 10 µl. With the backlash correction applied the pump aspirated 9.9 µl, which is an improvement.

Example 6

Pump Storage Liquid

To prepare a pump for storage it is flushed with a pump storage liquid. The following example demonstrates how flushing is accomplished. An example of a routine procedure for preparing a pump (IVEK Linear B size pump module mfg. part #032106-7007) for storage is to first draw air into the pump to remove working fluid (such as aqueous solution with surfactant, amines, salts, and buffer components). Significant working fluid remains in the pump as dead volume is approximately 75 µL in this example. Pump storage liquid, composed of 30% diethylene glycol in water, is then drawn into pump so as to exchange with the residual working fluid. Significant quantities of salts from the working fluid remain inside the pump due to its dead volume. The operation must draw (1 mL) in sufficient pump storage liquid to get enough lubricant into the gap between the piston and cylinder. Lastly, the pump is flushed with air to remove the pump storage liquid. A significant amount of pump storage liquid, and specifically diethylene glycol lubricant remains inside the pump's piston cylinder gap. The preparation for storage operation takes 45 seconds. The quantity of lubricant is sufficient to protect the pump for at least six months at 30° C.

What is claimed is:
1. A diagnostic system having a closed fluidic pathway, comprising:
   a diagnostic instrument comprising:
      at least two probes;
      a diagnostic fluidic pathway;
      a non-electrochemiluminescence (ECL) detection system;

an ECL detection system fluidically connected to the non-ECL detection system; and
a pump;
a cartridge comprising:
at least one needle;
at least one reservoir;
at least one fluidic seal; and
at least one fluidic channel,
wherein the closed fluidic pathway comprises the diagnostic fluidic pathway of the diagnostic instrument; and
the at least one fluidic channel of the cartridge begins at the at least one needle of the cartridge, passes through the diagnostic instrument, and ends at the at least one reservoir of the cartridge, and is capable of providing fluid from the cartridge to the diagnostic instrument.

2. The diagnostic system of claim 1, wherein the at least two probes are capable of engaging with the at least one reservoir, and
wherein the at least two probes comprise a first probe capable of engaging with the cartridge and/or a waste probe capable of engaging the cartridge.

3. The diagnostic system of claim 2, wherein the first probe fluidically connects to a first reservoir of the cartridge.

4. The diagnostic system of claim 3, further comprising diagnostic reagents provided within the first reservoir.

5. The diagnostic system of claim 2, wherein the waste probe fluidically connects to a waste reservoir of the cartridge.

6. The diagnostic system of claim 5, wherein the closed fluidic pathway ends in the waste reservoir.

7. The diagnostic system of claim 2, wherein the diagnostic system further comprises a motion assembly in the diagnostic system.

8. The diagnostic system of claim 7, wherein the motion assembly has two axes mechanically connected to the first probe and the waste probe.

9. The diagnostic system of claim 1, wherein the at least one reservoir comprises a first reservoir and a waste reservoir within the closed fluidic pathway.

10. The diagnostic system of claim 9, wherein the at least one reservoir is capable of being used multiple times including providing liquids.

11. The diagnostic system of claim 9, wherein the at least one reservoir is capable of being used multiple times including receiving liquids.

12. The diagnostic system of claim 9, wherein when the first reservoir is emptied, the first reservoir is capable of being used as the waste reservoir.

13. The diagnostic system of claim 1, wherein the diagnostic instrument further comprises a motion assembly,
wherein the cartridge comprises two or more reservoirs, and
wherein the motion assembly is capable of positioning the cartridge such that a first of the two or more reservoirs is part of the closed fluidic pathway and re-positioning the cartridge such that a second of the two or more reservoirs is a part of the closed fluidic pathway when the first of the two or more reservoirs is not part of the closed fluidic pathway.

14. The diagnostic system of claim 1, wherein the diagnostic fluidic pathway comprises one or more components capable of carrying fluids through the diagnostic instrument, and wherein a first of the one or more components has a diameter that is the same as or smaller than the diameter of a second of the one or more components.

15. The diagnostic system of claim 1, wherein the closed fluidic pathway is capable of reducing the potential for carryover between the diagnostic instrument and the cartridge.

16. The diagnostic system of claim 1, wherein the closed fluidic pathway prevents carryover between one or more different cartridges used with the diagnostic instrument such that there is substantially no detectable carryover between diagnostic tests of one or more different cartridges.

17. The diagnostic system of claim 1, wherein the at least two probes comprise a first probe and a waste probe,
wherein the at least one reservoir comprises a first reservoir and a waste reservoir, and
wherein the closed fluidic pathway runs from the first reservoir to the first probe, to the non-ECL detection system, to the ECL detection system, to the pump, to the waste probe, and to the waste reservoir.

18. The diagnostic system of claim 1, wherein at least one reagent and at least one waste material are stored in the cartridge.

19. The diagnostic system of claim 1, wherein the closed fluidic pathway does not store any of a sample, a liquid and at least one reagent in the diagnostic instrument.

20. The diagnostic system of claim 1, wherein a sample provided in the cartridge passes through the closed fluidic pathway originating in the cartridge to the closed fluidic pathway of the diagnostic instrument, and substantially all of the sample ends in the at least one reservoir in the cartridge.

21. The diagnostic system of claim 1, wherein all fluids are stored on the cartridge.

22. The diagnostic system of claim 1, wherein all dry reagents are stored on the cartridge.

23. A diagnostic system having a closed fluidic pathway, comprising:
a diagnostic instrument having a set of fluidic control elements, comprising:
a non-electrochemiluminescence (ECL) detection system;
a first probe fluidically connected to the non-ECL detection system by at least one fluidic tube;
an ECL detection system fluidically connected to the non-ECL detection system by at least one fluidic tube;
a pump fluidically connected to the ECL detection system by at least one fluidic tube and fluidically connected to a waste probe by at least one fluidic tube; and
a motion assembly having two axes mechanically connected to the first probe and the waste probe; and
a cartridge, comprising:
at least one needle;
at least one reservoir;
at least one fluidic seal; and
at least one fluidic channel, wherein the closed fluidic pathway has a substantially single direction of flow in a pathway fluidically connecting the diagnostic instrument and the cartridge.

24. The diagnostic system of claim 23, wherein the at least one reservoir comprises a first reservoir and a waste reservoir within the closed fluidic pathway.

25. The diagnostic system of claim 24, wherein when the first reservoir is emptied, the first reservoir is capable of being used as the waste reservoir.

26. The diagnostic system of claim 23, wherein the at least one reservoir is capable of being used multiple times including providing liquids.

27. The diagnostic system of claim 23, wherein the at least one reservoir is capable of being used multiple times including receiving liquids.

28. The diagnostic system of claim 23, wherein the first probe fluidically connects to a first reservoir of the cartridge.

29. The diagnostic system of claim 28, further comprising diagnostic reagents provided within the first reservoir.

30. The diagnostic system of claim 23, wherein the waste probe fluidically connects to a waste reservoir of the cartridge.

31. The diagnostic system of claim 30, wherein the closed fluidic pathway ends in the waste reservoir.

32. The diagnostic system of claim 23, wherein the cartridge comprises two or more reservoirs, and
wherein the motion assembly is capable of positioning the cartridge such that a first of the two or more reservoirs is part of the closed fluidic pathway and re-positioning the cartridge such that a second of the two or more reservoirs is a part of the closed fluidic pathway when the first of the two or more reservoirs is not part of the closed fluidic pathway.

33. The diagnostic system of claim 23, wherein the diagnostic fluidic pathway comprises one or more components capable of carrying fluids through the diagnostic instrument, wherein a first of the one or more components has a diameter that is the same as or smaller than the diameter of a second of the one or more components.

34. The diagnostic system of claim 23, wherein the closed fluidic pathway is capable of reducing the potential for carryover between the diagnostic instrument and the cartridge.

35. The diagnostic system of claim 23, wherein the closed fluidic pathway prevents carryover between one or more different cartridges used with the diagnostic instrument such that there is substantially no detectable carryover between diagnostic tests of one or more different cartridges.

36. The diagnostic system of claim 23, wherein the at least one reservoir comprises a first reservoir and a waste reservoir, and
wherein the closed fluidic pathway runs from the first reservoir to the first probe, to the non-ECL detection system, to the ECL detection system, to the pump, to the waste probe, and to the waste reservoir.

37. The diagnostic system of claim 23, wherein at least one reagent and at least one waste material are stored in the cartridge.

38. The diagnostic system of claim 23, wherein a sample provided in the cartridge passes through the closed fluidic pathway originating in the cartridge to the closed fluidic pathway of the diagnostic instrument, and substantially all of the sample ends in the at least one reservoir in the cartridge.

39. The diagnostic system of claim 23, wherein all fluids are stored on the cartridge.

40. The diagnostic system of claim 23, wherein all dry reagents are stored on the cartridge.

41. A diagnostic system having a closed fluidic pathway, comprising:
a diagnostic instrument comprising:
an internal standard module;
a first probe fluidically connected to the internal standard module by at least one fluidic tube;
an electrochemiluminescence (ECL) detection system fluidically connected to the internal standard by at least one fluidic tube;
a pump fluidically connected to the ECL detection system by at least one fluidic tube and fluidically connected to a waste probe by at least one fluidic tube; and
a cartridge comprising:
at least one needle;
at least one reservoir;
at least one fluidic seal; and
at least one fluidic channel, wherein the closed fluidic pathway comprises the diagnostic fluidic pathway of the diagnostic instrument; and
the at least one fluidic channel of the cartridge begins at the least one needle of the cartridge, passes through the diagnostic instrument, and ends at the at least one reservoir of the cartridge, and is capable of providing fluid from the cartridge to the diagnostic instrument.

42. The diagnostic system of claim 41, wherein the at least one reservoir comprises a first reservoir and a waste reservoir.

43. The diagnostic system of claim 42, wherein the first reservoir and the waste reservoir are the same reservoir.

44. The diagnostic system of claim 42, wherein the first reservoir and the waste reservoir are not the same reservoir.

45. The diagnostic system of claim 41, wherein the first probe fluidically connects to a first reservoir of the cartridge.

46. The diagnostic system of claim 45, wherein the first reservoir contains diagnostic reagents.

47. The diagnostic system of claim 41, wherein the waste probe fluidically connects to a waste reservoir of the cartridge.

48. The diagnostic system of claim 47, wherein the waste reservoir receives waste materials.

49. The diagnostic system of claim 48, wherein waste materials include at least one of a processed reagent, a blood filtrate, and a processed plasma.

50. The diagnostic system of claim 41, wherein the diagnostic fluidic pathway comprises one or more components capable of carrying fluids through the diagnostic instrument, and wherein a first of the one or more components has a diameter that is the same as or smaller than the diameter of a second of the one or more components.

51. The diagnostic system of claim 41, wherein the closed fluidic pathway is capable of reducing the potential for carryover between the diagnostic instrument and the cartridge.

52. The diagnostic system of claim 41, wherein the closed fluidic pathway prevents carryover between one or more different cartridges used with the diagnostic instrument such that there is substantially no detectable carryover between diagnostic tests of one or more different cartridges.

53. The diagnostic system of claim 41, wherein the at least one reservoir comprises a first reservoir and a waste reservoir, and
wherein the closed fluidic pathway runs from the first reservoir to the first probe, to the non-ECL detection system, to the ECL detection system, to the pump, to the waste probe, and to the waste reservoir.

54. The diagnostic system of claim 41, wherein at least one reagent and at least one waste material are stored in the cartridge.

55. The diagnostic system of claim 41, further comprising a motion assembly.

56. The diagnostic system of claim 55, wherein the motion assembly has two axes mechanically connected to the first probe and the waste probe.

57. The diagnostic system of claim 41, wherein all fluids are stored on the cartridge.

58. The diagnostic system of claim 41, wherein all dry reagents are stored on the cartridge.

59. A method of temperature control within the diagnostic system of claim 41, comprising:
measuring with a sensor a starting temperature of the cartridge containing a biological sample and at least one reagent;
comparing the starting temperature of the cartridge to a target temperature;

heating with a heater the cartridge to the target temperature; and maintaining the target temperature using a closed loop control for a period of time.

60. The method of claim 59, wherein measuring the starting temperature comprises measuring with a sensor the rate of an incubator's temperature loss after the cartridge is placed on the incubator.

61. The method of claim 60, wherein measuring the starting temperature comprises measuring with a sensor the rate of an incubator plate's temperature loss after the cartridge is placed on the incubator plate.

62. The method of claim 60, wherein the same sensor is used to measure the starting temperature and in the closed loop control to maintain the target temperature.

63. The method of claim 60, wherein the rate of temperature loss is related to the rate that heat transfers from the incubator plate to the cartridge, and the starting temperature of the cartridge.

64. The method of claim 60, wherein the sensor is integral with the incubator plate.

65. The method of claim 60, wherein the heater is integral with the incubator plate.

66. The method of claim 59, wherein the temperature control is a closed-loop feedback control.

67. The method of claim 59, wherein maintaining the target temperature using a closed loop control comprises:
intermittently measuring with the sensor the temperature of the cartridge during operation of the diagnostic system;
comparing the cartridge temperature to the target temperature; and
heating with the heater the cartridge to the target temperature.

68. The method of claim 59, wherein the period of time is equal to or less than the time it takes for the diagnostic system to complete a full diagnostic test.

69. A method of temperature control within the diagnostic system of claim 41, comprising:
in a first zone of an incubator, measuring with a first sensor a starting temperature of a portion of the cartridge containing a biological sample and at least one reagent, wherein the cartridge is shorter in length than the length of the incubator and the portion of the cartridge only contacts the first zone of the incubator;
comparing the starting temperature of the portion of the cartridge to a first target temperature;
heating with a first heater the portion of the cartridge to the first target temperature;
maintaining the first target temperature of a portion of the cartridge using a closed loop control for a period of time; and
in a second zone of the incubator, measuring with a second sensor a starting temperature of a second portion of the cartridge containing a biological sample and at least one reagent, wherein the second portion of the cartridge only contacts the second zone of the incubator;
comparing the starting temperature of the second portion of the cartridge to a second target temperature;
heating with a second heater the second portion of the cartridge to the second target temperature; and
maintaining the target temperature of the second portion of the cartridge using a second closed loop control for a period of time.

70. The method of claim 69, wherein the first and second zones of the multi-zone incubator operate independently of one another.

71. The method of claim 69, wherein the measurements in the first and second zones occur simultaneously during operation of the diagnostic system.

72. The method of claim 69, wherein the measurements in the first and second zones occur at different times during operation of the diagnostic system.

73. The method of claim 69, wherein the first target temperature and the second target temperature are different.

74. The method of claim 69, wherein the first target temperature and the second target temperature are the same.

75. The method of claim 69, wherein the first sensor and the second sensor are different.

76. The method of claim 69, wherein the first heater and the second heater are different.

77. The method of claim 69, wherein the period of time is equal to or less than the time it takes for the diagnostic system to complete a full diagnostic test.

78. The diagnostic system of claim 41, wherein the internal standard module comprises an apparatus for measuring bead recovery, comprising:
a housing;
a tubing assembly of the diagnostic fluidic pathway, located within the housing in fluidic communication with the ECL detection system;
a fluorescence excitation source; and
a fluorescence light detector, wherein the fluorescence excitation source is capable of emitting light such that the light reflects off of or is transmitted by the fluorescent beads in the fluid provided in the cartridge flowing through the tubing assembly of the diagnostic fluidic pathway,
wherein the fluid provided in the cartridge passes through the closed fluidic pathway originating in the cartridge to the closed fluidic pathway of the diagnostic instrument such that substantially all of the fluid ends in the at least one reservoir in the cartridge, and
wherein the fluorescence light detector is capable of measuring the amount of light reflected off of or transmitted by the beads in the fluid to determine whether an acceptable level of beads is present in the fluid indicating a positive bead recovery measurement.

79. A method of detecting and measuring bead recovery, comprising:
illuminating a fluid containing a known amount of fluorescent and non-fluorescent beads flowing through the closed fluidic pathway of the diagnostic system of claim 78;
detecting light transmitted and/or reflected by the illuminated fluorescent beads flowing through the tubing assembly of the diagnostic fluidic pathway of the diagnostic system;
converting the transmitted light and/or the reflected light into one or more measurable electrical signals;
processing the one or more measurable electrical signals to calculate an internal standard which is directly related to the amount of fluorescent beads traveling through the tubing assembly; and
comparing a magnitude of the one or more measurable electrical signals to a predicted magnitude based on the known amount of fluorescent and non-fluorescent beads within the fluid, wherein amount of the one or more measurable electrical signals is directly correlated to the amount of non-fluorescent beads present in the closed fluidic pathway of the diagnostic system.

80. A method of measuring electrochemiluminescence (ECL) bead recovery, comprising:

illuminating a fluid containing a known amount of fluorescent beads and ECL beads flowing through the tubing assembly of the diagnostic system of claim 78;

measuring fluorescence from the fluorescent beads; and processing the measured fluorescence signal to calculate ECL bead recovery by comparing the measured fluorescence signal to a fluorescence signal from a standardized quantity of fluorescent beads.

81. The diagnostic system of claim 41, further comprising an assay composition comprising a mixture of at least one of a fluorescent labeled bead and at least one of an electrochemi-luminescence (ECL) labeled bead.

82. The assay composition of claim 81, wherein beads can be both fluorescently labeled and ECL labeled.

83. A method of measuring backlash of the pump in the diagnostic system of claim 41, comprising:

sealing an area in the pump to create a chamber capable of generating pressure within the sealed area;

measuring a change in pressure within the sealed area in the pump, wherein the change in pressure is generated by a first change in the pump direction from aspirate to dispense and/or from dispense to aspirate;

measuring a change in pressure within the sealed area in the pump, wherein the change in pressure is generated by a second change in the pump direction from aspirate to dispense and/or from dispense to aspirate, and wherein the first change in the pump direction is opposite from the second change in the pump direction;

processing the change in pressure measured within the sealed area in the pump into a backlash amount; and adjusting the desired pump volume to compensate for the backlash amount processed and measured.

84. The method of claim 83, wherein the measured backlash amount is stored and saved by the diagnostic instrument of the diagnostic system to be used repeatedly through cartridge processing cycles of the diagnostic system, wherein the stored data is capable of increasing efficiency of the diagnostic instrument for additional uses.

85. The method of claim 83, wherein the pump further comprises a pressure sensor capable of measuring the change in pressure in the sealed area of the pump.

86. The method of claim 83, wherein the pump comprises a piston and a cylinder pump.

87. The method of claim 83, wherein the pump comprises a motor driven piston and a cylinder pump.

88. The method of claim 83, wherein the pump comprises a motor driven piston, a cylinder pump, and a pressure sensor.

89. The method of claim 83, wherein the pump comprises a motor driven piston, a cylinder pump, a pressure sensor, and a flat.

90. The method of claim 83, wherein the pump comprises a close fitting ceramic piston and a cylinder pump.

91. The method of claim 83, wherein the pump is an IVEK pump.

92. The method of claim 83, wherein the pump piston comprises a flat.

93. A method to improve pump accuracy of the pump of the diagnostic system of claim 41, comprising:

measuring an amount of backlash present in the pump; and compensating subsequent pump displacements by the amount of backlash measured in the pump, by:

sealing an area in the pump to create a chamber capable of generating pressure within the sealed area;

measuring a change in pressure within the sealed area in the pump, wherein the change in pressure is generated by a first change in the direction of a piston of the pump;

measuring a change in pressure within the sealed area in the pump, wherein the change in pressure is generated by a second change in the direction of the piston of the pump, wherein the first change in the direction of the piston is opposite from the second change in the direction of the piston, and wherein the first change in the direction of the piston and the second changes in direction of the piston are alternated repeatedly such that sufficient pressure to measure is generated within the sealed area;

processing the change in pressure measured within the sealed area in the pump into a backlash amount;

deriving backlash volume from the amount of backlash measured, by:

measuring the time duration that the pressure level created in the sealed area did not respond to the reversed piston motor movement; and multiplying the time duration by piston motor rate to calculate backlash volume; and adjusting the desired pump volume to compensate for the calculated backlash volume and improve pump accuracy.

94. The method of claim 93, wherein the chamber is isolated such that when the piston is moved the chamber is capable of generating pressure.

95. The method of claim 93, wherein the pump comprises a piston and a cylinder pump.

96. The method of claim 93, wherein the pump comprises a motor driven piston and a cylinder pump.

97. The method of claim 93, wherein the pump comprises a motor driven piston, a cylinder pump, and a pressure sensor.

98. The method of claim 93, wherein the pump comprises a motor driven piston, a cylinder pump, a pressure sensor, and a flat.

99. The method of claim 93, wherein the pump comprises a close fitting ceramic piston and a cylinder pump.

100. A method to improve pump accuracy of the pump of the diagnostic system of claim 41, comprising:

measuring for the amount of backlash present in the pump and then compensating subsequent pump displacements by the backlash by:

positioning a piston in the chamber of the pump such that the chamber is not connected to any inlet or outlet ports;

moving the piston using a piston motor until a predetermined pressure level is reached;

reversing the piston motor direction and measure pressure or vacuum;

deriving backlash volume by measuring the time duration that the pressure or vacuum level did not respond to the reversed piston motor movement, and multiplying the time duration by piston motor rate to calculate backlash volume.

101. The method of claim 100, wherein the pump comprises a piston and a cylinder pump.

102. The method of claim 100, wherein the pump comprises a motor driven piston and a cylinder pump.

103. The method of claim 100, wherein the pump comprises a motor driven piston, a cylinder pump, and a pressure sensor.

104. The method of claim 100, wherein the pump comprises a motor driven piston, a cylinder pump, a pressure sensor, and a flat.

105. The method of claim 100, wherein the pump comprises a close fitting ceramic piston and a cylinder pump.

106. The method of claim 100, wherein the pump is an IVEK pump.

107. The method of claim 100, wherein the pump piston comprises a flat.

108. The method of claim 100, wherein the pump has a dual action with linear and rotational motion.

109. A method of increasing time efficiency of the pump used in the diagnostic system of claim 41, comprising:
measuring the amount of backlash volume present in the pump through pressure changes;
processing the pressure measurement data into a backlash amount;
adjusting the desired pump volume to compensate for the backlash amount measured; and
reducing processing time of the pump based on adjustments of pump volume.

110. A method of use of a composition comprising glycol useful for lubricating the pump of the diagnostic system of claim 41, comprising:
flushing the pump immediately after use with the composition such that during periods of non-use of the pump remains primed for operation.

111. The method of claim 110, wherein the composition further comprises glycerine.

112. The method of claim 110, wherein the glycol is diethylene glycol.

113. The method of claim 110, wherein the glycol comprises at least one of ethylene glycol, triethylene glycol, tetraethylene glycol, and polyethylene.

114. The method of claim 110, wherein the composition further comprises an anti-microbial agent.

115. The method of claim 110, wherein the composition further comprises water.

116. The method of claim 110, wherein the composition is capable of being a lubricant for the pump.

117. The method of claim 110, wherein the composition comprises a non-volatile liquid.

118. The method of claim 110, wherein the composition is capable of inhibiting solid formation between a piston and a cylinder of the pump of the diagnostic system.

119. The diagnostic system of claim 41, further comprising a composition useful for lubricating the pump comprising glycol.

120. The diagnostic system of claim 41, further comprising a composition useful for lubricating the pump comprising glycol and glycerine.

121. The diagnostic system of claim 41, further comprising a composition useful for preventing freezing or seizing or stiction of the pump during periods of non-use of the pump, comprising at least one of the following properties: liquid at the operating temperature; low vapor pressure; water soluble; solvent for residual salts or other solids within the pump dead volume; low surface tension; low viscosity; chemically stable when inside pump or stored in intermediate containers; does not react with fluids for decontamination; chemically compatible with exposed materials; and does not interfere with adjacent operations.

122. A method of preventing freezing or seizing or stiction during periods of non-use of the pump of the diagnostic system of claim 41, comprising:
circulating a composition comprising glycol through the pump of the diagnostic system.

123. The method of claim 122, wherein the composition is stored until use on the cartridge of the diagnostic system that is fluidically connected to the pump of the diagnostic system.

124. The method of claim 123, wherein the composition is returned to the cartridge after it flows through the closed fluidic pathway of the diagnostic system.

125. The method of claim 122, wherein less than about 2.0 nL of the composition is required to protect the pump during periods of non-use.

126. The method of claim 122, wherein less than about 1.5 nL of the composition is required to protect the pump during periods of non-use.

127. The method of claim 122, wherein less than about 1.0 nL of the composition is required to protect the pump during periods of non-use.

128. The method of claim 122, wherein about 1.0 nL of the composition is required to protect the pump during periods of non-use.

129. A method of identifying the cartridge of the diagnostic system of claim 41, comprising:
scanning for a first time a scannable code on the cartridge, wherein the scannable code contains data on at least one of a test protocol for the cartridge, a patient information, a lot number for the cartridge contents, a serial number for the cartridge, an expiration date for the cartridge;
inserting the cartridge into the diagnostic instrument;
scanning for a second time the scannable code on the cartridge while inside the diagnostic instrument;
comparing the data between the scans to ensure that the correct cartridge was inserted into the diagnostic instrument; and
providing feedback to a user on whether the correct cartridge was inserted into the diagnostic instrument.

130. The method of claim 129, wherein the first scan of the scannable code is scanned by an external scannable code scanner.

131. The method of claim 129, wherein the scannable code contains data on all of a test protocol for the cartridge, a patient information, a lot number for the cartridge contents, a serial number for the cartridge, and an expiration date for the cartridge.

132. A method of identifying the cartridge of the diagnostic system of claim 41, comprising:
scanning a scannable code on the cartridge, wherein the scannable code contains data on at least one of a test protocol for the cartridge, a patient information, a lot number for the cartridge contents, a serial number for the cartridge, an expiration date for the cartridge;
inserting the cartridge into the diagnostic instrument;
processing the data from the scanned scannable code to ensure that the correct cartridge was inserted into the diagnostic instrument; and
providing feedback to a user on whether the correct cartridge was inserted into the diagnostic instrument.

133. The method of claim 132, further comprising scanning the scannable code on the cartridge while inside the diagnostic instrument with an internal scanner; and
comparing the data between the scans to ensure that the correct cartridge was inserted into the diagnostic instrument.

134. The method of claim 132, wherein the first scan of the scannable code is scanned by an external scannable code scanner on the exterior of the diagnostic instrument.

135. A method of preventing reuse of the cartridge of the diagnostic system of claim 41, comprising:
scanning a scannable code on the cartridge with an external scanner, wherein the scannable code contains data on at least one of a record of use, a test protocol for the cartridge, a patient information, a lot number for the cartridge contents, a serial number for the cartridge, an expiration date for the cartridge;
inserting the cartridge into the diagnostic instrument;
scanning the scannable code on the cartridge with an internal scanner once inside the diagnostic instrument;
comparing the data between the scans to identify whether an unused cartridge was inserted into the diagnostic instrument; and
providing feedback to a user on whether the cartridge was previously used by the diagnostic instrument.

136. The method of claim 135, wherein the cartridge is removed from a protective package before scanning by the external scanner.

137. The method of claim 135, wherein the diagnostic instrument will not allow processing the cartridge if the cartridge is a used cartridge.

138. The method of claim 135, wherein the internal scanner scans the cartridge before processing of the cartridge.

139. A method of preventing improper use of the cartridge of the diagnostic system of claim 41, comprising:
scanning a scannable code on a protective package containing the cartridge, wherein the first scan sets a first limit of an expiry time limit predetermined for proper use of the cartridge;
introducing the cartridge into the diagnostic instrument with an internal scanner;
scanning the scannable code on the cartridge with the internal scanner, wherein the internal scan sets a second limit of an expiry not to exceed a predetermined limit for proper use of the cartridge;
calculating the difference between the first and the second time limits;
comparing the difference in time to the predetermine time limit for proper cartridge use; and
providing feedback to user if time limit was breached.

140. A diagnostic system having a closed fluidic pathway, comprising:
a diagnostic instrument comprising:
an internal standard;
a first probe fluidically connected to the internal standard module by at least one fluidic tube;
an electrochemiluminescence (ECL) detection system fluidically connected to the internal standard by the at least one fluidic tube, wherein the ECL detection system comprises:
an ECL detection module comprising:
an enclosure having a top and a base, wherein the surface of the base is flat and capable of forming a working surface, and the top is attached to the base capable of forming the bottom of the enclosure thereby forming a cavity having a height;
a first electrode; a second electrode; and a first gasket, wherein the first electrode and the second electrode are stacked and separated by the first gasket, wherein the base supports the first electrode, and wherein the first gasket has a compressible thickness that is capable of creating a predetermined separation gap between the first and second electrodes;
a transparent window formed out of the second electrode to facilitate ECL detection; and
a printed circuit board, wherein the printed circuit board is positioned next to the base of the ECL detection module, electrically connecting components within the ECL detection system;
a pump fluidically connected to the ECL detection system by at least one fluidic tube and fluidically connected to a waste probe by at least one fluidic tube;
a cartridge comprising:
at least one needle;
at least one reservoir;
at least one fluidic seal; and
at least one fluidic channel, wherein the closed fluidic pathway comprises the diagnostic fluidic pathway of the diagnostic instrument; and
the at least one fluidic channel of the cartridge, wherein the closed fluidic pathway begins at the least one needle of the cartridge, passes through the diagnostic instrument, and ends at the at least one reservoir of the cartridge, and is capable of providing fluid from the cartridge to the diagnostic instrument.

141. A diagnostic system having a closed fluidic pathway, comprising:
a diagnostic instrument comprising:
an internal standard;
a first probe fluidically connected to the internal standard module by at least one fluidic tube;
an electrochemiluminescence (ECL) detection system fluidically connected to the internal standard by the at least one fluidic tube, wherein the ECL detection system comprises:
an ECL detection module comprising:
an enclosure having a top and a base, wherein the surface of the base is flat and capable of forming a working surface, and the top is attached to the base capable of forming the bottom of the enclosure thereby forming a cavity having a height;
a first electrode; a second electrode; and a first gasket, wherein the first electrode and the second electrode are stacked and separated by the first gasket, wherein the base supports the first electrode and wherein the first gasket has a thickness that is capable of creating a predetermined separation gap between the first and second electrodes;
a transparent window formed out of the second electrode capable of facilitating ECL detection;
a second gasket capable of fluidically sealing the enclosure and capable of having a differential compliance less than the first gasket to maintain the electrode separation gap; and
a printed circuit board positioned next to the base of the ECL detection module, electrically connecting components within the ECL detection system;
a pump fluidically connected to the ECL detection system by at least one fluidic tube and fluidically connected to a waste probe by at least one fluidic tube;
a cartridge comprising:
at least one needle;
at least one reservoir;
at least one fluidic seal; and
at least one fluidic channel, wherein the closed fluidic pathway comprises the diagnostic fluidic pathway of the diagnostic instrument; and
the at least one fluidic channel of the cartridge, wherein the closed fluidic pathway begins at the least one needle of the cartridge, passes through the diagnostic instrument, and ends at the at least one reservoir of the cartridge, and is capable of providing fluid from the cartridge to the diagnostic instrument.

142. A diagnostic system having a closed fluidic pathway, comprising:
a diagnostic instrument comprising:
an internal standard;
a first probe fluidically connected to the internal standard module by at least one fluidic tube;

an electrochemiluminescence (ECL) detection system fluidically connected to the internal standard by the at least one fluidic tube, wherein the ECL detection system comprises:
- an ECL detection module comprising:
  - an enclosure having a top and a base, wherein the surface of the base is flat and capable of forming a working surface, and the top is attached to the base capable of forming the bottom of the enclosure thereby forming a cavity having a height;
  - a measurement containment area; a first electrode surface; a second electrode surface; and a first gasket cutout, wherein the measurement containment area is formed in part by the first electrode surface, the second electrode surface and the first gasket cutout, and wherein the first electrode and the second electrode are stacked and separated by the first gasket, and
  - wherein the base supports the first electrode, the first gasket has a compressible thickness, and the electrode/gasket stack resides in the cavity capable of creating a predetermined separation gap between the first and second electrode surfaces;
  - a transparent window in at least one cutout of the second electrode capable of facilitating ECL detection, wherein at least one inlet port and at least one outlet port in the at least one cutout of the second electrode are capable of transporting fluids in and out of the measurement containment area; and
  - an opaque enclosure surrounding the ECL module capable of exclude ambient light;
- a pump fluidically connected to the ECL detection system by at least one fluidic tube and fluidically connected to a waste probe by at least one fluidic tube;
a cartridge comprising:
- at least one needle;
- at least one reservoir;
- at least one fluidic seal; and
- at least one fluidic channel, wherein the closed fluidic pathway comprises the diagnostic fluidic pathway of the diagnostic instrument; and
- the at least one fluidic channel of the cartridge, wherein the closed fluidic pathway begins at the least one needle of the cartridge, passes through the diagnostic instrument, and ends at the at least one reservoir of the cartridge, and is capable of providing fluid from the cartridge to the diagnostic instrument.

143. The diagnostic system of claim 142, wherein the measurement containment area is capable of being sealed without using adhesives.

144. The diagnostic system of claim 142, wherein the measurement containment area is capable of being sealed using two or more gaskets.

145. The diagnostic system of claim 144, wherein the use of two or more gaskets more compliant than the first gasket the first and second electrode spacing height is capable of being maintained.

146. The diagnostic system of claim 142, wherein when the clamped distortion of the gasket in the unclamped gasket cutouts is compensated for, the measurement containment area is capable of being made precise and accurate.

147. The diagnostic system of claim 142, wherein when the gasket raw material thickness variation in the unclamped gasket cutouts is compensated for, the measurement containment area is capable of being made precise and accurate.

148. The diagnostic system of claim 142, wherein an opaque printed circuit board is capable of blocking ambient light leakage.

149. The diagnostic system of claim 142, wherein an opaque printed circuit board—with one or more opaque coatings is capable of blocking ambient light leakage.

150. The diagnostic system of claim 142, wherein an opaque printed circuit board with one or more internal or external metal foil layers is capable of blocking ambient light leakage.

* * * * *